US006403090B1

(12) United States Patent
Cutler et al.

(10) Patent No.: US 6,403,090 B1
(45) Date of Patent: Jun. 11, 2002

(54) PEPTIDES WHICH MIMIC CANDIDA CARBOHYDRATE EPITOPES AND THEIR USE IN A VACCINE

(75) Inventors: Jim E. Cutler; Yongmoon Han, both of Bozeman, MT (US)

(73) Assignee: The Research and Development Institute Inc., Bozeman, MT (US)

( * ) Notice: Subject to any disclaimer, the term of this patent is extended or adjusted under 35 U.S.C. 154(b) by 0 days.

(21) Appl. No.: 09/334,922

(22) Filed: Jun. 17, 1999

Related U.S. Application Data

(60) Division of application No. 09/076,883, filed on May 13, 1998, which is a continuation-in-part of application No. 08/756,014, filed on Nov. 25, 1996, now abandoned, which is a continuation-in-part of application No. 08/483,558, filed on Jun. 7, 1995, now Pat. No. 5,578,309, which is a continuation-in-part of application No. 08/247,972, filed on May 23, 1994, now abandoned.
(60) Provisional application No. 60/045,030, filed on Apr. 28, 1997, and provisional application No. 60/046,299, filed on May 13, 1997.

(51) Int. Cl.[7] ...................... A61K 39/395; C07K 16/00; C12P 21/08

(52) U.S. Cl. ................................ 424/152.1; 424/130.1; 424/141.1; 530/388.1; 530/388.4; 530/388.5; 530/389.1; 530/389.5

(58) Field of Search .......................... 530/387.1, 388.1, 530/388.4, 389.1, 389.5; 424/130.1, 137.1, 141.1, 150.1, 164.1

(56) References Cited

U.S. PATENT DOCUMENTS

| | | |
|---|---|---|
| 4,310,514 A | 1/1982 | Durette |
| 4,315,913 A | 2/1982 | Durette |
| 4,323,560 A | 4/1982 | Baschang et al. |
| 4,368,190 A | 1/1983 | Shen et al. |
| 4,397,838 A | 8/1983 | d'Hinterland et al. |
| 4,522,811 A | 6/1985 | Eppstein et al. |
| 4,670,382 A | 6/1987 | Buckley et al. |
| 4,678,748 A | 7/1987 | Sutka et al. |
| 4,732,763 A | 3/1988 | Beck et al. |
| 4,806,465 A | 2/1989 | Buckley et al. |
| 5,032,404 A | 7/1991 | Lopez-Berenstein |
| 5,288,639 A | 2/1994 | Burnie et al. |
| 5,332,660 A | 7/1994 | Takeda et al. |
| 5,578,309 A | 11/1996 | Cutler et al. |

FOREIGN PATENT DOCUMENTS

WO    WO95/31998    11/1995

OTHER PUBLICATIONS

Ashman et al. "Murine candidiasis: Cell–mediated immune responses correlate directly with susceptibility and resistance to infection." Immunol. Cell. Biol., 68: 15–20; 1990.

Ashman et al., "Murine candidiasis: Strain dependence of host responses after immunization." Immunol. Cell. Biol., 66: 231–237; 1988.
Ashman et al., "Murine candidiasis: Sex differences in the severity of tissue lesions are not associated with levels of serum C3 and C5." Immunol. Cell. Biol., 69: 7–10; 1991.
Ashman et al., "Strain dependence of antibody–mediated protection in murine systemic candidiasis." J. Inf. Dis. 168: 511–513; 1993.
Balish et al., "Serum antibody response to gnotobiotic athymic and euthymic mice following alimentary tract colonization and infection with *Candida albicans*." Can. J. Microbiol. 37: 204–210; 1991.
Banerjee et al., "Role of antibody in defence against murine candidosis." Indian J. Med. Res., 79: 760–765; 1984.
Barbas, C.F., "Recent advances in phage display." Curr. Op. Biotech., 4: 526–530;1993.
Bendel et al., "Distinct mechanisms of epithelial adhesion for *Candida albicans* and *Candida tropicalis*. Identification of the participating ligands and development of inhibitory peptides." J. Clin. Invest., 92: 1840–1849; 1993.
Berger et al., "IgE antibodies to *Staphylococcus aureus* and *Candida albicans* in patients with the syndrome of hyper–immunoglobulin E and recurrent infections." J. Immunol., 125: 2437–2443; 1980.
Bistoni et al., "Mucosal and systemic T helper cell function after intragastric colonization of adult mice with *Candida albicans*." J. Inf. Dis., 168: 1449–1457; 1993.
Bistoni et al., "Evidence for macrophage–mediated protection against lethal *Candida albicans* infection," Infect. Immun., 51(2): 668–674, 1986.
Brawner et al., "Oral candidiasis in HIV–infected patients." AIDS Reader, Jul./Aug.: 117–124; 1992.
Brawner et al., "Variability in expression of a cell surface determinant on *Candida albicans* as evidenced by an agglutinating monoclonal antibody." Infect. Immun., 43: 966–972; 1984.
Brawner et al., "Variability in expression of cell surface antigens of *Candida albicans* during morphogenesis." Infect. Immun., 51: 337–343; 1986.
Burford–Mason, et al., "Transient abrogation of immunosupression in a patient with chronic mucocutaneous candidiasis following vaccination with *Candida albicans*." J. Inf., 14: 147–157; 1987.
Burgess et al., "Possible dissociation of the heparin–binding and mitogeniuc activities of heparin–binding (acidic fibroblast) growth factor from its receptor–binding activities by site–directed mutagenisis of a single lysine residue," J Cell Biol., 111: 2129–2138; 1990.

(List continued on next page.)

Primary Examiner—Patricia A. Duffy
(74) Attorney, Agent, or Firm—Morgan, Lewis & Bockius LLP

(57) ABSTRACT

A composition, pharmaceutical composition, vaccine and method for the treatment of disseminated candidiasis due to infection by *C. albicans*. The composition includes phosphomannan of *C. albicans*, peptide mimotopes of phosphomannan epitopes, or polynucleotides encoding the peptide mimotopes. Monoclonal antibodies for use in passive immunization against candida infections are also provided.

15 Claims, 25 Drawing Sheets

OTHER PUBLICATIONS

Burritt et al., "Topological mapping of neutrophil cytochrome b epitopes with phage–display libraries." J. Biol. Chem., 270: 16974–16980; 1995.

Calderone et al., "Adherence and receptor relationships in *Candida albicans.*" Microbiol. Rev., 55: 1–20; 1991.

Cantorna et al., "Mucosal and systemic candidiasis in congentially immunodeficient mice." Infect. Immun., 58(4): 1093–1100; 1990.

Cantorna et al., "Acquired immunity to systemic candidiasis in immunodeficient mice." J. Infect. Dis., 164: 936–943; 1991.

Casanova et al., "Phosphate–containing proteins and glycoproteins of the cell wall of *Candida albicans*, " Infect. Immun., 59(3): 808–813, 1991.

Casanova et al., "Characterization of cell wall proteins from yeast and mycelial cells of *Candida albicans,*" Infect. Immun., 59(3): 808–813, 1991.

Cassone et al., "Rats clearing a vaginal infection by *Candida albicans* acquire specific, antibody–mediated resistance to vaginal reinfection." Infect. Immun., 63: 2619–2624; 1995.

Cenci et al., "Role of L3T4+ lymphocytes in protective immunity to systemic *Candida albicans* infection in mice." Infect. Immun., 57: 3581–3587; 1989.

Cuff et al., "The induction of T–suppressor cells with a soluble extract of *Candida albicans.*" Cellular Immunology, 122: 71–82; 1989.

Cutler et al., "Antigenic variability of *Candida albicans* cell surface." Curr. Top. Med. Mycol,. 5: 27–47; 1994.

Cutler, J.E., "Putative virulence factors of *Candida albicans.*" Annu. Rev. Microbiol., 45: 187–218; 1991.

Cutler et al., "Characteristics of *Candida albicans* adherence to mouse tissue." Infect. Immun., 58: 1902–1908; 1990.

Cutler et al., "Production of monoclonal antibodies against glycan adhesins of *Candida albicans.*" B. Maresca and G.S. Kobayashi (ed.), Man. Molec. Meths. Med. Mycol, Springer–Verlag; 1994.

Czuprynski et al., "Administration of anti–granulocyte mAb RB6–8C5 impairs the resistance of mice to *Listeria monocytogenes* infection." J. Immunol., 152: 1836–1846; 1994.

Denning et al., "Antifungal prophylaxis during neutropenia or allogenic bone marrow transplantation: What is the state of the art?" Chemotherapy, 38(Suppl. 1): 43–49; 1992.

Diamond et al., "Damage to pseudohyphal forms of *Candida albicans* by neutrophils in the absence of serum in vitro." J. Clin. Invest., 61: 349–359: 1978.

Domer J.E., "Intragastric colonization of infant mice with *Candida albicans* induces systemic immunity demonstrable upon challenge as adults." J. Inf. Dis., 157: 950–958. 1988.

Fidel et al., "Candida–specific cell–mediated immunity is demonstrable in mice with experimental vaginal candidasis." Infect. Immun., 61: 1990–1995; 1993.

Filler et al., "An enzyme–linked immunosorbent assay for quantifying adherence of Candida to human vascular endothelium." J. Infect. Dis., 156: 561–566; 1987.

Filler et al., "*Candida albicans* stimulates endothelial cell eicosanoid production." J. Infect. Dis., 164: 928–935; 1991.

Filler et al., "Mechanisms by which *Candida albicans* induced endothelial cell prostaglandin synthesis." Infect. Immun., 62: 1064–1069; 1994.

Fraser–Smith et al., "Protective effect of muramyl dipeptide analogs against infections of *Pseudomonas aeruginosa* or *Candida albicans* in mice." Infect. Immun., 34: 676–683; 1981.

Fukayama et al., "Adherence of cell surface mutants of *Candida albicans* to buccal epithelial cells and analyses of the cell surface proteins of the mutants," Infect. Immun., 59(4): 1341–1345, 1991.

Garner et al., "Effect of in vivo administration of recombinant murine gamma interferon on in vitro lymphoproliferative responses following immunization with *Candida albicans.*" Infect. Immun., 60: 1927–1935; May 1992.

Garner et al., "Lack of effect of *Candida albicans* mannan on development of protective immune responses in experimental murine candidiasis," Infect. Immun., 62(2): 738–741, 1994.

Gerhold et al., "It's the genes! EST access to human genome content." BioEssays, 18: 973–981; 1996.

Giger et al., "Experimental murine candidiasis: Pathological and immune responses to cutaneous inoculation with *Candida albicans.*" Infect. Immun., 19: 499–509; 1978.

Gilmore et al., "An iC3b receptor on *Candida albicans*: Structure, function, and correlates for pathogenicity." J. Infect. Dis., 157: 38–46; 1988.

Gomez et al., "Biochemical and immunological characterization of MP 65, a major mannoprotein antigen of the opportunistic human pathogen *Candida albicans.*" Infect. Immun., 68(2): 694–701; 2000.

Gozalbo et al., "Effect of digitonin on membrane–bound and chitosomal chitin synthetase activity in protoplasts from yeast cells of *Candida albicans.*" Antonie van Leeuwenhock, 64: 67–74; 1993.

Gustafson et al., "Molecular mimicry in *Candida albicans*. Role of an integrin analogue in adhesion of the yeast to human endothelium." J. Clin. Inv., 87: 1896–1902; 1991.

Han et al., "Antibody response that protects against disseminated candidiasis," Infect. Immun., 63(7): 2714–2719; 1995.

Han et al., "Binding of *Candida albicans* yeast cells to mouse popliteal lymph node tissue is mediated by macrophages." Infect. Immun., 61: 3244–3249; 1993.

Han et al., "Mouse sialoadhesin is not responsible for *Candida albicans* yeast cell binding to splenic marginal zone macrophages." Infect. Immun., 62: 2115–2118; 1994.

Hasenclever et al., "Antigenic studies of Candida. I. Observation of two antigenic groups in *Candida albicans.*" J. Bacteriol., 82: 570–573; 1961.

Hasenclever et al., "Antigenic studies of Candida. II. Antigenic relation of *Candida albicans* group A and group B to *Candida stellatoidea* and *Candida tropicalis.*" J. Bacteriol., 82: 574–57; 1961.

Hazen, K.C., "Influence of growth condistions on cell surface hydrophobicity of *Candida albicans* and *Candida glubrata.*" Infect. Immun., 54: 267–271; 1986.

Hazen et al., "Surface hydrophobic and hydrophilic protein alterations in *Candida albicans.*" FEMS Microbiol. Lett., 107: 83–88; 1993.

Hazen et al., "A polystyrene microsphere assay for detecting surface hydrophobicity variations within *Candida albicans* poplulations." J. Microbiol. Methods., 6: 289–299; 1987.

Hazen, K.C., "Cell surface hydrophobicity of medically important fungi, especially *Candida species.*" *Microbial Cell Surface Hydrophobicity*, ed. Doyle et al., American Society of Microbiology, Washington, 1990, pp. 249–295.

Hazen et al., "Hydrophobic cell wall protein glycosylation by the pathogenic fungus *Candida albicans.*" Can. J. Microbiol., 40: 266–272: 1994.

Hazen et al., "Differential adherence of hydrophobic and hydrophilic *Candida albicans* yeast cells to mouse tissues." Infect. Immun., 59: 907–912; 1991.

Hector et al., "Immune responses to *Candida albicans* in genetically distinct mice." Infect. Immun., 38: 1020–1028; 1982.

Hurtrel et al., "Absence of correlation between delayed–type hypersensitivity and protection in experimental systemic candidiasis in immunized mic." Infect. Immun., 31: 95–101; 1981.

James et al., "Cell–wall glucans of *Cryptococcus neoformans* CAP 67." Carb. Res., 198: 23–28; 1990.

Jensen et al., "Resistance of SCID mice to *Candida albicans* administered intravenously or colonizing the gut: Role of polymorphonuclear leukocytes and macrophages." J. Infect. Dis., 167: 912–919; 1993.

Jobling et al., "Analysis of structure and function of the B subunit of cholera toxin by the use of site–directed mutagenesis." Molecular Microbiology, 5: 1755–1767; 1991.

Kanbe et al., "Evidence that mannans of *Candida albicans* are responsible for adherence of yeast forms to spleen and lymph node tissue." Infect. Immun., 61(6): 2578–2584; 1993.

Kanbe et al., "Evidence for adhesin activity in the acid–stable moiety of the phosphomannoprotein cell wall complex of Candida albicans." Infect. Immun., 62(5): 1662–1668; 1994.

Kanbe et al., "Evidence that *Candida albicans* binds via unique adhesion system on phagocytic cells in the marginal zone of the mouse spleen." Infect. Immun., 60: 1972–1978; 1992.

Kaneko et al., "Potentiation of host resistance against microbial infections by lentinan and its related polysaccharides." Adv. Exp. Med. Biol., 319: 201–215; 1992.

Kennedy, M.J., "Adhesion and association mechanisms of *Candida albicans*." Current Topics in Medical Mycology, 2: 73–169, 1988.

Klotz et al., "Adherence of *Candida albicans* to immobilized extracellular matrix proteins is mediated by calcium–dependent surface glycoproteins." Microbial Path., 14: 133–147; 1993.

Klotz et al., "Adherence and penetration of vascular endothelium by Candida yeasts." Infect. immun., 42(1): 374–84; 1983.

Klotz, S.A., "Fungal adherence to the vascular compartment: A Critical step in the pathogenesis of disseminated candidiasis." Clin. Infect. Dis., 14: 340–347; 1992.

Kobayashi et al., "Structural study of cell wall phosphomannan of *Candida albicans* NIH B–792 (serotype B) strain, with special reference to $^1H$ and $^{13}C$ NMR analyses of acid–labile oligomannosyl residues." Arch. Biochem. Biophys., 278(1): 195–204; 1990.

Kozel et al., "Nonencapsulated variant of *Cryptococcus neoformans*. 1. Virulence studies and characterization of soluble polysaccharide." Infect. Immun., 3: 287–294; 1971.

Kuruganti et al., "Nonspecific and Candida–specific immune responses in mice suppressed by chronic administration of anti–$\mu$." J. Leukocyte Biol., 44: 422–433; 1988.

LaForce et al., "Inhibition of leukocyte candidacidal activity by serum from patients with disseminated candidiasis." J. Lab. Clin. Med., 86; 657–666; 1975.

Lazar et al., "Transforming growth factor α: Mutation of aspartic acid 47 and leucine 48 results in different biological activities." Mol. Cell. Biol., 8(3):1247–1252; 1988.

Li et al., "Chemical definition of an epitope/adhesin molecule on *Candida albicans*." J. Biol. Chem., 268: 18293–18299; 1993.

Li et al., "A cell surface/plasma membrane antigen of *Candida albicans*." J. Gen. Microbiol., 137: 455–464; 1991.

Livingston et al., "GD3/proteosome vaccines induce consistent IgM antibodies against the ganglioside GD3." Vaccine 11(12): 1199–2004; 1993.

Maiti et al., "Role of antibodies and effect of BCG vaccination in experimental candidiasis in mice." Mycopathologia, 91: 79–85; 1985.

Marrie et al., "The ultrastructure of *Candida albicans* infections." Can. J. Microbiol., 27: 1156–1164; 1981.

Marodi et al., "Mechanisms of host defense against Candida Species. 1. Phagocytosis by monocytes and monocyte–derived macrophages." J. Imm., 146: 2783–2789; 1991.

Martinez et al., "Wall mannoproteins in cells from colonial phenotypic variants of *Candida albicans*." J. Gen. Microbiol., 136: 2421–2432; 1990.

Matsumoto et al., "Protective effect of human granulocyte colony–stimulating factor on microbial infection in neutropenic mice." Infect. Immun., 55: 2715–2720; 1987.

Matsumoto et al., "Effect of combination therapy with recombinant human granulocyte colony–stimulating factor (rG–CSF) and antibiotics in neutropenic mice unresponsive to antibiotics alone." J. Antimicrob. Chemother., 28: 447–453; 1991.

Matthews, R.C., "*Candida albicans* HSP 90: Link between protective and autoimmunity." J. Med. Microbiol., 36: 367–370; 1992.

Matthews et al., "Acquired immunity to systemic candidiasis in immunodeficient mice: Role of antibody to heat shock protein 90." J. Inf. Dis., 166: 1193–1194; 1992.

Matthews et al., "Autoantibody to heat–shock protein 90 can mediate protection against systemic candidiosis." Immunol., 74: 20–24; 1991.

Matthews et al., "Candida and AIDS: Evidence for protective antibody." Lancet, 2(8605): 263–265; 1988.

Mayer et al., "Technical report: *Candida albicans* adherence to endothelial cells." Microvascular Res., 43: 218–226; 1992.

Meunier et al., "Candidemia in immunocompromised patients." Clin. Infect. Dis., 14 (Suppl. 1): S120–S125; 1992.

Meunier, F., "Prevention of mycoses in immunocompromised patients." Rev. Infect. Dis., 9(2): 408–416; 1987.

Morrison et al. "In vitro studies of the interaction of murine phagocytic cells with *Candida albicans*." J. Reticuloendothelial Soc., 29: 23–34; 1981.

Mourad et al., "Passive immunization of mice against *Candida albicans*." Sabouraudia, 6(2): 103–105; 1968.

Mourad et al., "Active immuniztion of mice against *Candida albicans*." Proc. Soc. Exp. Biol. Med., 106: 570–572; 1961.

Muller et al., "Antibodies against defined carbohydate structures of *Candida albicans* protect H9 cells against infection with Human Immunodeficiency Virus–1 in vitro." J. Acquired Imm. Def. Syn., 4: 694–703; 1991.

Odds, F.C., *Candida and candidiasis*. Bailere Tindall, London, pp. 252–278, 1988.

Osada et al., "Stimulation of resistance of immunocompromised mice by a muramyl dipeptide analog." Infect. Immun., 37: 1285–1288; 1982.

Pearsall et al., "Immunologic responses to *Candida albicans*. III. Effects of passive transfer of lymphoid cells or serum on murine candidiasis." J. Immunol., 120: 1176–1180; 1978.

Pecyk et al., "Efficacy of Interleukin–1β against systemic *Candida albicans* infections in normal and immunosuppressed mice." Infect. Immun., 57: 3257–3258; 1989.

Poor et al., "Analysis of an in vivo model to study the interaction of host factors with *Candida albicans*." Infect. Immun., 31: 1104–1109; 1981.

Pratt et al., *Priniciples of Drug Action: The Basis of Pharmacology*, 3rd ed. (1990) p. 4–5.

Qian et al., "Elimination of mouse splenic macrophages correlates with increased susceptibility to experimental disseminated candidasis." J. Immunol., 152; 5000–5008: 1994.

Raschke et al., "Genetic control of yeast mannan structure. Isolation and characterization of mannan mutants." J. Biol. Chem., 248: 4660–4666; 1973.

Riesselman et al., "Improvements and important considerations of an ex vivo assay to study *Candida albicans*–splenic tissue interactions." J. Immunol. Methods, 145:153–160; 1991.

Rogers et al., "Immunity to experimental renal candidiasis in rats." Infect. Immun., 19: 737–740; 1978.

Romani et al., "Neutralizing antibody and interleukin 4 induces systemic protection and T helper type 1–associated immunity in murine candidiasis." J. Exp. Med. 176; 19–25; 1992.

Romani et al., "Immunoregulatory role of different T cell subsets in murine candidiasis." Pharm. Res,. 26(Supp. 2): 200; 1992.

Romani et al., "CD4+ subset expression in murine candidiasis. Th responses correlate directly with genetically determined susceptibility or vaccine–induced resistance" J. Imm., 150(3): 925–931; 1993.

Rotrosen et al., "Adherence of Candida to cultured vascular endothelial cells; Mechanisms of attachment and endothelial cell penetration." J. Infect. Dis., 152(6):1264–1274; 1985.

Rudinger J., "Characteristics of the amino acids as components of a peptide hormone sequence," *Peptide Hormones*, ed Parsons, (1976) p. 1–7.

Rustchenko–Bulgac et al., "Chromosomal rearrangements associated with morphological mutants provide a means for genetic variation of *Candida albicans*." J. Bacteriol., 172: 1276–1283; 1990.

Russell et al., "Structural features can be unconserved in proteins with similar folds. An analysis of side–chain to side–chain contacts. Secondary structure and accessibility." J. Mol. Biol., 244: 332–350; 1994.

Scheld et al., "Influence of preformed antibody on the pathogenesis of experimental *Candida albicans* endocarditis." Infect. Immun., 40(3): 950–955; 1983.

Scherer et al., "Genetics of *Candida albicans*." Microbiol. Rev., 54: 26–241; 1990.

Schlageter et al., "Opsonization of *Crytococcus neoformans* by a family of isotype–switch variant antibodies specific for the capsular polysaccharide." Infect. Immun., 58:1914–1918: 1990.

Segal et al., "Induction of protection against candidiasis in tumor–bearing mice by vaccination with *Candida albicans* ribosomes." J. Med. Vet. Mycology, 25: 355–363; 1987.

Segal, E., "Vaccines against fungal infections." Crit. Rev. Microbiol., 14: 229–271; 1987.

Segal et al., "Experimental vaccination with *Candida albicans* ribosomes in cyclophosphamide–treated animals." Sabouraudia, 19: 267–273; 1981.

Shibata et al., "Immunochemical study on the mannans of *Candida albicans* NIH A–207, NIH B–792, and J–1012 strains prepared by fractional precipitation with cetyltrimethylammonium bromide." Arch. Biochem. Biophys., 243(2): 338–48; 1985.

Shibata et al., "Characterization of phosphomannan–protein complexes isolated from viable cells of yeast and mycelial forms of *Candida albicans* NIH B–792 strain by the action of Zymolyase–100T." Arch. Biochem. Biophys., 251(2): 697–708; 1986.

Shibata et al., "Structural analysis of phospho–D–mannan–protein complexes isolated from yeast and mold form cells of *Candida Albicans* NIH A–207 serotype A strain." Carb. Res., 187: 239–253; 1989.

Sieck et al., "Protection against murine disseminated candidiasis mediated by a *Candida albicans*–specific T–cell line." Infect. Immun., 61(8): 3540–3543; 1993.

Smith, G.P., "Filamentous fusion phage: Novel expression vectors that display cloned antigens on the virion surface." Science 228: 1315–1316; 1985.

Soll, D.R., "High–frequency switching in *Candida albicans*." Clin. Mirobiol. Rev., 5: 183–203; 1992.

Steinshamn et al., "Tumor necrosis factor and interleukin–6 in *Candida albicans* infection in normal and granulocytopenic mice." Infect. Immun., 60: 4003–4008; 1992.

Su et al., "The role of macrophages in the immunoadjuvant action of liposomes: Effects of elimination of splenic macrophages on the immune response against intravenously infected liposome–associated albumin antigen." Immunol., 66: 466–470; 1989.

Sundstrom et al., "Humoral and cellular immune responses to enolase after alimentary tract colonization or intravenous immunization with *Candida albicans*." J. Inf. Dis., 170: 390–395; 1994.

Suzuki et al., "Protecting effect of chiton and chitosan on experimentally induced murine candidiasis." Micribiol. Immunol., 28: 903–912; 1984.

Tavares et al., "Immunoprotection against systemic candidiasis in mice." Int. Imm., 7(5): 785–796; 1995.

Tojo et al., "Preparation of monoclonal antibodies reactive withβ–1,2–linked oligomannosyl residues in the phosphomannan–protein complex of *Candida albicans* NIH B–792 strain." Clin. Chem., 34: 539–543; 1988.

Torosantucci et al., "Identification of a 65–kDa mannoprotein as a main target of human cell–mediated immune response in *Candida albicans*." J. Inf. Dis., 168: 427–435;1993.

Torosantucci et al., "Differences in the antigenic expression of immunomodulatory mannoprotein constituents on yeast and mycelial forms of *Candida albicans*." J. Gen. Microbiol., 136: 1421–1428; 1990.

Tripp et al., "Evidence for complement independent in vivo adherence of *Candida albicans*." Abstr. Annu. Meet. ASM., 1994.

Tokunaga et al., "Ultrastructure of outermost layer of cell wall in *Candida albicans* observed by rapid–freezing technique." J. Electron Microsc., 35: 237–246; 1986.

Van't Wout et al., "Protection of neutropenic mice from lethal *Candida albicans* infection by recombinant interleukin 1." Eur. J. Immunol., 18: 1143–1146; 1988.

Van't Wout et al., "Comparison of the efficacies of Amphotericin B., Fluconazole, and Itraconazole against a systemic *Candida albicans* infection in normal and neutropenic mice." Antimicrob. Agents Chemother., 33: 147–151; 1989.

Vannier et al., "Antibody responses to liposome–associated antigen." Immunol. Let., 19: 59–64; 1988.

Walker et al., "A serum–dependent defect of neutrophil function in chronic mucocutaneous candidiasis." J. Clin. Pathol., 33: 370–372; 1980.

Wells et al., "The chemokine information source: Identification and characterization of novel chemokines using the WorldWide Web and Expressed Sequence Tag databases." J. Leukocyte Biol., 61: 545–550; 1997.

Wetzler et al., "*Gonnococcal porin* vaccine evaluation: Comparison of Por porteosomes, liposomes, and blebs isolated from *rmp* deletion mutants." J. Inf. Dis., 166: 551–555. 1992.

Williams et al., "Protective effect of glucan in experimentally induced candidiasis." J. Reticuloendothelial Soc., 23: 479–490; 1978.

Reactivity of MAb B6.1 against PS76-carrier protein conjugates

Dots 1, 2 - normal mouse serum; Dots 3-10 - serum from peptide-immunized mice; Odd dots - IgG detection; Even - IgM detection FIG. 6 Immunization with peptide mimotopes induces anti-Candida carbohydrate antibodies in mice Absorbance = $OD_{490nm}$ (Ab+2ME extract) − $OD_{490nm}$ (Ab + irrelevant CHO)

Disseminated Candidias By Survival Time measurements. Therapeutic effect of MAb B6.1 on candidate injected mice (one hour infection)

FIG. 16 Proposed structure of the phosphomannan complex (PMC) - in this case, n-linkage to cell wall protein is shown.

C. albicans NIH B-792 strain
Shibata, et al. J. Biol. Chem 270: 1113-1995

Mass spec results dimension H-nmv of B6.1 epitope

2 - dNMR of B6.1 epitode

FIG. 21

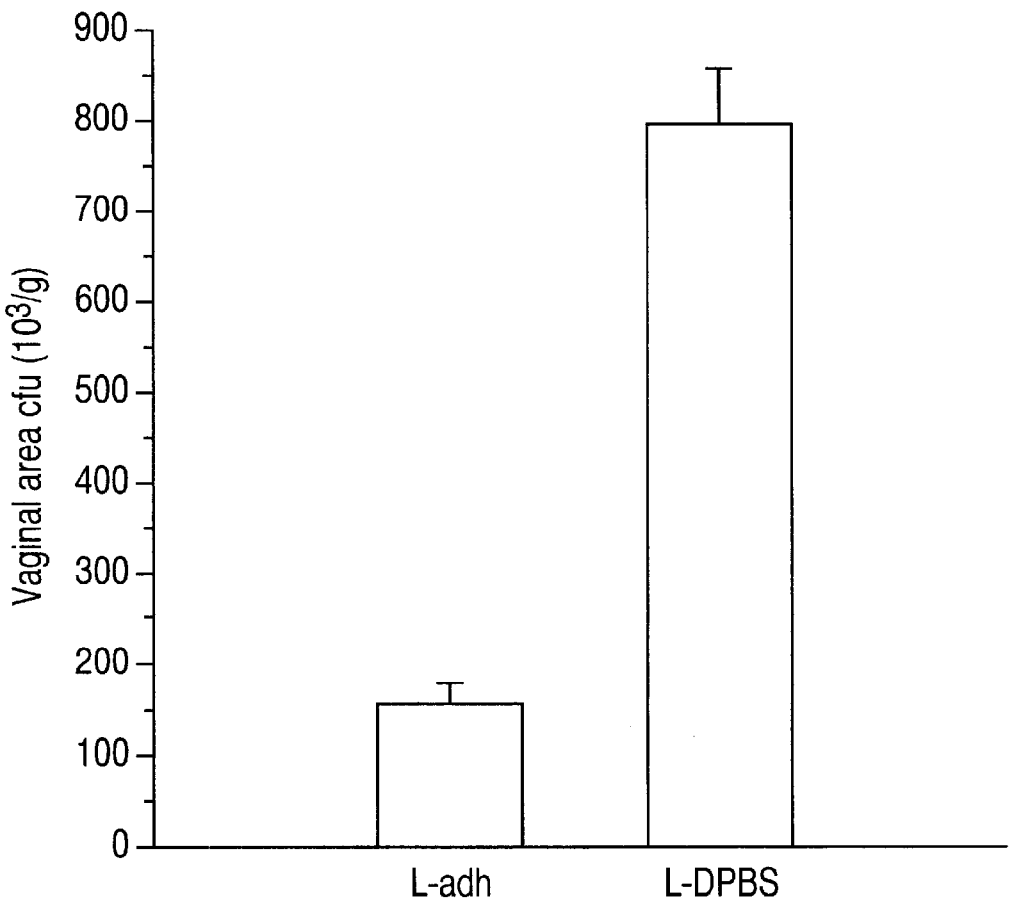

Therapeutic effect of liposome-2ME (L-adh) as a vaccine source on mice* against vulvovaginal candidiasis.

*Animals were infected with *C. albicans* one hr before vaccination.

**Mice were intravaginally infected with *Candida albicans* ($5 \times 10^5$/mouse) 1 hr before i.v. vaccine treatment. Seven days after the infection, vagina areas were collected, and cfu in the areas were measured.

*Animals were infected with *C. albicans* one hr before antibody treatment.

T=0   $5 \times 10^5 / 10 \mu l$ lvg.
T=1h  MAb B6.1 $30 \mu l$ undil 1280, 3.5 mg/ml
T=24h MAb B6.1 $10 \mu l$
T=48h cfc

SEQUENCE LISTING

```
<160> NUMBER OF SEQ ID NOS:  8

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 1

Tyr Arg Gln Phe Val Thr Gly Phe Trp
  1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 2

Pro Pro Gly Leu Tyr Trp Ser Gly Pro Pro Val Trp
  1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 3

Pro Pro Gly Trp Phe Gly Thr Val Phe Gln Arg Tyr
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 4

Pro Pro Gly Trp Tyr Gly Gly Tyr Thr Lys Tyr His
```

-continued

```
<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 5

Pro Pro Gly Trp Phe Gly Gly Thr Thr Leu Tyr Ser
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 6

Ser Trp Tyr Glu Gly Leu Arg Leu Ile Gly Pro Pro
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:
      polysaccharide epitope mimic

<400> SEQUENCE: 7

Tyr Arg Gln Phe Val Thr Gly Phe Trp Gly Pro Pro Cys
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:
      polysaccharide epitope mimic
<223> OTHER INFORMATION: X at positions 1, 4, 8, 9 = Phe, Trp or Tyr; X
      at positions 2 and 3 can be any amino acid; X at position 5 = Ser,
      Thr or Gly but may be absent; X at positions 6 and 7 = Ser, Thr or
      Gly.

<400> SEQUENCE: 8

Xaa Xaa Xaa Xaa Xaa Xaa Xaa Xaa Xaa
 1               5
```

PEPTIDES WHICH MIMIC CANDIDA CARBOHYDRATE EPITOPES AND THEIR USE IN A VACCINE

This application is a divisional of application Ser. No. 09/076,883, filed May 13, 1998, which is a continuation-in-part of application Ser. No. 08/756,014, filed Nov. 25, 1996, now abandoned which is a continuation-in-part of application Ser. No. 08/483,558 (now U.S. Pat. No. 5,578,309), filed Jun. 7, 1995, which is a continuation-in-part of application Ser. No. 08/247,972 (now abandoned), filed May 23, 1994. This application also claims priority to PCT/US97/21661, filed Nov. 25, 1997, which claims priority to U.S. Provisional No. 60/045,030, filed Apr. 28, 1997 and U.S. Provisional No. 60/046,299, filed May 13, 1997, herein incorporated by reference in their entireties.

TECHNICAL FIELD

The present invention relates to peptides which mimic carbohydrate epitopes (mimotopes) of Candida and to a vaccine comprising the peptide or polynucleotides encoding the peptide mimotopes or antibodies to the peptides and a method for the treatment of disseminated candidiasis due to infection by Candida albicans.

BACKGROUND OF THE INVENTION

Candida albicans is a fungus responsible for various forms of candidiasis, a condition which may be found in normal and immunocompromised patients, such as those with acquired immune deficiency syndrome. Humans and mice who are neutropenic are especially at risk of developing disseminated candidiasis (Denning, D. W., et al. 1992. Antifungal prophylaxis during neutropenia or allogeneic bone marrow transplantation: what is the state of the art? Chemotherapy 38(suppl 1):43–49; Matsumoto, M. S., et al. 1991. Effect of combination therapy with recombinant human granulocyte colony-stimulating factor (rG-CSF) and antibiotics in neutropenic mice unresponsive to antibiotics alone. J. Antimicrob. Chemother. 28:447–453; Meunier, F. 1987. Prevention of mycoses in immunocompromised patients. Rev. Infect. Dis. 9:408–416; Meunier, F., et al. 1992. Candidemia in immunocompromised patients. Clin. Infect. Dis. 14 (Suppl 1):S120–S125; and Van't Wout, J. W. et al. 1989. Comparison of the efficacies of amphotericin B, Fluconazole, and Itraconazole against a systemic Candida albicans infection in normal and neutropenic mice. Antimicrob. Agents Chemother. 33: 147–151).

Several attempts have been made in the prior art to achieve immunostimulating compounds for the treatment of candidiasis as evidenced below.

U.S. Pat. No. 5,288,639 to Bernie et al. discloses the use of antibodies specific for stress proteins of C. albicans for the treatment of systemic candidiasis. Bernie et al. isolated a 47 kilo-dalton immunodominant antigen from C. albicans and found that serum from patients with systemic candidiasis reacts with the antigen. Monoclonal antibodies raised against the fungal stress proteins produced a 33% survival at 24 hours in animals challenged with a lethal dose of the C. albicans.

U.S. Pat. No. 4,397,838 to d'Hinterland discloses preparations of purified proteoglycans extracted from bacterial membranes. The proteoglycans serve as immunoadjuvants and have an immunostimulating activity without being immunogenic themselves. They are useful in serving as adjuvants with ribosomal vaccines such as a vaccine containing the ribosomes of C. albicans.

U.S. Pat. No. 4,310,514 to Durette et al. discloses immunologically active dipeptidyl 5-O, 6-O-acyl-2-amino-2-deoxy-D-glucofuranose derivatives. The compounds are used to delay the release of an antigen and stimulate the immune response of the host in conjunction with a vaccine. Compounds of Durette provide non-specific host protection against infectious organisms such as C. albicans.

U.S. Pat. No. 4,315,913 to Durette discloses immunologically active dipeptidyl 2-amino-1,2-dideoxy-D-glucose derivatives. These derivatives are also useful as immunological adjuvants and themselves provide nonspecific host protection against C. albicans.

U.S. Pat. No. 4,368,910 to Shen et al. is directed to immunologically active dipeptidyl 4-O-6-O-acyl-2 amino-2-deoxy-D-glucose derivatives. These derivatives are indicated to be useful as immunogenic agents and vaccines and by themselves provide non-specific host protection against infectious organisms such as C. albicans.

U.S. Pat. No. 4,323,560 to Baschang et al. is directed to phosphorylmuramyl peptides. The peptides are used to stimulate immunity. The compounds of Baschang et al. have been found to be inhibitive to infections caused by fungi such as C. albicans.

U.S. Pat. No. 5,032,404 to Lopez-Berestein et al. disclose a liposomal agent for treating disseminated fungal infection in an animal. Because of the nature of polysaccharide fungal cell walls, it is expected that all medically important fungi activate complement. The patent indicated that there is a positive correlation between animals deficient in late-acting complement components and increased susceptibility to fungi such as C. albicans. The patent indicates that disseminated fungal infection can be treated with liposomal agent comprised of lipids, a polyene macrolide anti-fungal compound and cholesterol. Lipids can include phosphatidyl choline. Liposomes incorporate an effective amount of a polyene macrolide anti-fungal compound such as hamycins or lucensomycin, filipin, lagosin and natamycin.

U.S. Pat. No. 4,678,748 to Sutka et al. discloses a process for the production of the immunobiological preparations applicable in the diagnosis, prevention and treatment of Candida guilliermondii infections. Strains of C. guilliermondii are killed and used to formulate a vaccine.

Early attempts at obtaining compounds which provide non-specific host protection against C. albicans are generally in the form of immuno adjuvants used in conjunction with vaccines.

More specific vaccine approaches include targeting aspects of C. albicans pathogenesis. An important aspect of pathogenesis is adherence of C. albicans to host tissue. Discussion below provides an understanding of adherence as it relates to pathogenesis of disseminated candidiasis. C. albicans is an organism that may show considerable variability of certain characteristics. Genetics studies show that the organism is diploid, but apparently without the ability to undergo meiosis, yet it has impressive genetic variability between and within strains (Scherer, S. et al. 1990. Genetics of C. albicans. Microbiol. Rev. 54:226–241). Chromosomal aberrations unpredictably occur (Rustchenko-Bulgac et al. 1990. Chromosomal rearrangements associated with morphological mutants provide a means for genetic variation of C. albicans. J. Bacteriol, 172:1276–1283), and may be related to high frequency phenotypic (colony) changes in some strains (Soll, D. R. 1992. High-frequency switching in C. albicans. Clin. Microbiol. Rev. 5:183–203). Perhaps related to the genetic instability are findings that strains of C. albicans variably express cell surface antigens (Cutler, J. E., et al. 1994. Antigenic variability of *C. albicans* cell surface. Curr. Top. Med. Mycol. 5:27–47, and Martinez, J. P., et al. 1990. Wall mannoproteins in cells from colonial phenotypic variants of *C. albicans*. J. Gen. Microbiol. 136:2421–2432). Some of these antigens include putative virulence factors such as adhesions and enzymes (Cutler, J. E. 1991. Putative virulence factors of *C. albicans*. Ann. Rev. Microbiol. 45:187–218).

Studies on adherence properties of *C. albicans* are important in gaining an understanding of *C. albicans* interactions with its host. The ability to bind to mucus and epithelial surfaces likely plays a critical role in maintaining *C. albicans* at these locations. The fungus also shows adherence specificities for selected populations of splenic and lymph node macrophages (Cutler, J. E., et al. 1990. Characteristics of *C. albicans* adherence to mouse tissue. Infect. Immun. 58:1902–1908; Han, Y., et al. 1993. Binding of *C. albicans* yeast cells to mouse popliteal lymph node tissue is mediated by macrophages. Infect. Immun. 61:3244–3249; and Kanbe, T., et al. 1992. Evidence that *C. albicans* binds via a unique adhesion system on phagocytic cells in the marginal zone of the mouse spleen. Infect. Immun. 60:1972–1978), and extracellular matrix proteins (ECM) and endothelial cells (Filler, S. G., et al. 1991. *C. albicans* stimulates endothelial cell eicosanoid production. J. Infect. Dis. 164:928–035; Klotz, S. A. 1992. Fungal adherence to the vascular compartment: A critical step in the pathogenesis of disseminated candidiasis. Clin. Infect. Dis. 14:340–347; Mayer, C. L., et al. 1992. Technical report: *C. albicans* adherence to endothelial cells. Microvascular Res. 43:218–226; Rotrosen, D. et al. 1985. Adherence of Candida to cultured vascular endothelial cells: mechanisms of attachment and endothelial cell penetration. J. Infect. Dis. 153:1264–1274).

The fungal adhesions range in properties from hydrophilic to hydrophobic molecules (Hazen, K. C. 1990. Cell surface hydrophobicity of medically important fungi, especially Candida species, p. 249–295. In R. J. Doyle and M. Rosenberg (ed.), Microbial Cell Surface Hydrophobicity. American Society of Microbiology, Washington; Kennedy, M. J. 1988. Adhesion and association mechanisms of *C. albicans*. Curr. Top. Med. Mycol. 2:73–169) and all may be mannoproteins (8, 11). Both mannan and protein moieties may function as adhesions.

Some adhesions have integrin-like activity in that they act as receptors for mammalian proteins such as iC3b, fibronectin, laminin and fibrinogen; one adhesion has lectin-like activity; and a C3d receptor has been described (Bendel, C. M., et al. 1993. Distinct mechanisms of epithelial adhesion for *C. albicans* and *Candida tropicalis*. Identification of the participating ligands and development of inhibitory peptides. J. Clin. Invest. 92:1840–18492; Calderone, R. A., et al. 1991. Adherence and receptor relationships in *C. albicans*. Microbiol Rev. 55:1–20; Cutler, J. E. 1991. Putative virulence factors of *C. albicans*. Ann. Rev. Microbiol. 45:187–218; Gilmore, B. J., et al. 1988 An iC3b receptor on *C. albicans*: structure, function, and correlates for pathogenicity. J. Infect. Dis. 157:38–46; Klotz, S. A., et al. 1993. Adherence of Candida to immobilized extracellular matrix proteins is mediated by *C. albicans* calcium-dependent surface glycoproteins. Microbiol. 14:133–147). The surface of hydrophilic yeast cells of *C. albicans* has a fibrillar appearance both in vitro and in vivo (Hazen, K. C. et al. 1993. Surface hydrophobic and hydrophilic protein alterations in *C. albicans*. FEMS Microbiol. Lett. 107:83–88; Marrie, T. J., et al. 1981. The ultrastructure of *C. albicans* infections. Can. J. Microbiol. 27:1156–1164; and Tokunaga, M. et al. 1986. Ultrastructure of outermost layer of cell wall in *C. albicans* observed by rapid-freezing technique, J. Electron Microsc. 35:237–246).

A major component that makes up the fibrils on the cell surface of *C. albicans* and extends deeper into the cell surface appears to be the phosphomannoprotein (PMP). The cell surface is probably more complex than this, as additional proteins with relatively small amounts of carbohydrate may also be present (Hazen, K. C., et al. 1994. Hydrophobic cell wall protein glycosylation by the pathogenic fungus *C. albicans*. Can. J. Microbiol. 40:266–272). It is not clear, however, if these proteins differ from the major PMP or are the same proteins, but with a truncated version of the glycan portion.

The present inventors have overcome the deficiencies and inability of the prior art to obtain a vaccine against disseminated candidiasis by directing their attention to a composition comprising *C. albicans* adhesions.

DISCLOSURE OF THE INVENTION

Accordingly, an object of the present invention is to provide a vaccine for treatment of candidiasis comprising a pharmaceutically effective amount of peptides that are specific structural mimics (mimotopes) or epitopes specific to the mannan portion of the phosphomannan complex of Candida which elicits an immune response.

In a preferred embodiment the peptide is a nonapeptide with the amino acid sequence (SEQ ID NO:1) where: Y, tyrosine; R, arginine; Q, glutamine; F, phenylalanine; V, valine; T, threonine; G, glycine; W, tryptophan.

In an alternative embodiment of the invention the peptide, which has a consensus amino acid sequence for peptides with reactivity to MAb B6.1, selected from the group consisting of, ArXXAr (Z) ZZArAr; where: Ar, aromatic amino acid (F, W or Y); X, any amino acid; Z, equals S, (where S, serine), T or G; (Z), is S, T, or G which may or may not be present.

The invention also encompasses a vaccine wherein polynucleotide sequences encoding the peptide mimotope are delivered in an appropriate vaccine vector at pharmaceutical effective amounts for the treatment of candidiasis.

In a preferred embodiment of the invention, the polynucleotides are comprised of DNA coding for the peptide mimotopes and delivered in a DNA vaccine vector at pharmaceutical effective amounts for the treatment of candidiasis.

In an alternative embodiment of the invention, the polynucleotide vaccine comprises a DNA construct coding for a consensus amino acid sequence for peptides with reactivity to MAb B6.1, selected from the group consisting of, ArXXAr(Z)ZZArAr; where: Ar, aromatic amino acid (F, W, or Y); any amino acid; Z, equals S (where S, serine), T or G; (Z), is S, T, or G which may or may not be present.

The invention also encompasses a vaccine wherein the mannan active portion comprises a composition structure selected from the group consisting of β-1,2-linked straight chain tri, tetra- and penta-mannosyl residues in the acid labile part of the mannan portion of the phosphomannan complex.

Still another object of the invention provides a vaccine for treatment of disseminated and mucocutaneous Candidiasis comprising a pharmaceutical effective amount of an epitope of Candida Albicans comprising a beta 1,2-trimannose or acid stable epitopes that elicit an immune response.

The invention provides isolated protective antibodies for passive protection against hematogenous disseminated candidiasis and mucocutaneous candidiasis. The antibodies may be monoclonal antibodies specific for mannan epitopes in the acid stable portion of the mannan epitope and β-1,2-linked tri, tetra- and penta-mannosyl residues in the acid labile part of the mannan portion of the phosphomannoprotein complex.

The invention also encompasses a vaccine wherein the mannan active portion comprises a composition structure selected from the group consisting of β-1,2-linked straight chain tri, tetra- and penta-mannosyl residues in the acid labile part of the mannan portion of the phosphomannan complex.

Still another object of the invention provides a vaccine for treatment of disseminated and mucocutaneous Candidiasis comprising a pharmaceutical effective amount of an epitope of *Candida Albicans* comprising a beta 1,2-trimannose or acid stable epitopes that elicit an immune response.

The invention also encompasses a vaccine for treatment of disseminated candidiasis comprising a pharmaceutical effective amount of a peptide mimotope specific for *Candida albicans* epitopes, either β1,2-linked oligomannose or acid stable epitopes in the phosphomannan complex, or a vaccine comprised of polynucleotide sequences to code for said peptide, that elicit an immune response.

Still another embodiment provides a therapeutic composition for treatment of disseminated candidiasis comprising a pharmaceutical effective amount of passive humoral antibodies directed against a peptide mimotope specific for the β1,2-trimannose or others epitopes in the acid stable and acid labile regions of the mannan portion of the phosphomannan complex of *Candida albicans* that elicits an immune response. Also provided are isolated protective antibodies for passive protection against hematogenous disseminated candidiasis and mucocutaneous candidiasis.

The invention advantageously provides a method for the treatment of disseminated candidiasis and mucocutaneous candidiasis comprising administering an effective amount of the monoclonal antibodies of the invention to provide protection.

Still another embodiment provides a method for immunization against candidiasis comprising generating *Candida albicans* peptide mimotopes specific for phosphomannan complex-neutralizing antibodies.

Finally the invention provides a peptide mimotope specific to the mannan portion of the phosphomannan complex of candidiasis wherein said peptide has the amino acid sequence YRQFVTGFW; (SEQ ID NO: 1) where: Y, tyrosine; R, arginine; Q, glutamine; F, phenylalanine; V, valine; T, threonine; G, glycine; W, tryptophan, or function equivalents of said peptide. In a preferred embodiment the peptide has a consensus sequence of amino acids selected from the group consisting of, ArXXAr(Z)ZZArAr; where: Ar, aromatic amino acid (F, W, or Y); X, any amino acid; Z, equal S (S, serine), T or G; (Z) is S, T or G which may or may not be present.

The above and other objects of the invention will become readily apparent to those of skill in the relevant art from the following detailed description, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF THE FIGURES

FIG. 21 (4) shows the protective or prophylactic effect of the liposome-2ME extract (L-2ME) as a vaccine against disseminated candidiasis. Mice were vaccinated with the L-2ME, with liposomes alone (L-PBS) or buffer alone (PBS), then challenged i.v. with various doses of *C. albicans*.

STATEMENT OF DEPOSIT

Figure 1:
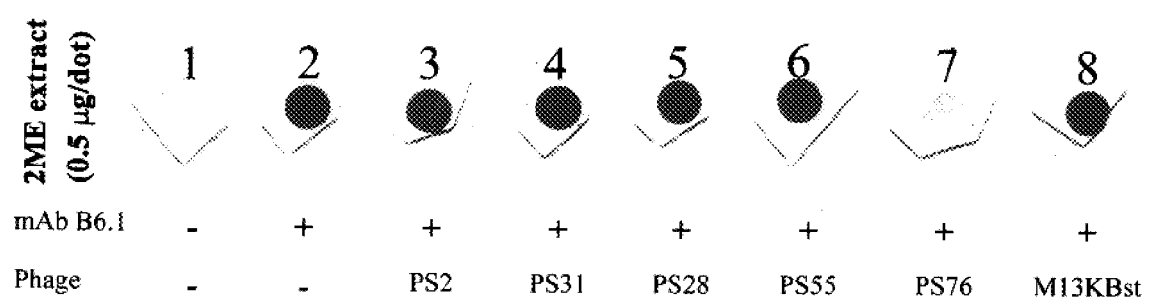
FIG. 1 shows phage-displayed, peptide mimotopes inhibition of MAb B6.1 binding to the β-1,2-linked trimannose epitope present in 2 ME extracts of *C. albicans*. MAb B6.1 at 5 ng/ml was pre-incubated with the affinity selected phage clones PS76, PS2, PS31, PS28, PS55 or with the parent phage, M13KBst ($3.5 \times 10^{12}$ plaque forming units [pfu] per ml) and added to pre-blocked Candida 2ME extract dots. Two of the phage clones, PS76 and PS2, gave moderate to strong inhibition of MAb B6.1 binding to the extract. Inhibition was dose dependent, as similar assays performed with $2 \times 10^{12}$ pfu/ml demonstrated only moderate inhibition by PS76 and weak inhibition by PS2.

Monoclonal Antibody B6.1 (930610) was deposited under the terms of the Budapest Treaty on Jun. 7, 1995 with the American Type Culture Collection, 12301 Parklawn Drive, Rockville, Md., USA. ATCC Accession No. HB11925.

DESCRIPTION OF THE INVENTION

Monoclonal antibody, MAb B6. 1, enhances resistance of mice against hematogenous disseminated candidiasis (Han and Cutler. 1995. Infect. Immun. 63:2714–2719) and against *Candida vaginitis*. MAb B6.1 is specific for a β-1,2-trimannose carbohydrate moiety that is phosphodiester linked to the other mannan complexes, all of which are part of the phosphomanno-protein complex expressed on or near the surface of *C. albicans* yeast cells.

By use of Ab-affinity chromatography and a phage display peptide library (PDPL), made by James Burritt and Clifford Bond, a family of peptides that are recognized by MAb B6.1 has been defined. Each of these peptides is nine amino acids in length and are referred to as nonapeptides. Each nonapeptide that appears to mimic a carbohydrate epitope, as evidenced by reactivity with MAb B6.1, is referred to as a mimotope. A model example of one mimotope is PS76p and its amino acid sequence is given below.

As shown below, PS76p induces an antibody response in mice and the antibodies react with whole yeast cells of *C. albicans*, and with a β-mercaptoethanol extract (2ME extract) of the fungus. The 2-ME extract contains the phosphomannoprotein complexes. By examination of several peptides that are recognized by MAb B6.1, a generalized formula for peptides is given that may serve in the formulation of a protective vaccine against various forms of candidiasis.

EXAMPLE 1

Selection of mimotopes. Sepharose 4 B (CL4B-200, Sigma) was activated with CNBr and coated with either the IgM antibody MAb B6.1 (3 mg per ml packed beads) or with an irrelevant IgM MAb control. The irrelevant IgM (from S. Pincus, MSU) was designated S10 and is specific for a protein antigen of group B streptococcus. Ab-coated beads were washed and tested for functional activity by demonstrating their ability to form Candida yeast cell rosettes with B6.1-Sepharose, but not with S10-Sepharose. The affinity matrices were pre-blocked in phosphate buffered saline (PBS) plus 1% bovine serum albumin (BSA) prior to incubation with the PDPL.

To remove phage that display nonapeptides reactive is with IgM epitopes outside of the antibody combining site, the PDPL was reacted first with the S10 affinity matrix. An aliquot of the nonapeptide PDPL (approx. $7.5 \times 10^{11}$) phage or 1500 redundants of each nonpeptide represented in the library) was diluted in phage buffer (50 mM Tris-HCl, pH 7.5, 150 mM NaCl, 0.5% v/v Tween-20 and 0.1% BSA) and incubated with S10-Sepharose in a small polystyrene tube (16 h, 4° C., with gentle rotation). The mixture was transferred to a small polystyrene column and the non-adsorbed phage were recovered in the void volume and from the 50 ml phage buffer wash by precipitation with 0.15 vol of 16.5% polyethylene glycol (PEG), 3.3 M NaCl. The S10 matrix was regenerated and blocked in PBS +1% BSA. S10 preadsorption of the library was repeated three more times until the number of S10 adsorbent phage decreased substantially (by a factor of $10^5$).

To obtain the peptide mimotopes, the remaining PDPL (i.e, those phage that did not react with S10) were reacted with the MAb B6.1 affinity matrix and clones reactive with MAb B6.1 were obtained as follows. The preadsorbed PDPL (about 2 ml at $4.62 \times 10^{10}$ pfu/ml) was incubated with MAb B6.1-Sepharose beads (16 h, 4° C.), transferred to a column and non-adherent phage were removed by extensive washing with phage buffer. Bound phage were eluted in 2 ml 0.1 M glycine buffer, pH 2.2 and the pH immediately neutralized. A few microliters of the eluted phage were removed for phage titering and the remaining phage were mixed with "starved" *E. coli* K91 for amplification. The infected cells were incubated briefly in Luria broth (LB) plus 0.75 µg kanamycin (kan)/ml and spread onto LB agar containing 75 µg kan/ml (LBkan) for overnight growth. Colonies were scraped from the LBkan surface into Tris-buffered saline (TBS) and centrifuged to obtain the phage-rich supernatant fluid. Phage were precipitated and recovered by centrifugation. Half of the amplified phage were diluted in phage buffer and incubated with a fresh aliquot of the MAb B6.1-Sepharose for a second round of affinity selection. The eluted phage were titered and amplified as above, and half were subjected to a third round of selection with fresh MAb B6.1-Sepharose.

Results show that 0.008% of the input phage from the preadsorbed PDPL were selected in the first round of MAb B6.1 selection. This number (20-fold less than if the PDPL was not preadsorbed on an S10 affinity matrix) indicates that our preadsorption removed nonparatope specific clones, which should enhance the chances of isolating MAb B6.1-specific PDPL clones. The observed increase in elution titer with each successive round of selection indicated that the Ab selection and amplification provides enrichment of MAb B6.1-reactive clones with each round. DNA sequencing and western blot analysis on the third selection pool of phage was done for further analysis.

EXAMPLE 2

Analysis of the MAb B6.1 selected phage clones. The third selection pool of phage was analyzed initially by random sequencing of phage clones, and then by a plaque lift step before sequencing as follows. An appropriate dilution of phage pool was plated, and single plaques were randomly isolated and stored individually in phage buffer. Phage minipreps were prepared in LBkan broth and harvested to provide single-stranded template DNA for sequencing with Sequenase 2.0 (USB/Amersham). The phage templates were primed with a gene III specific primer which anneals approximately 50 nucleotides (nt) from the 27-mer insert that codes for the nonapeptide expressed on the end of the pIII protein of each phage. From the randomly selected phage, 29 of the 60 phage clones exhibited non-apeptide sequences that were unique, but had areas of homology with each other. Importantly, these 29 phage clones reacted in dot blot analysis with MAb B6.1, but not with the other control IgM MAbs B6 or S10. The other 31 phage clones displayed nonapeptide sequences with the common IgM binding motif that is not associated with the paratope (antibody combining site) on MAb B6.1.

In order to identify additional clones reactive with only MAb B6.1, duplicate plaque lifts were prepared from plates containing well-separated phage from the third selection pool. The NCM filters were incubated with either MAbs S10 or B6.1, aligned and compared, and MAb B6.1 positive plaques excised from the plates and prepared for DNA sequencing. The results as shown in Table 1 indicate that the MAb B6.1 -specific clones (n=54) were represented by five unique nonapeptide displays in the PDPL. A type clone (PS2, PS76, PS31, PS28, and PS55) is designated for each of the five displays. Aromatic amino acids appear in bold text, and the P-P-G carboxy-terminal region of the pIII protein in the M13KBst construct has been included to show the orientation of the displayed nonapeptides from the clones (Table 1). Thus, PS2, PS76, PS31 and PS28 in Table 1 correspond to SEQ ID NOs:2–5, displayed from the carboxy-terminal P-P-G of the pIII protein to the amino-terminal amino acid of each peptide sequence. PS55 corresponds to SEQ ID NO:6, displayed from the amino-terminal amino acid to the carboxy-terminal P-P-G of the pIII protein.

TABLE 1

Peptide Sequences from MAb B6.1 Reactive PDPL Clones

| Type of Clone | No. out of 54 clones | Peptide Sequence from MAb B6.1-reactive PDPL clones | | | | | | | | | | |
|---|---|---|---|---|---|---|---|---|---|---|---|---|
| PS2  | 8  | P | P | G | L | Y | W | S | G | P | P | V | W |
| PS76 | 4  |   | P | P | G | W | F | G | T | V | F | Q | R | Y |
| PS31 | 38 |   | P | P | G | W | Y | G | G | Y | T | K | Y | H |
| PS28 | 2  |   | P | P | G | W | F | G | G | T | T | L | Y | S |
| PS55 | 2  |   |   | S | W | Y | E | G | L | R | L | I | G | P | P |

To determine the MAb B6.1-binding specificity of phage clones shown in Table 1, an enzyme linked immunosorbent assay (ELISA) was performed. Briefly, microtiter plate wells were coated with 1.0 μg MAb B6.1 or irrelevant IgM MAbs, B6 and S10. Wells were blocked 2 h, room temperature (RT) in Tris-buffered saline containing 5% skim milk, 0.5% Tween 20, and 1% bovine serum albumin (BLOTTO/TBST/BSA). Block was utilized as the diluent for phage additions and for the primary and secondary antibodies. Wells were washed twice with TBS, and varying amounts of phage (e.g. $10^{11}$, $10^{10}10^9$, and $10^8$) were added to wells in a 100 μl volume. Plates were covered and incubated 2–4 h, RT. Plates were washed 3× with TBS+0.1% Tween 20 (TBST) and 3× with TBS. Primary antibody, either 1:30,000 rabbit anti-M13 KBst antiserum (a kind gift from Al Jesaitus, Montana State University) or 1:5000 HRP-conjugated sheep anti-M13 antiserum (Pharmacia Biotech, Cat #27-941101), was added and plates incubated 2–4 h, RT, or o/n at 4° C. Plates were washed 3× in TBST, 3× in TBS. Assay plates receiving the rabbit anti-M13 antiserum were incubated with 1:5000 HRP-conjugated goat anti-rabbit antibody for 2–4 h, RT, and washed as above. Substrate solution containing o-phenylenediamine, $H_2O_2$, in 0.1 M sodium citrate buffer pH 5.0 was added and color developed 10–30 min. Reactions were stopped by addition of 10% $H_2SO_4$ and absorbances read at $OD_{490bnm}$ with a microplate reader (BioRad, Hercules, Calif.).

ELISA results, shown in Table 2, demonstrate that phage clones PS76, PS2, PS31, PS28, and PS55 bind specifically to MAb B6.1 and not to the irrelevant antibodies. Two control reactions were included: M13KBst, the parent vector for the PDPL, does not bind any of the MAbs; whereas phage clone edi demonstrates the activity of phage clones that bind to many different IgM antibodies.

TABLE 2

Specificity of phage-displayed peptide mimotopes for binding to MAb B6.1. Absorbance values are the mean of triplicate wells, ± standard deviation

| Phage sample | Wells Coated with MAb or block only | | | |
|---|---|---|---|---|
| | block | MAb B6.1 | MAb B6 | MAb S10 |
| PS76 | 0.025 ± 0.002 | 1.732 ± 0.225 | 0.113 ±0.020 | 0.142 ± 0.046 |
| PS2 | 0.011 ± 0.006 | 1.334 ± 0.443 | 0.031 ± 0.002 | 0.068 ± 0.011 |
| PS31 | 0.012 ± 0.001 | 1.154 ± 0.040 | 0.055 ± 0.010 | 0.076 ± 0.015 |
| PS28 | 0.011 ± 0.003 | 1.454 ± 0.300 | 0.022 ± 0.004 | 0.065 ± 0.006 |
| PS55 | 0006 ± 0.001 | 0.945 ± 0.157 | 0.027 ± 0.005 | 0.041 ± 0.008 |
| M13KBst | 0.007 ± 0.002 | 0.021 ± 0.006 | 0.014 ± 0.001 | 0.032 ± 0.002 |
| edl | 0.005 ± 0.002 | 2.360 ± 0.128 | 2.477 ± 0.040 | 2.341 ± 0.139 |
| block only | 0.006 ± 0.005 | 0.018 ± 0.005 | 0.019 ± 0.002 | 0.035 ± 0.010 |

EXAMPLE 3

Evidence that the selected clones/peptides react with the MAb B6.1 binding site. Three different inhibition formats were used to test for phage/peptide reactivity with the MAb B6.1 binding site.

One liter cultures of each selected phage clone and the parent M13KBst phage (as a control) were harvested and the phage titers determined. Phage-coated latex bead samples for PS76, PS2, PS31, and M13KBst (control) which agglutinated strongly with a rabbit anti-M13 phage polyclonal antiserum (a gift from A. Jesaitis, MSU) were prepared, but MAb B6.1 did not agglutinate any of the phage-latex bead conjugates. Given the small copy number (five) and the end orientation of pIII proteins by M13, this result was not surprising.

Various concentrations of the harvested phage were assayed for their ability to inhibit agglutination by either MAb B6.1-coated latex beads and soluble 2-ME extract, or 2-ME extract-coated latex beads and MAb B6.1 were tested. This approach was also unsuccessful. Since the pIII protein is a minor surface molecule on the phage particle, we calculate that an inhibition may require a minimum of $10^{14}$ phage particles which makes this approach untenable.

Two immunoblot-dot assays were examined. These assays provide the necessary sensitivity to screen phage clones by inhibition. Each of the dot blot inhibition assays provide different information about the candidate peptides. Method one identifies which peptides compete well with 2-ME extract for binding to MAb B6.1, and method two confirms that lower affinity binding clones actually interact with the antibody combining site.

Method 1:

Inhibition of MAb B6.1 binding to blotted 2-ME extract by intact phage. To determine the sensitivity, dot blots of 2-ME extract (0.5 μg/dot on nitrocellulose) were blocked in phage buffer, and surveyed with different concentrations of MAb B6.1 (from 0.001–20 μg Ab/ml). The secondary Ab was a 1:1000 dilution of alkaline phosphatase conjugated goat anti-mouse μ-chain specific Ab (Sigma A-9688). This method allowed for detection of MAb B6.1 at 0.005 μg MAb/ml, which was chosen for the phage inhibition studies. MAb B6.1 at 5 ng/ml was preincubated (1 h, 22–24 C, gentle agitation) with the various selected phage clones or with the parent phage, M13KBst ($3.5 \times 10^{12}$ pfu of each clone/ml). The Ab/phage mixture was added to pre-blocked 2-ME extract dots in separate tubes and incubated overnight at 4° C. Blots were washed, incubated with secondary antibody for 4 h, and washed in Tris/NaCl/$MgCl_2$ buffer (pH 9.5) and immersed in nitroblue tetrazolium/5-bromo-4-chloro-3-indolyl phosphate. Using this approach we found that two of the phage clones, PS76 and PS2 gave moderate to strong inhibition of MAb B6.1 binding to the blotted 2-ME extract, as shown in FIG. 1. Inhibition by the phage clones was dose dependent, as similar assays performed with $2 \times 10^{12}$ pfu/ml demonstrated only moderate inhibition by phage clone PS76 and weak inhibition by PS2. M13KBst-containing solutions did not inhibit antibody binding indicating that parent viral proteins are not responsible for the inhibition activity shown by PS76 and PS2. Lack of inhibition by clone PS31 may indicate lower binding affinity to antibody than 2-ME extract.

Figure 2:
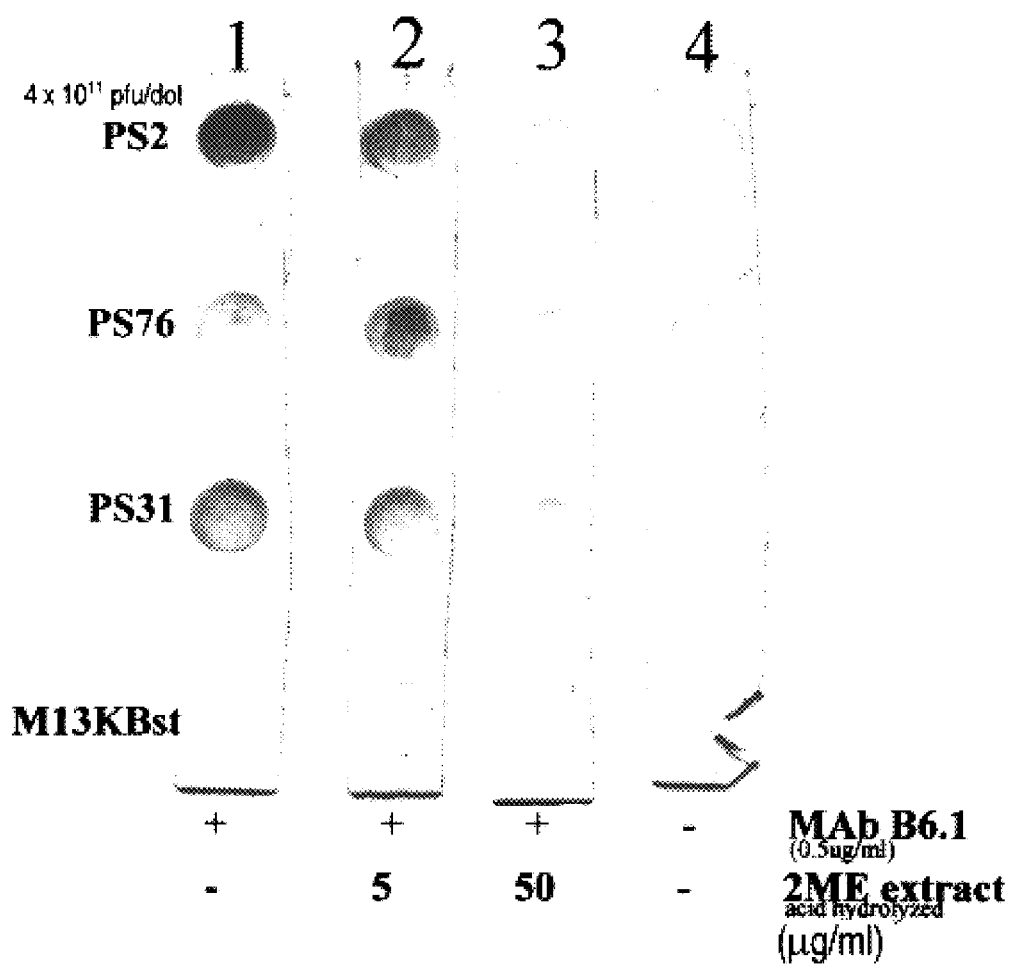
FIG. 2 shows *C. albicans* 2 ME extract inhibition of MAb B6.1 binding to the phage-displayed peptide mimotopes. Phage ($4 \times 10^{11}$ pfu per dot) were applied to nitrocellulose, blocked and incubated with pre-mixed solutions of MAb B6.1 (0.5 μg MAb/ml) in block alone or block containing 5 or 50 μg/ml of acid-hydrolyzed 2ME extract. Dot blots were washed and incubated with enzyme-conjugated secondary antibodies for detection. The carbohydrate epitope of MAb B6.1 blocked binding of the antibody to the phage clones.

Method 2:

Inhibition of MAb B6.1 binding to phage dot blots by soluble 2-ME extract. MAb B6.1-selected phage clones PS2, PS76, PS31 and the parent control phage M13KBst were prepared at various concentrations and dot blotted onto nitrocellulose (pfu per dot ranged from $2 \times 10^{10}$ up to $8 \times 10^{10}$) to determine the sensitivity of immunoblot detection with MAb B6.1 (0.5 μg Ab/ml phage buffer) and with a 1:1000 dilution of secondary antibody as above. Phage dots with $4 \times 10^{11}$ pfu were chosen. The clones were applied to nitrocellulose and preblocked in phage buffer. In separate tubes, MAb B6.1 was mixed with the 2-ME extract at 5 or 50 μg carbohydrate/ml. For inhibition studies done with soluble reactants, we used acid-hydrolyzed 2-ME extract to free the B6.1 epitope from the remainder of the PM molecule in order to reduce the possible stearic hindrance preventing an inhibition from taking place. The pre-blocked phage dots were added to the various solutions of antibody with or without extract and incubated overnight, 4° C. The blots were washed, incubated in alkaline phosphatase-labeled secondary antibody and detection was done as described above. The 2-ME extract at 50 µg/ml inhibited binding of antibody to all the phage clones, as shown in FIG. 2. This inhibition was dose dependent, as the lower concentration of extract (5 µg/ml) did not inhibit as much as the higher concentration. No antibody bound to the M13KBst parent phage. Phage clones PS55 and PS28 samples are currently being tested in similar assays.

Results from dot blot studies with various phage clones demonstrate that affinity selected phage will inhibit the interaction of MAb B6.1 with PM.

EXAMPLE 4

Synthetic peptide inhibits binding of MAb B6.1 to its' carbohydrate epitope. On the basis of inhibition studies with intact phage clones, the nonapeptide displayed by phage clone PS76 was chosen for synthesis and used in inhibition studies. We obtained a synthetic 13-mer peptide (Bio-Synthesis, Lewisville, Tex.), YRQFVTGFWGPPC, (SEQ ID NO:7) which was designed to include the PS76 non-apeptide sequence (designated as PS76p) plus the 3 amino acid pIII tether (GPP) and an added cysteine (C) to facilitate peptide coupling to a carrier protein, such as keyhole limpet hemocyanin (KLH). Due to the high number of hydrophobic amino acids in the synthesized PS76p, solubility tests were run to determine conditions for dot blot inhibition studies. The PS76p was soluble in trifluoroacetic acid, dimethylsulfoxide, 20% v/v acetic acid, citrate and acetate buffers below pH 5.4, borate buffer above pH 8.5, but not soluble in deionized water, phosphate buffered saline (PBS), 15% v/v dimethylformamide, chloroform, or methanol.

Because pH below 5 or above 8.5 is required to solubilize PS76p, the reactivity of MAb B6.1 at low and high pH was investigated. The antibody (at 0.01 µg/ml) maintained its capacity to recognize dot blots of 2-ME extract (0.5 µg/ml) between pH 4 and 5 and between pH 8 and 9. Although MAb B6.1 is functional at these pH conditions, the PS76p may or may not retain proper epitope conformation at this pH and may require tethering to a carrier molecule to enable inhibition studies to be done at pH 7. Initial inhibition assays at pH 8.6 with up to 200 µM PS76p were negative, suggesting that confirmation could be a factor.

Inhibition assays at physiologic pH were performed with peptide attached to carrier protein. The PS76p, with the added cysteine as described above, was conjugated to KLH and to ovalbumin (OVA) by use of two different heterobifunctional, N-hydroxysuccinimide-ester crosslinkers (Pierce Chemical Co.), specifically m-maleimidobenzoyl-N-hydroxysuccinimide ester (MBS) and N-γ-maleimidobutyrloxyl) succinimide ester (GMBS). The procedure was carried out in degassed, nitrogen-sparged 0.05M citrate-phosphate buffer pH 5 to maintain PS76p solubility. Briefly, 10 mg carrier protein in citrate-phosphate buffer was stirred with 2 mg crosslinker (1 h, under nitrogen, room temperature) and then passed over a small Sephadex G25 column to isolate the carrier protein-linker product from unreacted crosslinker. The KLH-MBS and OVA-GMBS fractions were placed into fresh glass tubes and nitrogen sparged. Peptide PS76p (4 or 5 mg, dissolved in 50 µl dimethylformamide) was added to each protein-linker solution and stirred at room temperature under nitrogen atmosphere for 4 hours. Samples were dialyzed at 4° C. against two changes of citrate-phosphate buffered pH 5 to remove free peptide, and then dialyzed against four changes of phosphate buffered saline pH 7.2.

Figure 3:
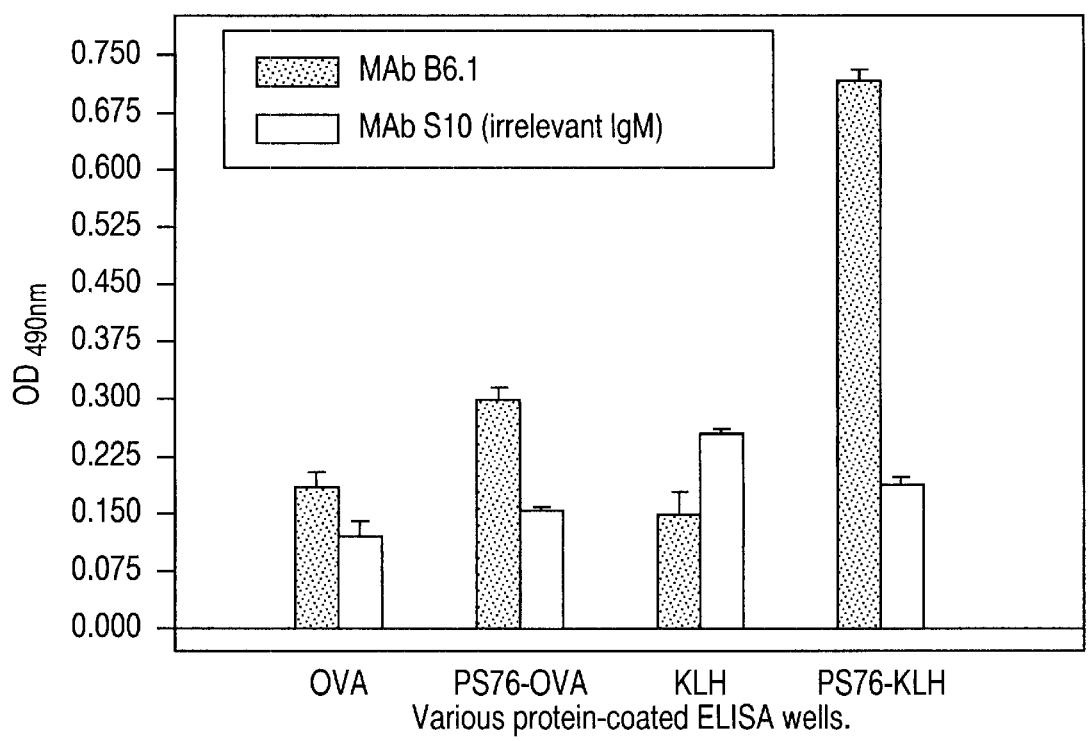
FIG. 3 shows MAb B6.1 recognition of peptide mimotopes conjugated to carrier protein. The nonapeptide mimotope from PS76 was conjugated via NHS-ester heterobifunctional linkers to keyhole limpet hemocyanin (PS76-KLH) and ovalbumin (PS76-OVA). An immunoassay was done in which microtier plate wells were coated with carrier protein alone or the synthetic peptide-carrier protein conjugates and incubated with MAb B6.1 or irrelevant IgM MAb S10, followed by an enzyme conjugated secondary antibody. Results show that MAb B6.1 recognizes the synthetic peptide attached to carrier protein. The greater binding of MAb B6.1 by the PS76-KLH conjugate reflects the greater conjugation capacity (more available lysines) of KLH compared to OVA.
Figure 4:
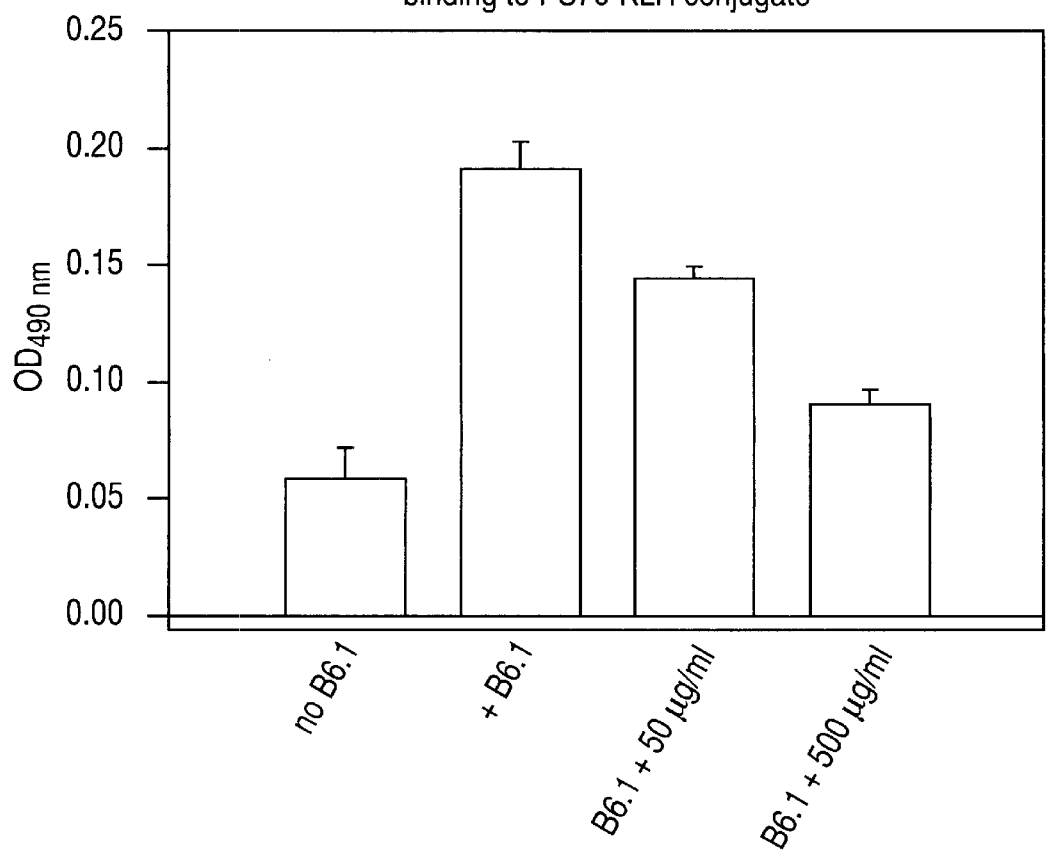
FIG. 4 shows *C. albicans* carbohydrate epitope inhibition of MAb B6.1 binding to the PS76-KLH conjugate. Microtiter plate wells were coated with PS76-KLH, blocked, and incubated with premixed samples of MAb B6.1 in block alone or in block containing acid-=hydrolyzed 2ME extract at concentrations of 50 or 500 μg/ml. Wells were washed and incubated with enzyme-conjugated secondary antibody. Results demonstrate dose-dependent inhibition of MAb B6.1 binding to the peptide-carrier protein conjugate by the *C. albicans* carbohydrate extract.

Samples of the final conjugates, PS76p-MBS-KLH (i.e. PS76-KLH) and PS76p-GMBS-OVA (i.e. PS76-OVA) were tested by enzyme linked immunosorbent assay (ELISA) for reactivity with MAb B6.1 at physiologic pH. Microtiter plate wells were coated with the peptide conjugates or the carrier proteins alone, washed (Tris buffered saline with 0.1% Tween-20), and blocked in 5% BLOTTO/phage buffer. Wells were washed and incubated with MAb B6.1, an irrelevant IgM (MAb S10) or block only, washed, and a horseradish peroxidase-conjugated goat anti-mouse Ig (G and M) was added. Wells were washed and an o-phenylenediamine substrate solution was added, incubated 10 min and color development stopped with 10% sulfuric acid, and the plate read at OD=490 nm. Both PS76-KLH and PS76-OVA conjugates reacted with MAb B6.1, but not substantially with MAb S10, FIG. 3. MAb B6.1 showed minimal reactivity with the KLH or OVA alone. The PS76-KLH conjugate was utilized in an ELISA-based inhibition assay as follows. Microtiter plate wells were coated with PS76-KLH and blocked as above. MAb B6.1 (20 µl/ml in block) was pre-incubated with or without either 50 or 500 µg of acid-hydrolyzed 2ME extract per ml of solution, and then added to the conjugate coated well. The 2ME extract inhibited MAb B6.1 binding to PS76-KLH in a dose-dependent fashion, as shown in FIG. 4.

EXAMPLE 5

Antibody response of mice immunized against PS76p. If PS76p truly mimics the B6.1 carbohydrate epitope (i.e., β-1,2 trimannose), then anti-PS76p antibodies would react with the surface of C. albicans and with the 2-ME extract. Immunizations were done by four methods described below.

Method 1

Administration of peptide intraperitoneally (i.p.) BALB/c mice (4 animals) were immunized i.p. with PS76p (1 mg per dose) mixed into sterile PBS (degassed and nitrogen sparged) with and without RS-700MPL+TDM Ribi Adjuvant (Ribi Immunochem, Hamilton, Mont.). The insolubility of PS76p in PBS, as noted above, produced a particulate inoculum which was sonicated briefly (10 sec, ice cold) to minimize particulate size prior to injection. Animals were boosted with 1 mg PS76p at day 21 and serum samples were obtained on day 28. Sera from all four mice agglutinated hydrophilic C. albicans cells and agglutinated 2-ME extract-latex beads. The anti-Candida response appeared somewhat stronger in the animals receiving peptide with adjuvant.

Figure 5:
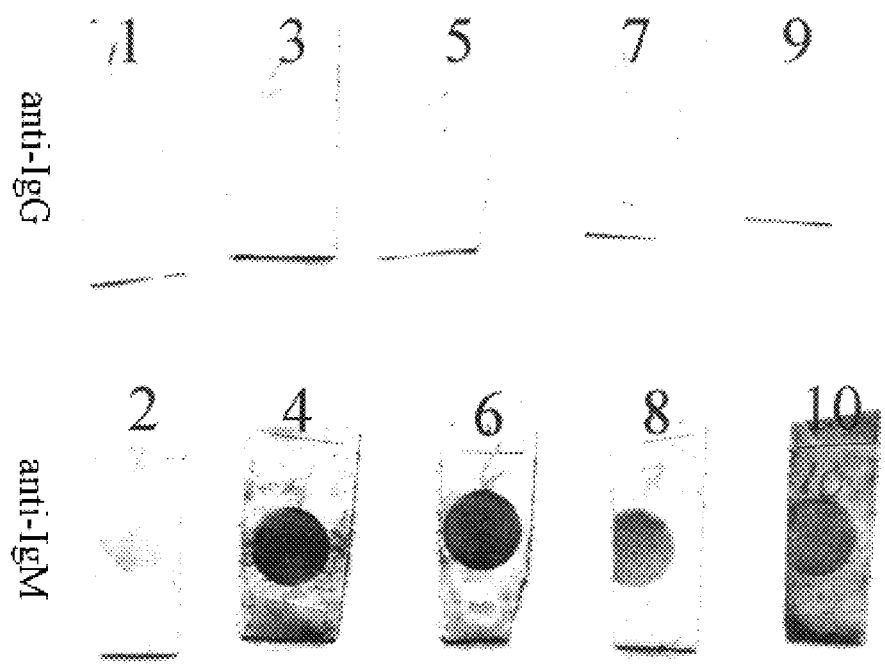
FIG. 5 shows that immunization of mice with the synthetic peptide mimotope elicits anti-Candida carbohydrate responses that are predominantly IgM. BALB/c mice were immunized with 1 mg PS76p in phosphate buffered saline with or without RS-700MPL+TDM Ribi Adjuvant. Animals were boosted at day 21 and serum samples were obtained on day 28. Dot blots of *C. albicans* 2ME extract were blocked and incubated in samples of immune or pre-immune serum and tested with either γ-chain specific or μ-chain specific secondary antibodies. All peptide mimotope-immunized mice showed reactivity to the 2ME extract whereas the normal mouse serum control was negative. The anti-Candida response was primarily IgM class antibodies.

Reactivity of the anti-PS76p sera from the mice was also tested in dot blot assays against 2-ME extract (1 µg/dot). Immune sera were diluted 1:10 in 5% BLOTTO-phage buffer, incubated 12–16 h with preblocked dot blots, washed and incubated with peroxidase-conjugated goat anti-mouse Ig (G,M, and A). All four immunized mice showed reactivity to the 2-ME extract whereas the normal mouse serum control (also 1:10 dil) was negative. Additional dot blots were incubated in primary antibodies as above and reacted with either γ-chain specific or µ-chain specific secondary antibodies. These blots indicate that the response appears to be primarily IgM, as shown in FIG. 5.

Animals were administered booster immunizations of PS76p every two weeks and serum samples obtained 1 week after each. An ELISA assay was utilized to determine any change in titer for the anti-PS76p antiserum samples. Briefly, 2ME extract-coated wells or wells coated with an irrelevant carbohydrate were blocked in 5% BLOTTO/ phage buffer and incubated with dilutions of either pre-immune sera or various anti-PS76p antiserum samples. Subsequent steps with the secondary antibody and substrate solution were as described above for ELISA. All of the anti-PS76p serum samples reacted with 2ME extract and recognized the peptide-carrier protein conjugates, but not the irrelevant carbohydrate or the carrier proteins alone. Titers against 2ME extract did not increase much above 40 for the intraperitoneal (i.p.) immunizations. Other BALB/C mice (2 animals) were immunized with PS76p plus Ribi adjuvant (1 mg/dose subcutaneous inoculation (s.c.), and reached higher anti-PS76 antibody titers (e.g. 160 by ELISA) after the second boost. ELISA tests performed with class-specific secondary antibody reagents confirm that the response is primarily IgM.

Method 2

Figure 6:
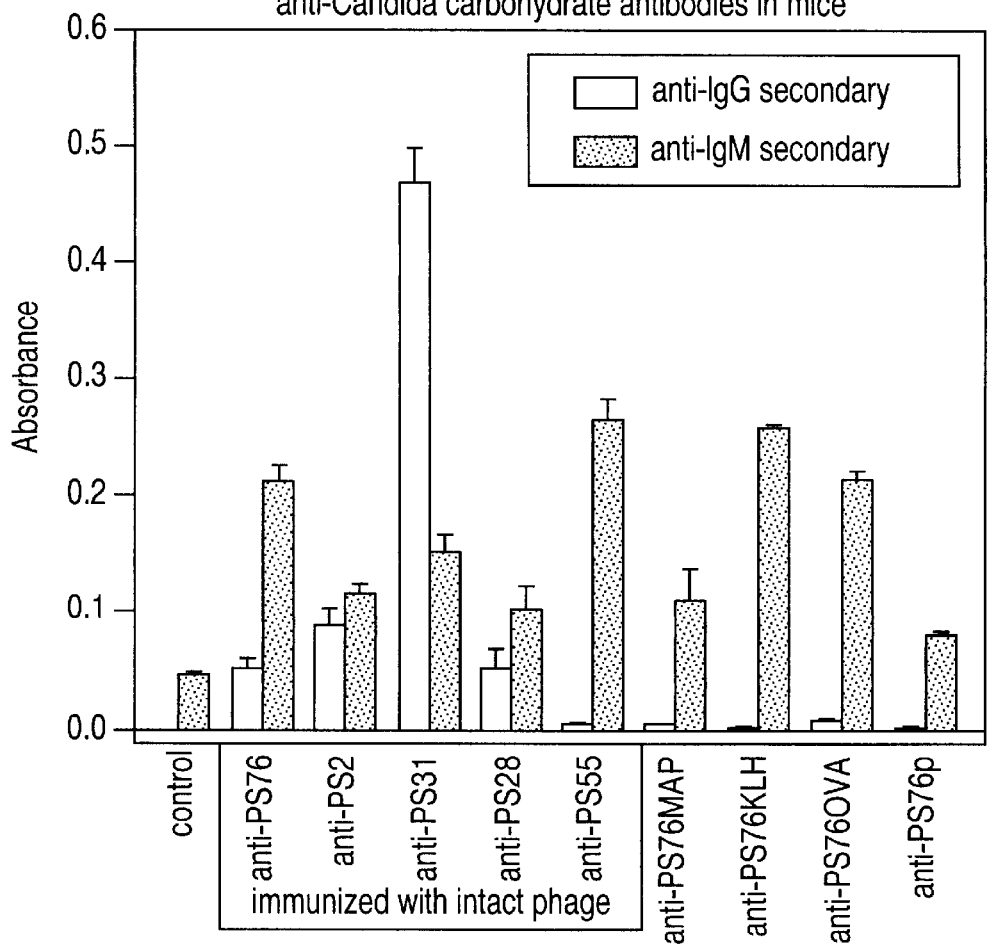
FIG. 6 shows recognition of the Candida carbohydrate epitope by antiserum samples from mice immunized with various peptide mimotope preparations. BALB/c mice were immunized with various samples (plus adjuvant Ribi R-700): synthetic peptide-carrier protein (PS76-MAP, 25 μg per dose); or individual phage clones (PS76, PS2, PS31, PS28, and PS55; $2 \times 10^{11}$ pfu per dose). Serum samples were assayed for reactivity against *C. albicans* 2ME extract by immunoassay. Microtiter plate wells were coated with 2ME extract or an irrelevant carbohydrate, blocked, washed and incubated with serum samples or control normal mouse serum (NMS) diluted in block, and tested with either γ-chain specific or μ-chain specific secondary antibodies. Results show than peptide mimotope immunization elicits immune responses that recognize carbohydrate epitopes in the 2ME extract of *Candida albicans*. With the exception of intact phage immunizations, the antibody responses were IgM class. Immunization with 4 or 5 phage-displayed peptide mimotopes elicited class switch to IgG antibodies.

Administration of PS76-KHL and PS76-OVA conjugates BALB/C mice (4 animals) were immunized s.c. with either PS76-KLH or PS76-OVA (250 μm per dose). Intervals for booster immunization and obtaining serum samples were as above. ELISA titer values against 2ME extract for both the anti-PS76-KLH and anti-PS65-OVA antisera were 320. The antiserum samples also recognized the opposite carrier-peptide conjugate but not the opposite carrier protein. ELISA tests performed with class-specific secondary antibody reagents confirm that anti-conjugate responses are primarily IgM, as shown in FIG. 6.

Method 3

Administration of PS76p as a multiple antigen peptide (MAP) construct. The nonapeptide PS76p (YRQFVTGFW; (SEQ ID NO:1) where: Y, tyrosine; R. arginine; Q, glutamine; F, phenylalanine; V, valine; T, threonine; G, glycine; W, tryptophan) was synthesized on a branched-lysine core to produce eight, radically displayed peptides (Bio-synthesis, Lewisville, Tex.). This MAP construct, PS76-MAP, when mixed with PBS is slightly soluble compared to the PS76p alone. PS76-MAP was administered to BALB/C mice (4 animals, 25 μg per dose) by s.c. immunizations with Ribi adjuvant. Intervals for booster immunization and obtaining serum samples were as above. The ELISA titer for pooled anti-PS76-MAP antiserum after the first boost was 40 against 2ME extract. ELISA tests performed with class-specific secondary antibody reagents confirm that the anti-PS76-MAP response is primarily IgM, as seen in FIG. 6.

Method 4

Administration of individual phage clones PS76, PS2, PS31, PS28, and PS55. BALB/C mice (1 animal per each phage clone) were immunized s.c. with 2×10$^{11}$ pfu of PS76, PS2, PS31, PS28, or PS55 mixed with Ribi adjuvant. Intervals for the first booster immunization and obtaining serum samples were as above. Against 2ME extract, the ELISA titers for the anti-phage antibody samples were: 320 for anti-PS55;640 for anti-PS76, anti-PS2 and anti-PS28; and 1280 for anti-PS31. Responses, tested against 2ME extract, demonstrates class switch from IgM to IgG antibodies, except for anti-PS55, as seen in FIG. 6.

EXAMPLE 6

Peptide sequences with potential vaccine and therapeutic applications.

From the above experiments and results the following amino acid sequences have vaccine and therapeutic potential.

Model sequence derived from PS76 clone (expressed as N-terminal—C-terminal direction):

YRQFVTGFW; (SEQ ID NO:1) where: Y, tyrosine; R, arginine; Q, glutamine; F, phenylalanine; V, valine; T, threonine; G, glycine; W, tryptophan.

Consensus sequences of amino acids and amino acid positions based upon several clones with reactivity to MAb B6.1:

ArXXAr(Z)ZZArAr; where: Ar, aromatic amino acid (F, W or Y); X, any amino acid; Z, equals S (where S, serine), T or G; (Z), is S, T, or G which may or may not be present. As is clear to those of skill in the art, one can devise functional equivalents to any of the above sequences and routinely test the amino acid sequences to determine if they maintain their functional integrity and properties. The functional equivalents may be longer or shorter in length than the disclosed nonapeptide. In one embodiment the sequence has 4–12 amino acids. In an alternative embodiment the sequence has 5–9 amino acids.

EXAMPLE 7

Vaccine and therapeutic uses of above amino acids. The amino acids may be coupled to carrier proteins, such as keyhole limpet hemocyanin (KLH), tetanus toxoid, or a cell wall protein from *C. albicans*. The conjugate administered in combination with an appropriate adjuvant, such as the Ribi MPL, will induce a protective antibody response and/or cell mediated response against hematogenous disseminated candidiasis and against *Candida vaginitis*. Such vaccine preparations can be administered to patients who will be at high risk of developing hematogenous disseminated candidiasis and to women who experience recurrent *Candida vaginitis*.

In addition, once a mimetic peptide of the invention is identified and sequenced, DNA encoding the amino acid sequence of the peptide can itself be used as a vaccine. Techniques for preparing the specified DNA coding regions within suitable DNA delivery vectors are well established. An example strategy for expression of the peptide mimotopes is described below.

Figure 7:
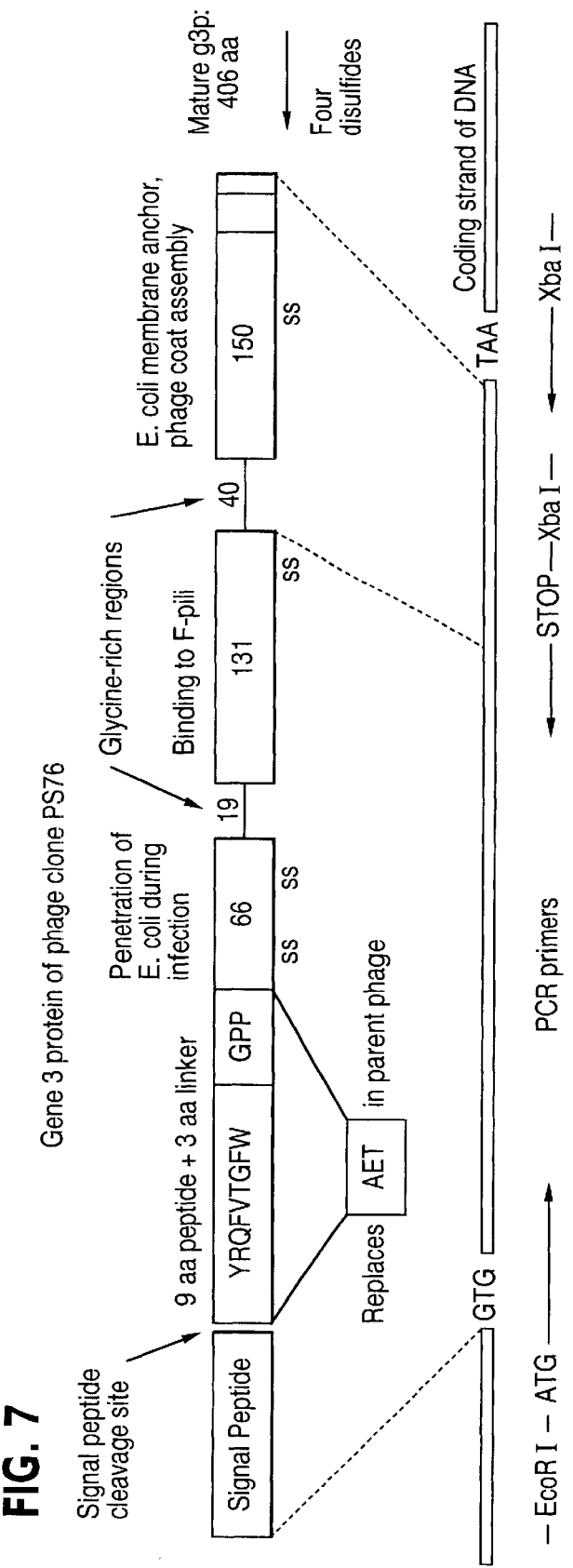
FIG. 7 diagrams an example of a cloning strategy for expression of peptide mimotopes in appropriate mammalian vectors for DNA immunization.
Figure 8A:
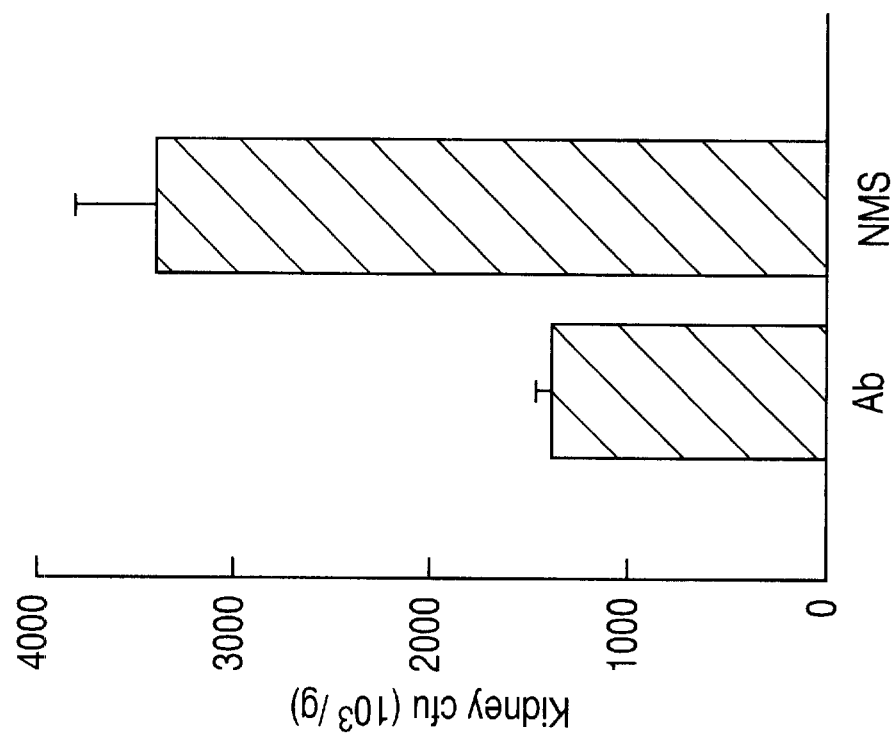
FIG. 8 shows polyclonal antiserum (Ab) protects normal and SCID mice against disseminated candidiasis. Polyclonal antiserum from L-adhesion-vaccinated mice was administered to BALB/cByJ (A') and SCID (B) mice, the animals were challenged i.v. with *C. albicans*, and the resulting kidney candidal CFU per gram of tissue were determined. Bars, standard errors. Differences between the values obtained from mice that received polyclonal antiserum and control mice that received NMS were significant ($P<0.01$).
Figure 8B:
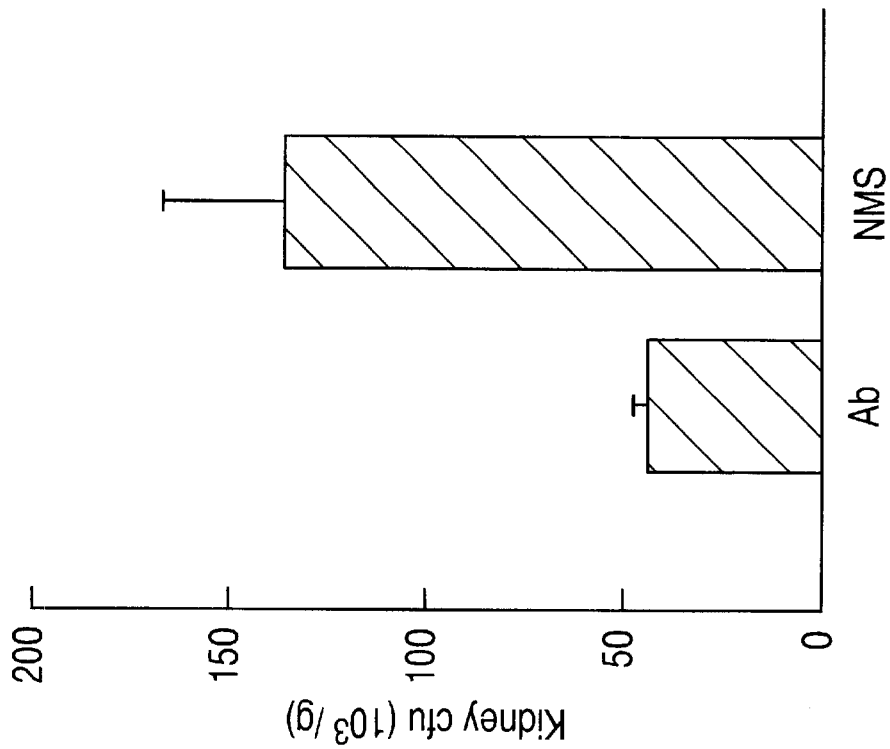
Figure 9A:
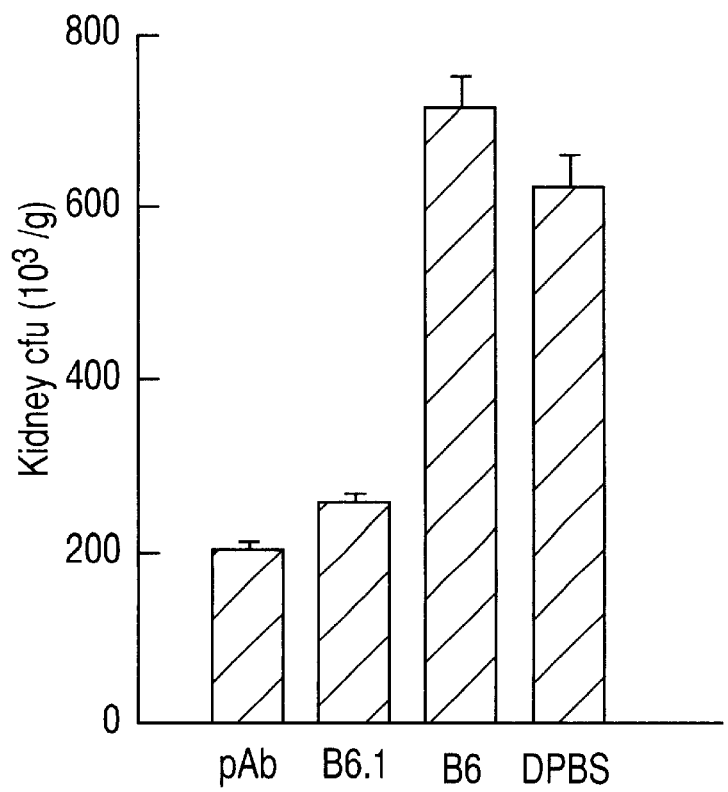
FIG. 9 shows MAb specific for a phosphomannan fraction that contains candidal adhesions protects mice against disseminated candidiasis. BALB/cByJ mice were given polyclonal antiserum (pAb), MAbs specific for either the mannan adhesion fraction (Mab B6.1) or some other cell surface determinant (Mab B6), or buffer (DPBS) as a control. The animals were challenged i.v. with $5 \times 10^5$ viable yeast cells, and susceptibility to disseminated candidiasis was assessed by determining candidal CFU in the kidneys (A) or by survival curves (B). In both cases, significant differences ($P<0.01$) between that received either polyclonal antiserum or MAb B6.1 and DPBS controls were found.
Figure 9B:
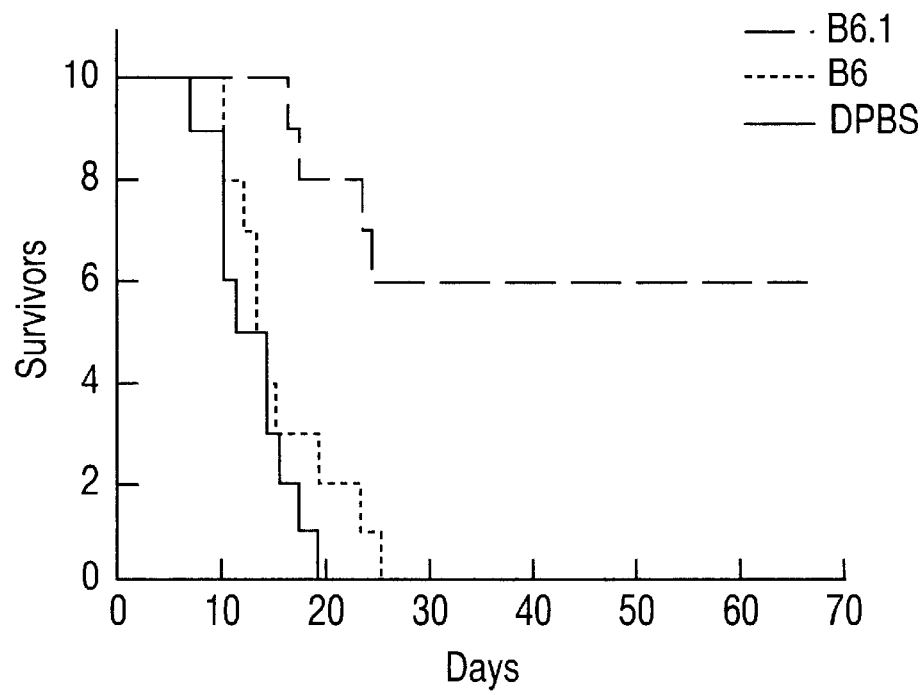
Figure 10:
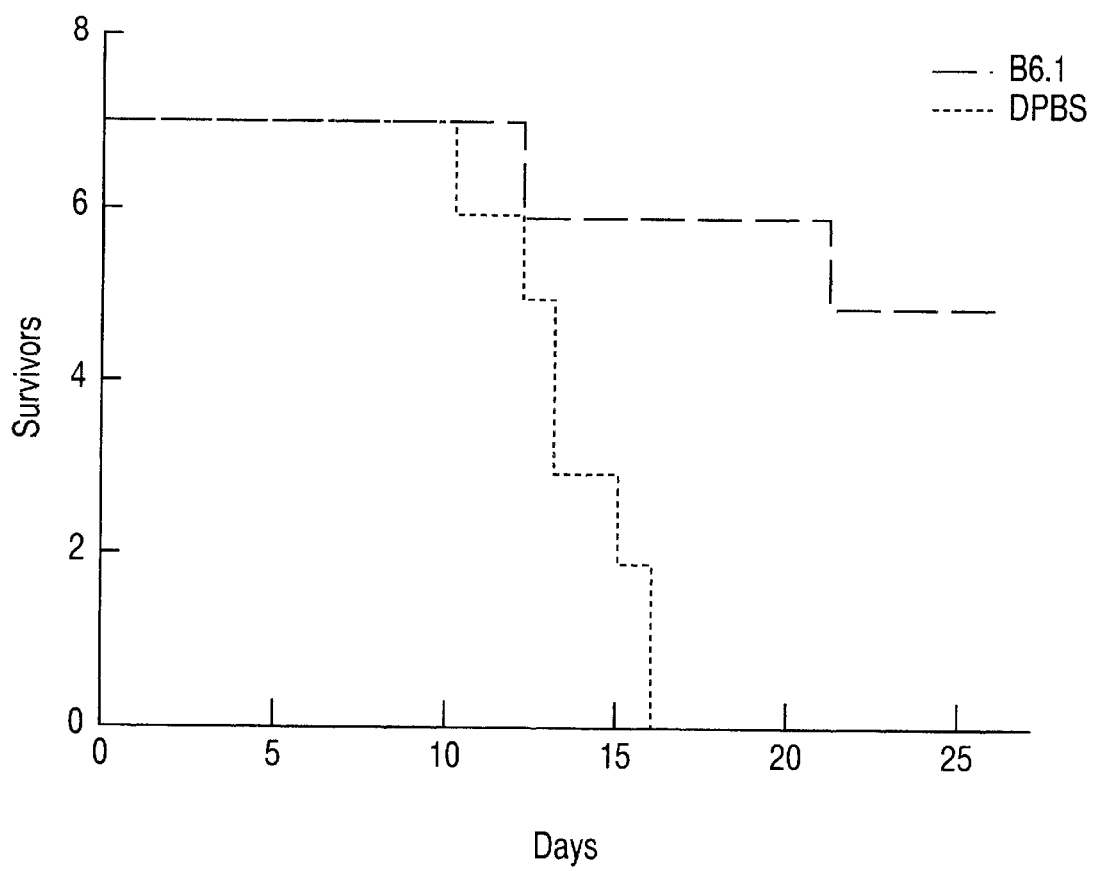
FIG. 10 shows MAb B6.1 protects SCID mice against disseminated candidiasis. BALB/cByJSmn-scid/J male mice were given MAb B6.1 intraperitoneally and challenged i.v. with $5 \times 10^5$ *C. albicans* cells. The resulting survival curves were plotted and found to significantly ($P<0.01$) differ from those of mice given buffer (DPBS) instead of the MAb.
Figure 11:
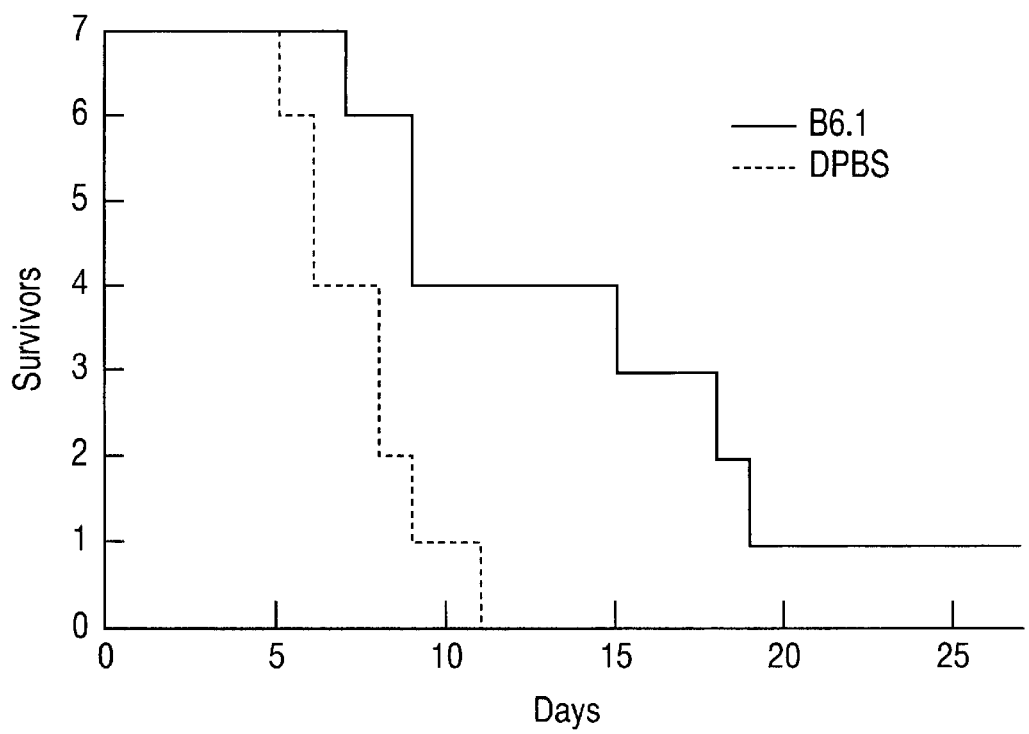
FIG. 11 shows disseminated Candidias By Survival Time Measurements. Therapeutic effect of MAb B6.1 on candida infected mice (one hour infection). BALB/cByJ female mice, N35da old were given $5 \times 10^5$ yeast cells i.v. One hour later they received MAb B6.1 or buffer (DPGS) i.p. MST= mean survival time MST (days); DPGS $9.0 \pm 2.0$ B6.1 $16.4 \pm 8.3$.
Figure 12:
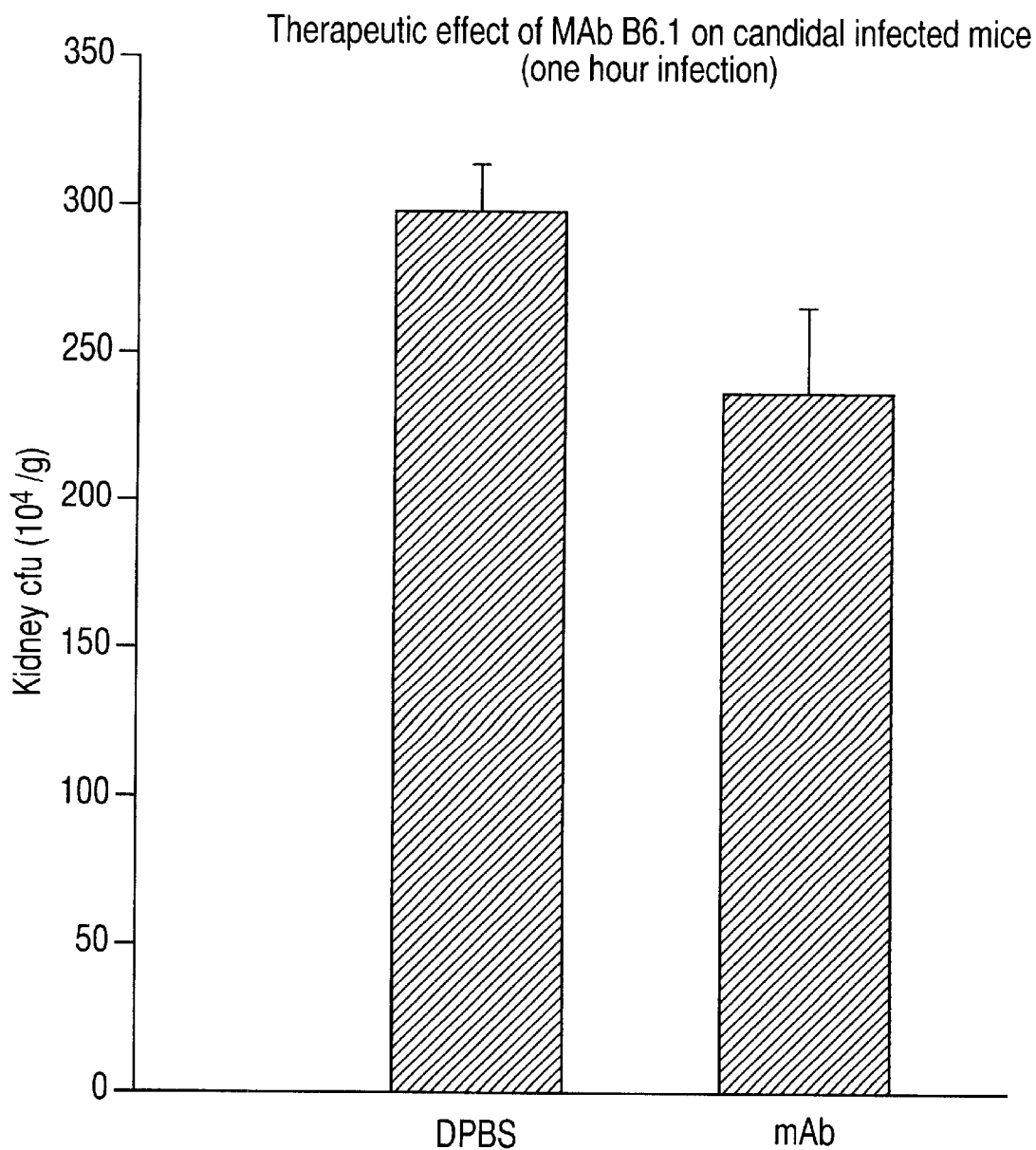
FIG. 12 shows the therapeutic effect of MAb B6.1 on candidal infected mice (one hour infection). Same as FIG. 4 design except that kidney cfu 48 h after the i.v. infection was used as the indicator of disease severity.
Figure 13:
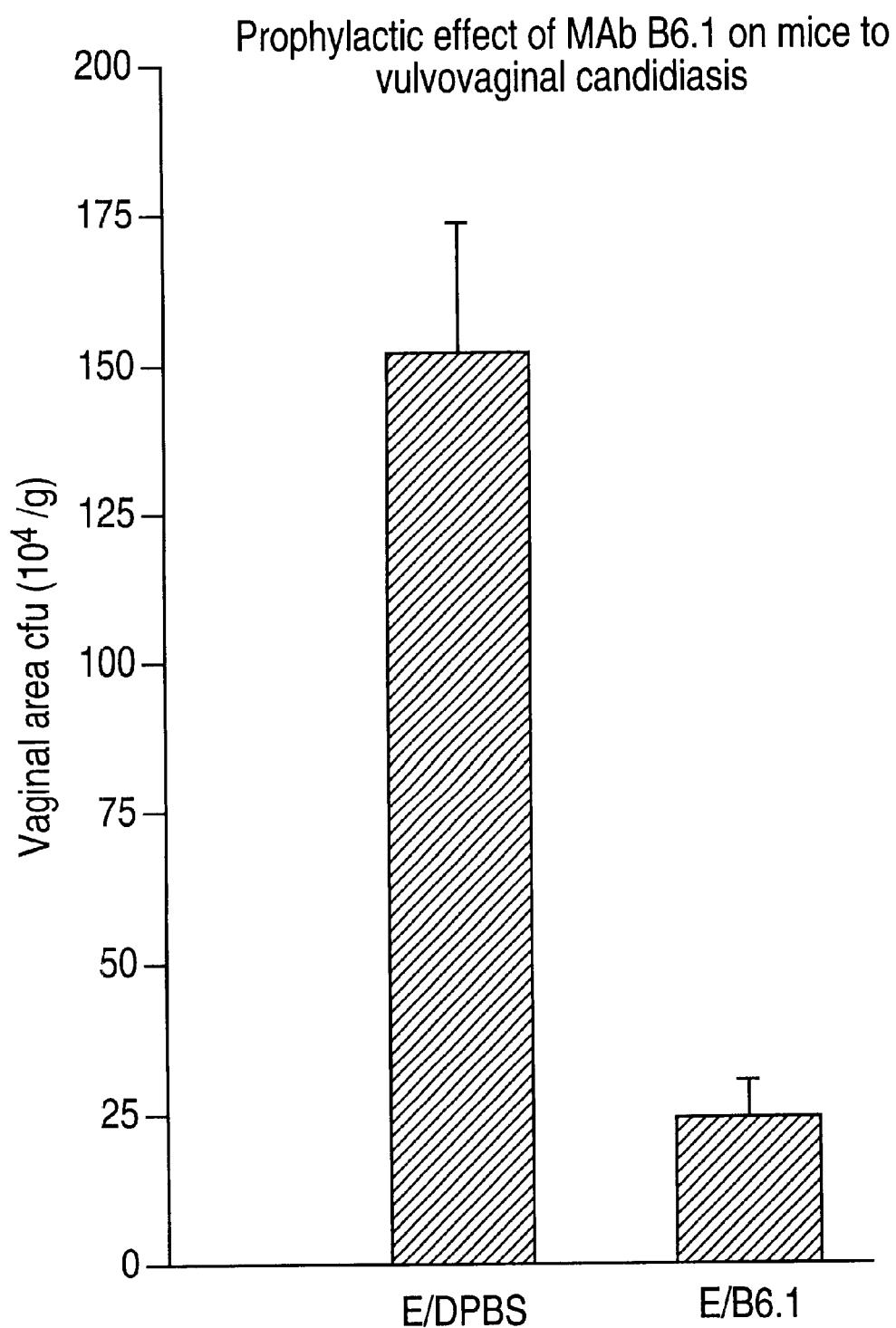
FIG. 13 shows the Prophylactic effect of MAb B6.1 on mice to vulvovaginal candidiasis. DPBS=Dulbecco phosphate buffered saline, E=estradiol Mice (BALB/cByJ, penale N35–45da old) were given estradiol subcu, 72 h later they received buffer (DPBS) or MAb B6.1, i.p. Four h after the i.p., animals received $5 \times 10^5$ *C. albicians*. Intravaginally, 20 h later they received MAb B6.1 or buffer again i.p. for *C. albicans* cfu.
Figure 14:
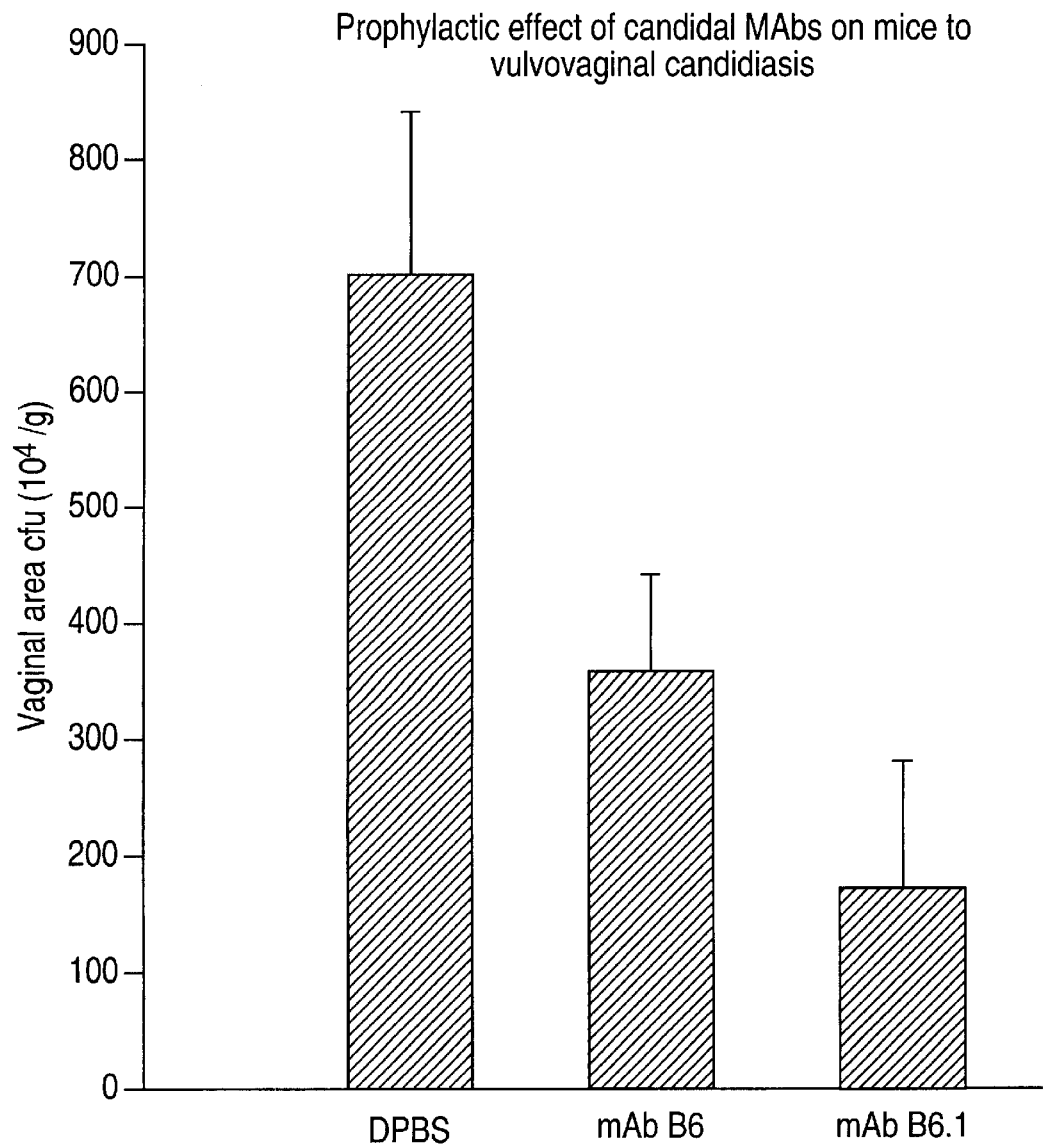
FIG. 14 shows the prophylactic effect of candidal MAbs on mice to vulvovaginal candidiasis. All mice were pretreated with estradiol before the mAb treatments. Same design as B-3, but one group of animals received MAb B6.

Phage clones isolated by affinity selection with protective MAb B6.1 have N-terminal display of nonapeptides on the gene 3 protein (g3 p or pIII). Data indicate that the nonapeptides function as structural mimics of the Candida β-1,-trimannosyl epitope recognized by MAb B6.1. The planned DNA vaccines will encode one or more of these nonapeptide sequences to elicit host immune responses with the potential to confer protection against candidiasis. To explore the properties of the designed and constructed DNA vaccines, the expression of encoded peptides and antigens is being evaluated first in cultured mammalian cells. All or part of the phage gene 3 has been included in the initial DNA constructs (diagram shown in FIG. 7), in order to re-create the phage-displayed peptide mimotopes that are recognized by MAb B6.1. This g3 p-peptide mimotope construct was suggested from data indicating that mice immunized with phage-displayed nonapeptides produced greater antibody titers and IgG responses against Candida 2ME extract compared to animals receiving synthetic peptide alone. Thus, the relevant conformation of peptide mimotopes may depend on its attachment to the phage protein, and the phage protein may serve as an immunogenic carrier for the peptide. Four constructs have been tested: two are negative controls, representing the parent phage protein without the N-terminal peptide addendum of 9 random amino acids and a 3 amino acid linker (GPP); the other two represent the most promising B6.1-reactive library clone, PS76, which has the sequence YRQFVTGFW at its amino terminus.

PCR amplification of cloned phage DNA allowed for engineering of appropriate restriction sites and codon modifications in the constructs. For directional insertion into sequencing plasmids and expression plasmids, EcoR I and Xba I restriction sites were appended. For translation in mammals, a start methionine codon (ATG) was added to the coding sequence, since translation of the phage gene 3 mRNA in E. coli initiates at a GUG rather than an AUG codon. Bases around the start codon were designed to establish a strong translational start site. Computer analysis of the g3p signal peptide sequence suggested that it is also likely to serve as a signal peptide in eukaryotic cells, with posttranslational cleavage occurring in the same position as in E.coli (resulting in the same N-terminus on the mature protein). The C-terminal hydrophobic sequence of g3p is expected to function as a transmembrane anchor in mammalian cells as it does in E. coli. If g3p folds correctly in the mammalian endoplasmic reticulum, it may then be transported to the surface of the cell (with the N-terminus exposed on the outside of the cell). For two of the constructs, a truncation and engineered stop codon created a shorter version of g3p, lacking the C-terminal half (and thus lacking the transmembrane anchor). This version would be expected to translocate into the lumen of the endoplasmic reticulum of mammalian cells, be soluble, and if folded correctly would be secreted from the cell.

The four constructs were cloned into PGEM (Promega, Inc.) for mapping. Single-stranded phagemids were generated and purified to facilitate DNA sequencing. All PCR-generated components were sequenced to check for unwanted mutations that might have been introduced during in vitro amplification. The four g3p constructs were transferred from pGEM to pBGSA, a mammalian expression vector that is active in a variety of mammalian cell types (Uthayakumar, S. and Granger, B. L., 1995. Cell surface accumulation of overexpressed hamster lysosomal membrane glycoproteins. Cell. and Mol. Biol. Res. 41: 405–420). The plasmids were purified and prepared for transfection into mammalian cell lines. The plasmids were first transfected into Chinese hamster ovary (CHO) cells using the calcium phosphate method; stably-transformed cells were selected with G-418, and analyzed by indirect immunofluorescence (IFA) microscopy using MAb B6.1, anti-PS76p antiserum, and a MAb against g3p. Even though the transformed cells were stably resistant to G-418, and had evidently integrated the plasmids into their genomes, no expression of the g3p constructs were detected by IFA.

To achieve greater levels of expression, the plasmids were transfected into COS-1 cells, which are capable of replicating the plasmids and generating exceptional amounts of the encoded proteins. IFA tests indicated that expression of g3p was readily detectable and it appeared to be distributed primarily in the endoplasmic reticulum. Several different transfection methods and variations were tested to increase the proportion of cells that would express detectable g3p. Co-transfection of control plasmids that were designed to express mammalian lysosomal membrane proteins showed that far more cells expressed the control protein than 3 gp, and that expression of g3p was not obviously toxic or lethal to the cells (such toxicity might have selectively eliminated the g3p expressors). Therefore, g3p is likely being broken down rapidly by the mammalian cells. It is well known that secretory and membrane proteins that do not fold or assemble properly are typically degraded in the endoplasmic reticulum rather than being transported to other cellular destinations; g3p, which evolved to function in *E. coli*, is less likely to be processed properly by mammalian cells.

This possibility was further tested by treating the COS-1 cells with a protease inhibitor (ALLN) that can inhibit proteases in the endoplasmic reticulum of living cells. This treatment resulted in a significant increase in the frequency and mount of g3p detectable by IFA, supporting the idea that g3p normally may have a very short lifespan in mammalian cells. The antigen was detected in the Golgi apparatus as well as in the endoplasmic reticulum. Less of the truncated version of g3p (without a membrane anchor) was detectable; whether any of it is secreted from the expressing cells under these conditions remains to be determined.

None of the constructs or conditions tested so far have shown binding of MAb B6.1 to the PS76 version of g3p by IFA. Possible explanation include: signal peptide cleavage does not occur as predicted; the N-terminal nonapeptide of PS76 g3P is degrated more rapidly than the rest of g3p; the nonapeptide (which is relatively hydrophobic) is sterically inaccessible to the IgM MAb B6.1; the nonapeptide is post-translationally modified by mammalian cells in a manner that destroys the B6.1 epitope (as compared to the form of the peptide in the mature phage); or that avid binding of MAb B6.1 requires at least several g3p monomers together as displayed by the phage particle, but not re-created by the mammalian cells.

Two additional controls and associated DNA constructs are currently being tested to evaluate the g3p expression by mammalian cells. First, phage clone S9-24 displays a dadecapeptide at the N terminus of g3p that binds IgM MAb S9, which recognizes a streptococcal carbohydrate antigen (Pincus, S. H., et al., 1998. Peptides that mimic the group B streptococcal type III capsular polysaccharide antigen, J. Immunol. 160: 293–298). The p3 gene of clone S9-24 was prepared as described above and expressed in COS-1 cells. Preliminary results indicate that g3p is expressed and that MAb S9 recognizes expressed dodecapeptide in the transfected cells. If confirmed, it will be the first demonstration that a peptide epitope appended to p3 can indeed be re-created by a mammalian cell. Secondly, an IgG MAb that binds with high affinity to an actual, non-mimetic, peptide clone (MAb and phage clone kindly supplied by Jim Burrit at Montana State University) will be utilized to examine the importance of antibody isotype and affinity in the IFA and other assays. It should further define the utility and limitations of g3p expression by mammalian cells.

The relevance of these in vitro observations to the potential usefulness of the g3p constructs in DNA vaccines will be assessed in planned animal experiments. Rapid degradation of the peptide-bearing proteins may actually facilitate presentation of the peptides by major histocompaitility proteins, and thus facilitate an immune response by the host animal.

EXAMPLE 8

Antibodies specific for the peptides could be used prophylactically to prevent hematogenous disseminated candidiasis and *Candida viginitis*, and protective antibodies could be used therapeutically against *Candida viginitis.*

The invention also investigates a vaccine induced alteration of pathogenesis of candidiasis generally, particularly hematogenous disseminated candidiasis and mucocutaneous candidiasis. The invention focuses on optimizing a vaccine against candida adhesions and determining the effect of immune serum on its ability to protect mice against candidiasis.

The inventors show that 1) the Candida vaccine can be used to protect naive individuals against Candida infections before they are infected; 2) the Candida vaccine can be used to treat previously infected individuals; 3) the antibodies can be used to protect naive individuals before they are infected; and 4) the antibodies can be used to treat previously infected individuals.

Data of the invention indicates that i) immune responses against candida phosphomannoprotein moieties protect mice against disseminated and mucocutaneous candidiasis, (ii) sera from immune animals transfer protection to naive mice.

The underlying emphasis of studies leading to the present invention was to determine the role of adhesion-specific antibodies in host resistance to disseminated candidiasis and define the effects of these antibodies on fungal attachment phenomena as measured by several in vitro adherence systems, and by in vivo analysis. The invention focuses on the phosphomannoprotein complex which the inventors have shown to contain adhesion sites.

The adhesion(s) responsible for adherence of C. albicans hydrophilic yeast cells to the splenic marginal zone was isolated, and presentation of the adhesion (as part of the phosphomannoprotein complex) to mice resulted in induction of specific antibody responses. Mice were induced to produce polyclonal antisera specific for the phosphomannoprotein and a few mAbs have been isolated. Mice who develop anti-phosphomannoprotein responses show increased survival against disseminated candidiasis. Sera from vaccinated mice specifically react with phosphomannoprotein. Immune serum has been shown to passively transfer resistance to naive animals. The invention addresses the role of antibodies in host defense against disseminated candidiasis.

An understanding of mechanisms by which blood-borne C. albicans yeast cells disseminate in the host may be gained through knowledge of fungal adhesions and host ligand molecules to which these adhesions bind. The findings by Klotz and others that C. albicans attaches to exposed basement membrane (ECM) and platelet aggregates on the ECM, led to speculation that damaged endothelial cells expose the ECM and allow attachment of C. albicans from the circulatory system (Klotz, S. A. 1992. Fungal adherence to the vascular compartment: A critical step in the pathogenesis of disseminated candidiasis. Clin. Infect. Dis. 14:340–347). Perhaps relevant to these findings is that indwelling venous catheters are responsible for increased susceptibility to candidiasis and it is believed that venous catheters damage endothelia. Importantly, the kidney is a target organ for systemic disease and this organ normally has an exposed basement membrane (ECM) as part of the glomerular apparatus. Edwards has demonstrated that C. albicans binds directly to the endothelial cells (Filler, S. G., et al. 1987. An enzyme-linked immunosorbent assay for quantifying adherence of Candida to human vascular endothelium. J. Infect. Dis. 156:561–566; and Rotrosen, D. et al. 1985. Adherence of Candida to cultured vascular endothelial cella: mechanisms of attachment and endothelial cell penetration. J. Infect. Dis. 153:1264–1274), and this event may well initiate host inflammatory changes (Filler, S. G., et al. 1994. Mechanisms by which C. albicans induces endothelial cell prostaglandin synthesis. Infect. Immun. 62:1064–1069; and Filler, S. G., et al. 1991. C. albicans stimulates endothelial cell eicosanoid production. J. Infect. Dis. 164:928–035). A shear dependent adherence assay has allowed observations that corroborate some of the endothelial binding interactions.

The adherence of C. albicans hydrophilic yeast cells to mouse splenic marginal zone macrophages and macrophages within the subcapsular and medullary sinuses of peripheral lymph nodes has been characterized by the present inventors (Cutler, J. E., et al. 1990. Characteristics of C. albicans adherence to mouse tissue. Infect. Immun. 58:1902–1908; Han, Y., et al. 1993. Binding of C. albicans yeast cells to mouse popliteal lymph node tissue is mediated by macrophages. Infect. Immun. 61:3244–3249; Hazen, K. C., et al. 1991. Differential adherence between hydrophobic and hydrophilic yeast cells of C. albicans. Infect. Immun. 59:907–912; and Kanbe, T., et al. 1992. Evidence that C. albicans binds via a unique adhesion system on phagocytic cells in the marginal zone of the mouse spleen. Infect. Immun. (60:1972–1977)).

The adhesions responsible for the yeast/macrophage interaction have been isolated and characterized (Kanbe, T., et al. 1994. Evidence for adhesion activity in the acid-stable moiety of the phosphomannoprotein cell wall complex of C. albicans. Infect. Immun. 62:1662–1668); and Kanbe, T., et al. 1993. Evidence that mannans of C. albicans are responsible for adherence of yeast forms to spleen and lymph node tissue. Infect. Immun. 61:2578–2584).

One of the adhesion sites has been identified to structure (Li, R. K., et al. 1993. Chemical definition of an epitope/adhesion molecule on C. albicans. J. Biol. Chem. 268:18293–18299), and the nature of the macrophage ligand is under investigation (Han, Y., et al. 1994. Mouse sialoadhesin is not responsible for C. albicans yeast cell binding to splenic marginal zone macrophages. Infect. Immun. (62:2115–2118).

The present inventors set out to determine whether antibodies are protective against disseminated candidiasis. Given the complexity of adhesins and variable character of the cell surface of C. albicans, the role of antibodies in host defense against disseminated candidiasis has remained a contentious issue. Evidence that argues against a protective role for antibodies is derived mostly from clinical observations showing that precipitin antibodies specific for candida antigens can be detected in the sera of most patients with disseminated or deep-seated candidiasis. Experimentally, while some investigators reported that human antibodies specific for C. albicans enhance phagocytic cell uptake of fungal elements (Diamond, R. D., et al. 1978. Damage to pseudohyphal forms of C. albicans by neutrophils in the absence of serum in vitro. J. Clin. Invest. 61:349–359), others concluded that specific antibodies may block phagocytosis of C. albicans (LaForce, F. M., et al. 1975. Inhibition of leukocyte candidacidal activity by serum for patients with disseminated candidiasis. J. Lab. Clin. Med. 86:657–666; and Walker, S. M. et al. 1980. A serum-dependent defect of neutrophil function in chronic mucocutaneous candidiasis., J. Clin. Pathol. 33:370–372).

The suggestion by some that IgE responses may inhibit phagocytosis by human neutrophils of C. albicans indicates the importance of investigating the protective nature of Ig subtypes (Berger, M., et al. 1980. IgE antibodies to *Staphylococcus aureus* and C. albicans in patients with the syndrome of hyperimmunoglobulin E and recurrent infections. J. Immunol. 125:2437–2443). In addition, none of the early investigators addressed the issue of antibody specificity. In one study on susceptibility of various kinds of immunodeficient mice to hematogenous disseminated candidiasis, the importance of candida-specific antibodies was dismissed and, instead, T-cell-mediated immunity was concluded as the important acquired-specific host defense (Cantorna, M. T., et al. 1991. Acquired Immunity to Systemic Candidiasis in Immunodeficient Mice. J. Infect. Dis. 164:936–943). The conclusions were, however, contended by others (Matthews, R. et al. 1992. Acquired immunity to systemic candidiasis in immunodeficient mice: Role of antibody to heat-shock protein 90. J. Infect. Dis. 166:1193–1194) because an alternative interpretation is that specific antibodies were not induced in the immunodeficient animals.

However, antibodies appear to assist the host in resisting disseminated candidiasis. Mourad and Friedman showed that mice with high antibody titers against *C. albicans* were relatively resistant against hematogenously disseminated disease, and immunity was transferrable to naive mice via the anti-serum (Mourad, S., et al. 1961. Active immunization of mice against *C. albicans*. Proc. Soc. Exp. Biol. Med. 106:570–572; and Mourad, S., et al. 1968. Passive immunization of mice against *C. albicans*. Sabouraudia 6:103–105).

These findings were corroborated by Pearsall who reported that serum could transfer protection to naive animals against a deep seated infection with *C. albicans* (Pearsall, N. N., et al. 1978. Immunologic responses to *C. albicans*. III Effects of passive transfer of lymphoid cells or serum on murine candidiasis. J. Immunol. 120:1176–1180). Sensitized lymphoid cells transferred cutaneous delayed hypersensitivity to naive mice, but did not protect these animals against the deep seated disease.

In 1978, Domer's group determined that *C. albicans* cutaneous infection provoked mice to produce antibodies specific for the fungus, and such animals were less susceptible to disseminated candidiasis than control (Giger, D. K., et al. 1978 Experimental murine candidiasis: pathological and immune responses to cutaneous inoculation with *C. albicans*. Infect. Immun. 19:499–509). Further experiments supported a specific protective effect. If B-cells were depleted by anti-$\mu$ therapy, the mice were unable to make antibody in response to the cutaneous infection, their T-cell activities appeared unaffected, but these animals were more susceptible to disseminated disease than controls (Kuruganti, U., et al. 1988. Nonspecific and Candida-specific immune responses in mice suppressed by chronic administration of anti-$\mu$. J. Leukocyte Biol. 44:422–433). These experiments were confirmed by other investigators (Maiti, P. K., et al. 1985. Role of antibodies and effect of BCG vaccination in experimental candidiasis in mice. Mycopathologia 91:79–85).

In unrelated observations, production of antibodies against conserved epitopes of candida and human heat-shock protein (hsp) 90 correlated with the ability of experimental animals to resist disseminated candidiasis. Patients who recovered from disseminated disease produced this antibody (Matthews, R. et al. 1992. Acquired immunity to systemic candidiasis in immunodeficient mice: Role of antibody to heat-shock protein 90. J. Infect. Dis. 166:1193–1194) and anti-hsp 90 from patient sera protected recipient mice against disseminated candidiasis (Matthews R. C., et al. 1991. Autoantibody to heat-shock protein 90 can mediate protection against systemic candidosis. Immunol. 74:20–24). Although the authors claimed that the patient's sera contained antibodies only against hsp 90, the detection method used (i.e., PAGE and Western blotting) was unlikely to show antibodies against the candida cell surface PMP.

The surface of *C. albicans* is variable, and the inventors have obtained evidence that immunodominant antigens may not necessarily be involved in critical host-*C. albicans* interactions, such as adherence events. For example, a major antigen expressed on the surface of serotype A strains is not an adhesin. Since *C. albicans* readily activates the alternative complement cascade and C3 deposition on the candida cell surface promotes ingestion by phagocytic cells, an opsonic role for specific antibodies may not be very important (Morrison, R. P., et al. 1981. In vitro studies of the interaction of murine phagocytic cells with *C. albicans*. J. Reticuloendothel. Soc. 29:23–34).

The present inventors show that the vaccine protected mice by production of antibodies specific for candida adhesins. Perhaps the ideal protective antibody response would prevent adherence of circulating yeast cells to endothelial and subendothelial surfaces, while enhancing or not affecting an interaction with phagocytic cells.

Whereas the bulk of clinical studies indicate an importance of T-cell dependent cell mediated immunity (CMI) in host resistance to mucosal candidiasis, neither clinical observations nor most animal experimental studies show that CMI plays a major role in resistance to disseminated candidiasis. (See Brawner, D. L., et al. 1992. Oral candidiasis in HIV-infected patients. AIDS Reader July/August:117–124; Fidel, P. L., et al. 1993. Candida-specific-cell-mediated immunity is demonstrable in mice with experimental vaginal candidiasis. Infect. Immun. 61:1990–199520; Odds, F. C. 1988. Candida and candidiasis. Bailiere Tindall, London.)

T-cell dependent cell mediated immune (CMI) responses appear not to be involved in host resistance to disseminated candidiasis. A possible explanation is that CMI is overshadowed in importance by the action of neutrophils, macrophages, specific antibodies and other factors.

The inventors have studied disseminated candidiasis, and immune responses to *C. albicans*, in normal and immunocompromised mice for over twenty years. Recently the variable nature of the cell surface of *C. albicans* and antibody responses by mice to *C. albicans* cell wall antigens have been analyzed.

The function of the moieties on the fungal cell surface and adherence properties was investigated. Work progressed from characterizing the surface of *C. albicans* to an understanding of functions of cell surface moieties as they relate to candida-host interactions.

Events that occur within 30–45 min after yeast cells of *C. albicans* gain access to the circulation of the host and become attached to deep tissue sites where the fungal cells may adhere either to a host phagocytic cell or to a non-phagocytic cell site, such as an endothelial cell were studied.

Clinical isolates of *C. albicans* are either serotype A or B, but one or the other serotype may predominate in human subjects depending on the immunological status of the patient. The prototype strains used are CA-1 (serotype A) and A-9 (serotype B) that have been extensively studied in the laboratory.

An important consideration in all work on *C. albicans* is the inherent variability potential of the species. Culture conditions and handling of the strains have been standardized to stabilize their characteristics and allow for long-term reproducible results.

EXAMPLE 9

Culturing of *C. albicans* to maintain constant characteristics. Strains of *C. albicans* show genetic instabilities and antigenic variability. To maintain constancy in surface characteristics throughout the experiments, the strains will be stored in 50% glycerol at −20° C., and as cell pellets in sterile water at −20° C. Fresh new working cultures will be prepared form the frozen stocks every week. For preparation of hydrophilic cells, a loopful of the glycerol stock will be used to inoculate 25 ml of GYEPB (2% glucose, 0.3% yeast extract, 1% peptone broth) in a 50 ml Erlenmeyer flask, the culture will be incubated for 24 h at 37° C. under aeration by rotation at 160–180 rmp, then serially transferred to fresh GYEPB (e.g., 3 drops of culture may be transferred to 25 ml GYEPB three to six times at 24 h intervals and incubated as above). This procedure produces almost 100% hydrophilic yeast forms in stationary phase of growth. Yeasts are harvested by centrifugation, the pelleted cells are washed three times in ice-cold deionized water, held on ice as pelleted cells until use (up to 2 h), and suspended to the appropriate working concentration in the appropriate medium.

Alternatively, yeast cells may be grown to have a hydrophobic cell surface (Hazen, K. C., et al. 1991. Differential adherence between hydrophobic and hydrophilic yeast cells of C. albicans. Infect. Immun. 59:907–91212; Hazen, K. C., et al. 1986. Influence of growth conditions on cell surface hydrophobicity of C. albicans and Candida glabrata. Infect. Immun. 54:269–271). The cultures are grown exactly as above, except that incubations are at 24° C.

A microsphere assay is used to monitor the percentage of cells that have a hydrophobic or hydrophilic cell surface (Hazen, K. C., et al. 1987. A polystyrene microsphere assay for detecting surface hydrophobicity variations within C. albicans populations. J. Microbiol. Methods. 6:289–299). Equal volumes (100 $\mu$l) of yeast cells ($2\times10^6$/ml) and hydrophobic (i.e., low sulfate) blue polystyrene microspheres (diameter, 0.801 $\mu$m; ca. $9\times10^5$ microspheres per ml (Serva Fine Biochemicals, Wesburg, N.Y.), each suspended in sodium phosphate buffer (0.05 M, pH 7.2), will be placed into acid-washed glass tubes (12×75 mm), equilibrated to 23° C. for 2 min and vigorously mixed for 30 sec. Yeast cells with three or more attached microspheres are considered to by hydrophobic.

The protocol for $\beta$-mercaptoethanol extraction of the adhesins as part of the cell wall phosphomanno-protein complex (2ME extract) is the same as previously defined in our laboratory and further detailed below (Kanbe, T., et al. 1993. Evidence that mannans of C. albicans are responsible for adherence of yeast forms to spleen and lymph node tissue. Infect. Immun. 61:2578–2584).

EXAMPLE 10

Tissue adherence characteristics of C. albicans and adhesin isolation. By use of an ex vivo adherence assay, the adherence characteristics of hydrophilic and hydrophobic yeast cells to mouse splenic and lymph node tissue was examined (Cutler, J. E., et al., 1990, Characteristics of Candida albicans adherence to mouse tissues. Infec. Immun. 58:1902–1908); Han, Y., et al. 1993. Binding of C. albicans yeast cells to mouse popliteal lymph node tissue is mediated by macrophages. Infect. Immun. 61:3244–3249; and Hazen, K. C., et al. 1991. Differential adherence between hydrophobic and hydrophilic yeast cells of C. albicans. Infect. Immun. 59:907–91212).

It was found that C. albicans hydrophilic yeast cells specifically adhere to mouse splenic marginal zone macrophages (Cutler, J. E., et al. 1990. Characteristics of C. albicans adherence to mouse tissue. Infect. Immun. 58:1902–1908; Kanbe, T., et al. 1992. Evidence that C. albicans binds via a unique adhesion system on phagocytic cells in the marginal zone of the mouse spleen. Infect. Immun. 60:1972–1978). An essentially identical binding pattern of yeast cells to the mouse spleen occurs in vivo following an intravenous (i.v.) presentation of fungal cells (Tripp, D. L. et al. 1994. Evidence for complement independent in vivo adherence of C. albicans. Abstr. Annu. Meet. ASM.).

Complement may play a role in organ distribution of C. albicans from the blood. The pattern of yeast cell adherence to the spleen is not influenced by the presence of fetal bovine serum, or the absence of serum in the ex vivo assay (Cutler, J. E., et al. 1990. Characteristics of C. albicans adherence to mouse tissue. Infect. Immun. 58:1902–1908; and Riesselman, M. H. et al. 1991. Improvements and important considerations of an ex vivo assay to study interactions of C. albicans with splenic tissue., J. Immunol. Methods 1450:153–160). However, if yeast cells are opsonized in fresh mouse serum without detectable antibodies against C. albicans (Morrison, R. P., et al. 1981. In vitro studies of the interaction of murine phagocytic cells with C. albicans. J. Reticuloendothel. Soc. 29:23–34) binding to the marginal zone is enhanced by 50–200% (Tripp, D. L. et al. 1994. Evidence for complement independent in vivo adherence of C. albicans. Abstr. Annu. Meet. ASM.).

In vivo binding of yeast cells to the splenic marginal zone appears unaffected by complement opsonization. Yeast cells become opsonized by incubation for 30 min at 37° C. in the presence of 2.5% (or more) fresh mouse serum (Morrison, R. P., et al. 1981. In vitro studies of the interaction of murine phagocytic cells with C. albicans. J. Reticuloendothel. Soc. 29:23–34). The opsonization is due to activation of the alternative complement cascade and is required for optimal phagocytosis by mouse peritoneal macrophages. When $8\times10^8$ yeast cells are complement opsonized and given i.v. to mice, the number of yeast cells that bind to the splenic marginal zone is essentially the same as compared to binding of non-opsonized yeast cells. Furthermore, mice made complement C3 deficient by treatment with cobra venom factor still show the same yeast cell adherence in vivo as in complement sufficient animals (Tripp, D. L. et al. 1994. Evidence for complement independent in vivo adherence of C. albicans. Abstr. Annu. Meet. ASM).

These results have been confirmed by Kozel's group who used a different approach. Cobra venom depleted C3 mice and normal control animals were given viable yeast cells. Forty-five min. later the animals were sacrificed and the number of fungal colony forming units (cfu) in the spleen of C3 depleted mice was similar to splenic cfu of normal controls. A very interesting finding, however, was that C3 depleted mice had higher counts in the lungs as compared to normal controls, implying that complement may play a role in the organ distribution of C. albicans yeast cells from the circulation.

Adhesins responsible for attachment of hydrophilic yeasts to splenic marginal zone are glycans (mannans) and not protein. The adhesins responsible for attachment of hydrophilic yeast cells to the marginal zone macrophages are solubilized from the fungal cell surface by extraction with $\beta$-mercaptoethanol (2ME extract) (Kanbe, T., et al. 1993. Evidence that mannans of C. albicans are responsible for adherence of yeast forms to spleen and lymph node tissue. Infect. Immun. 61:2578–2584).

EXAMPLE 11

Preparation of Antigen (2ME extract or phosphomannoprotein, which contains the adhesins)

2-ME extract of C. albicans strain CA-1 was isolated and used for immunization by inserting the 2ME extract within liposomes.

1. Medium:GYEP broth

Glucose 2%

Yeast extract 0.3%

Peptone 1%/per liter

2. *C. albicans* strain

Strain CA-1 culture by 4 to 6 times transferring into a fresh medium (GYEP) was used as a starter culture. 5 ml of the culture was inoculated into 1.2 liter GYEP broth medium, incubated at 37° C. under constant aeration by rotation of flasks at 180 rpm, incubated 22–28 h.

3. Extract (how to prepare the 2-ME extract.)

2-ME Extraction of the Surface of *C. albicans*

Recommended tubes, rotors, etc. vary with batch size.

1. Count a 1:100 dilution of the GYEP yeast culture. Estimate the total number of cells and wet weight in the culture $10^{10}$ cells/g wet weight). Alternatively weigh the centrifuge tube before and after collecting the pellet to determine yeast wet weight. [Grams wet weight is used in steps 8 and 9 below to determine the required volumes of 0.1M EDTA pH 9.0 and mercaptoethanol.]
2. Pellet Candida for 10 min. by centrifugation at 2,500×g, 4–6° C.
3. Wash the pelleted cells 2× with cold deionized water ($dH_2O$).
4. Suspend the washed cells in 250 ml of $dH_2O$.
5. Pellet the cells by centrifugation at 5,000×g for 10 min. and discard the supernatant liquid.
6. Suspend the cells in 250 ml of cold 0.1M ethylenediamine tetraacetic acid (EDTA), pH 7.5.
7. Pellet the cells at 5,000×g for 5 min and discard supernatant material.
8. Suspend to 2.0 ml/g. wet weight in 0.1M EDTA pH 9.0, at room temperature.
9. In a fume hood, add 2-mercaptoethanol to 0.3M to the cell suspensions, cap tightly and invert to mix.
10. At room temperature, mix (by inverting the tube) every 5 min. for 30 min.
11. Pellet the cells at 5,00033 g for 10 min.
12. Collect the supernatant material and centrifuge the supernatant at 5,000×g until the supernatant material (2-ME extract) is clear.
13. Dialyze the 2-ME extract against cold $dH_2O$, change the wash every 2–6 hours until the odor of 2-mercaptoethanol is no longer apparent.
14. Concentrate by lyophilization. The dried product is referred to as the 2-ME extract. The 2-ME extract contains the phosphomannoprotein complex. *Candida adhesins* are contained within the mannan portion of the complex.

At concentrations less than 1 µg/ml, the 2ME extract blocks binding of hydrophilic yeast cells to the splenic marginal zone macrophages. In addition, latex beads coated with the 2ME extract bind to the splenic macrophages in a pattern identical to that of whole yeast cells. The activity of the adhesins in the 2ME extract is not affected by boiling or proteolytic enzymes, but is destroyed by periodate oxidation and α-mannosidase digestion.

These data strongly indicate that the adhesins are glycans, probably mannan, and not proteins. In addition, the 2ME extract can be fractionated further by proteinase K digestion and con A-affinity chromatography to yield an adhesin fraction, termed Fr.II that is practically devoid of detectable protein, yet retains full adhesin activity (Kanbe, T., et al. 1993. Evidence that mannans of *C. albicans* are responsible for adherence of yeast forms to spleen and lymph node tissue. Infect. Immun. 61:2578–2584).

The mannan nature of the adhesins is further supported by subsequent purification work which showed the adhesin activities to be associated with the mannan portions of the phosphomannoprotein (PMP). The PMP was degraded by mild acid hydrolysis, and the released oligomannosyl side chains were size separated by P-2 column chromatography (Li, R. K., et al. 1993. Chemical. definition of an epitope/adhesin molecule on *C. albicans*. J. Biol. Chem. 268:18293–18299).

By use of mAb 10G (available from the lab of Dr. Cutler), a tetramannosyl chain was identified as the epitope to which mAb 10G is specific. The tetramannosyl is a β-1,2-linked straight-chained tetramannose and is one of the adhesin sites in the PMP. The purified tetramannose blocks binding of yeast cells to the splenic marginal zone, and latex beads coated with the epitope bind to the marginal zone in a pattern essentially identical to yeast cell binding. This work represents the first identification to structure of an adhesin on the surface of *C. albicans*.

Further analysis of the acid-stable portion of the PMP revealed that adhesin activity is also associated with this part of the complex (Kanbe, T., et al. 1994. Evidence for adhesin activity in the acid-stable moiety of the phosphomannoprotein cell wall complex of *C. albicans*. Infect. Immun. 62:1662–1668).

The inventors induced in mice an antibody response against 2-ME extract and have obtained nine mAbs specific for this fraction. A simplified model of cell wall phosphomannoprotein (PMP) of *C. albicans* serotype B based on a structure by others is available (Kobayashi, H., et al. 1990. Structural study of cell wall phosphomannan of *C. albicans* NIH B-792 (serotype B) strain, with special reference to $^1H$ and $^{13}C$ NMR analyses of acid-labile oligomannosyl residues. Arch. Biochem. Biophys. 278:195–204). The number of mannose units in each oligomannosyl side chain ranges from 1–7.

The 2ME extract was then formulated into liposomes to test its effectiveness as a vaccine. The method of preparing the liposomes is set forth below.

EXAMPLE 12

Preparation of multilamellar liposomes contained 2-ME extract (L-2ME) or PBS (L-PBS).

Materials:

1. Cell wall antigens (2-ME extract)
2. L-α-phosphatidylcholine (L-α-lechithin): Type XI-E, from frozen egg yolk, P-2772 (Lot#- 112H8362), chloroform solution (100 mg/ml), Sigma, St. Louis, Mo.
3. cholesterol: 99% grade, FW=386.7, C-8667 (Lot #-110H8473), chloroform solution (100 mg/ml), Sigma.
4. chloroform: 9180-01, J. T. Baker, Phillipsburg, N.J.
5. methanol: A452-4, Fisher Chem.
6. PBS: Dulbecco's phosphate buffered saline, pH=7.4, Sigma.

Procedures:

1. Put 200 µl of phosphatidylcholine and 30 µl of cholesterol in chloroform solutions into 10 ml methanol/chloroform (1:1) contained in a 500 ml round bottom flask.
2. Evaporate at 37° C. (indicator=set at 2) at low vacuum rotation until a thin layer film forms on the interior of the flask.
3. Dissolve the dried lipid film in 10 ml chloroform and remove the chloroform by low vacuum rotary evaporation at 37° C.
4. Add 5 ml of PBS containing 10 mg of the solubilized cell wall antigen (2-ME extract) to the flask.
5. Disperse the lipid film layer into the 2-ME extract solution by gentle rotation at room temperature for 10 min. For empty control liposome (L-PBS), disperse the thin film in 10 ml PBS only.
6. Hold the suspension at room temperature for 2 hrs. and then sonicate at 20° C. in a water bath sonicator (FS5, Fisher Scientific) for 3 min.

7. Maintain the suspension at room temperature for another 2 hrs. to allow swelling of the liposomes.

8. Centrifuge at 1,000×g (3,000 rpm with SS34, Sorvall RC-5 B Refrigerated Superspeed Centrifuge, DuPont) for 30 min at 16° C. to remove non-liposome associated antigen from liposome encapsulated 2ME-extract.

9. Suspend the liposome in 10 ml PBS and centrifuge again. Repeat these procedures two more times.

10. The liposome-encapsulated 2-ME extract is finally suspended in 4 ml PBS and stored at 4° C. under nitrogen.

11. Determine the amount of 2-ME extract entrapped in liposomes. The liposome-2-ME extract complex should show a yellowish color by the phenol-sulfuric acid test for carbohydrates, thus indicating the presence of 2-ME extract in the liposomes. The phenol-sulfuric acid procedure (Dubois) is done as follows: place 60 µl of the liposome-2ME extract preparation into a well of a microtiter plate and mix with 30 µl of 5% phenol solution. Incubate the mixture at 21–23° C. for 2 min and add 120 µl of concentrated sulfuric acid. Observe a color change from colorless to yellow for the positive reaction. Read the color change at an optical density of 490 nm. By use of this optical density (OD) was compared to the standard dilutions of 2-ME-extract in PBS. The results were as follows:

| Amt. of 2-ME per 5 ml PBS | O.D. at 490 nm |
| --- | --- |
| 1. 10 mg/5 ml | 0.318 |
| 2. 5 mg/5 ml | 0.159 |
| 3. 2.5 mg/5 ml | 0.078 |

As determined by the Dubois (phenol-sulfuric acid) test for carbohydrates the amount of 2-ME extract entrapped in liposomes was 178 µg per 0.2 ml of the preparation. Varying amounts of adhesin fractions may be added during formation of the liposomes to determine the effect on final adhesin concentration that becomes complexed.

EXAMPLE 13

Liposomes made of phosphatidycholine/cholesterol which contained 178 µg of 2ME extract per 0.2 ml preparation were used as the vaccine preparation. Mice were immunized by giving 5 weekly intravenous (i.v.) injections of varying doses (0.1–0.3 ml) of the liposome-2ME extract per animal. One group of mice received 0.2 ml of the preparation on days 1, 3, 5 and 10, and then weekly for two more weeks. Control mice received either liposomes prepared with the 2ME extract diluent (phosphate-buffered saline, PBS), PBS alone, or an equivalent amount of 2ME extract in PBS. Each week, the animals were bled and tested for agglutinins by determining if the sera agglutinated whole yeast cells or latex beads coated with the 2ME extract. Mice immunized weekly for 5 weeks with 0.1 ml or 0.2 ml of the preparation gave the highest agglutinin titers (agglutinin titers were consistently about 40). Mice immunized against 2ME extract in PBS produced titers less than 5, or none at all.

Thus the liposome-encapsulation method of antigen presentation induces in mice polyclonal antisera against antigens within the 2ME extract including candida adhesins, and will allow for subsequent isolation of mAbs against these antigens. (The inventors have been able to perfect the vaccine such that a liposome is not required.)

Liposome-encapsulated 2ME extract promotes strong antibody responses, but the 2ME extract alone is not very immunogenic in mice. Adjuvants, such as those of Ribi (Ribi Adjuvant System) and Hunter (TiterMax) are not very effective in inducing mice to make antibody against the glycan moieties with the 2ME extract. Less than 50% of the mice sensitized against the 2ME extract-Ribi adjuvant combination produced a slight antibody response, and none of the animals responded when the Hunter adjuvant was used.

A very significant advance was made upon the finding that liposome-encapsulated 2ME extract promotes a strong anti body response in 100% of th e immunized mice. The mechanism by which liposomes cause a heightened antibody response is unknown, but in work unrelated to ours, others have also obtained excellent results with this approach (Livingston, P.O., et al. 1993. GD3/proteosome vaccines induce consistent IgM antibodies against the ganglioside GD3. Vaccine II:1199–2004; Wetzler, L. M. et al. 1992. Gonococcal sporin vaccine evaluation: comparison for proteosomes, liposomes, and blobs isolated from rmp deletion mutants., J. Infect. Dis. 166:551–555).

EXAMPLE 14

Production of mabs against cell surface antigens of *C. albicans*. One of the mAbs (mAb 10G) is specific for an adhesin site in the acid-labile portion of the PMP contained in the 2-ME extract and the inventors have obtained nine new mabs against the 2-ME extract. Fusion, cloning and selection methods have been used extensively and described in detail (Brawner, D. L., et al. 1984. Variability in expression of a cell surface determinant on *C. albicans* as evidenced by an agglutinating monoclonal antibody. Infect. Immun. 43:966–972; Cutler, J. E., et al. 1994. Production of monoclonal antibodies against mannan determinants of *C. albicans*, B. Maresca and G. S. Kobayashi (ed.), In: Molecular Biology of pathogenic fungi; A Laboratory Manual. Telos Press, p.197–206; and Li, R. K., et al. 1991. A cell surface/plasma membrane antigen of *C. albicans*. J. Gen. Microbiol. 137:455–464).

Cell-mediated immunity may not be important in resistance to disseminated candidiasis. Some investigators have reported that macrophages are important, while others have found no evidence that macrophages protect (Qian, Q. et al. 1994. Elimination of mouse splenic macrophages correlates with increased susceptibility to experimental disseminated candidiasis. J. Immunol. 152:5000–5008). Perhaps the biggest pitfall in many of these works is that the approaches used to eliminate macrophages were nonspecific.

In the present studies (Qian, Q. et al. 1994. Elimination of mouse splenic macrophages correlates with increased susceptibility to experimental disseminated candidiasis. J. Immunol. 152:5000–5008), mouse splenic macrophages were eliminated by intravenous (i.v.) delivery of liposome-entrapped dichloromethylene diphosphonate (L-Cl$_2$MDP). This liposome conjugate becomes selectively taken up by macrophages, which causes their elimination.

Splenic tissue sections immunoperoxidase stained with mAbs against marginal zone macrophages (mAB MONTS-4), red pulp macrophages (mAB SK39) and neutrophils (mAD SK208) showed that 36 h after L-Cl$_2$MDP treatment, macrophages but not neutrophils were depleted, and circulating neutrophils responded normally to an irritated peritoneum and showed normal phagocytic ability. That is, in response to thioglycollate in the peritoneum, neutrophils migrated in normal numbers to the peritoneal cavity and expressed the normal activation phenotype of high mac-1 (integrin) and low Mel-14 (L-selectin) antigen levels. These neutrophils also showed normal ability to ingest *C. albicans* yeast cells in vitro and in vivo. However, the spleens from L-Cl$_2$MDP-treated mice lost their ability to bind yeasts, which agrees with our previous findings that hydrophilic yeast cells bind specifically to marginal zone macrophages.

When macrophage depleted mice were systemically challenged with *C. albicans*, clearance of viable fungal elements from blood was slower, their kidneys had higher recoverable cfu, and neither BALB/c nor nu/nu mice survived as long as control mice. Mice given L-Cl$_2$MDP recovered most of their macrophage function by 56 days and became normal in their resistance to *C. albicans*.

These results indicate that macrophages play an important role in host resistance to disseminated candidiasis. The similar results obtained with normal mice and the congenitally thymic deficient (nude) mouse indicate that the mechanism of protection by microphages does not involve activation of T-cell functions. This result is important, because it is consistent with earlier reports indicating that cell-mediated immunity may not be critical in resistance of mice to deep-seated or disseminated candidiasis (Mourad, S., et al. 1968. Passive immunization of mice against *C. albicans*. Sabouraudia 6:103–105; Pearsall, N. N., et al. 1978. Immunologic responses to *C. albicans*. III Effects of passive transfer of lymphoid cells or serum on murine candidiasis. J. Immunol. 120:1176–1180). These results did not, however, negate the hypothesis that antibodies play a role in host defense against disseminated candidiasis.

EXAMPLE 15

2ME extract from a *Cryptococcus neoformans* acapsular mutant does not have adhesin activity and serves as a negative control. For negative control purposes a fungal 2ME extract that does not contain candida-like adhesin activity was obtained. Extensive investigations were done on various strains of *Saccharomyces cerevisiae* and on the Ballou mutant strains mnn1, mnn2 and mnn4 (Raschke, W. C. et al. 1973. Genetic control of yeast mannan structure, Isolation and characterization of yeast mannan mutants, J. Biol. Chem. 248:4660–4666). The strains were grown at various temperatures and yeast from different phases of growth were analyzed for their binding characteristics to mouse splenic tissue. These experiments are summarized by stating that *S. cerevisiae* produces some, but not all, of the candida adhesins responsible for yeast cell binding to the splenic marginal zone. To obtain a fungal 2ME extract that did not have the ability to block adherence of *C. albicans* to splenic tissue, the acapsular mutant strain 602 of *C. neoformans* was examined (Kozel, T. R., et al. 1971. Nonencapsulated variant of *Cryptococcus neoformans* 1. Virulence studies and characterization of soluble polysaccharide. Infect. Immun. 3:287–294).

*C. neoformans* strain 602 log and stationary phase cells were removed form the various growth conditions and tested for adherence to splenic tissue in the ex vivo assay. None of these growth conditions yielded adherent yeast cells. Stationary phase cells extracted by the β-mercaptoethanol method gave a water soluble cell wall material that did not affect binding of *C. albicans* yeast cells. That is, in the ex vivo assay, pretreatment of splenic sections with 10 μg, 25 μg and 100 μg of the cryptococcal 2ME extract had no detectable effect on binding of *C. albicans* hydrophilic yeast cells to the marginal zone, as compared to over 95% inhibition of binding due to pretreatment of splenic tissues with 1 μg of 2ME extract from *C. albicans* yeast cells.

The chemical nature of the cryptococcal 2ME extract is apparently mostly glucan (James, P. G., et al. 1990. Cell-wall glucans of *Cryptococcus neoformans* CAP 67. Carbohyd. Res. 198:23–38) which serves as a non-specific control material.

EXAMPLE 16

To test whether *C. albicans* serotype differences are important, the inventors prepared adhesin fractions from serotype A and B strains (CA-1 and A-9, respectively). Both adhesin fractions cause identical dose response inhibition of binding of either serotype A or B strain yeast cells. Data show animals vaccinated against serotype A 2ME extract became protected against disseminated candidiasis by the serotype B strain. Because serotype B strains apparently contain all antigens found on serotype A strains, but serotype A strains have one (or more) cell surface antigens not found on serotype B strains (Hasenclever, H. F., et al. 1961. Antigenic studies of Candida I. Observation of two antigenic groups in *C. albicans*. J. Bacteriol. 82:570–573; and Hasenclever, H. F., et al. 1961. Antigenic studies of Candida II. Antigenic relation of *C. albicans* group A and group B to *Candida stellatoidea* and *Candida tropicalis*. J. Bacteriol. 82:574–577). Most of the adhesin isolations are from the serotype A strain.

EXAMPLE 17

Mice represent the simplest and most accepted experimental mammalian model of human candidiasis. Work derived from the survival and cfu experiments is more directly applicable to human needs than other non-animal studies proposed.

Male and female BALB/c and BALB/c outbred crosses are used to test the ability of various non-toxic vaccine to induce antibody responses. These mouse strains and thymic deficient (nude) mice on a BALB/c background and SCID mice are used for testing the ability of antibodies to protect animals against disseminated candidiasis. In addition, colonies of BALB/c mice crossed with an outbred mouse to yield the vigorous strain (BALB/c ByJ×Cri:CD-1(1CR)BR)F1, and henceforth referred to as CD-1, are also available from Montana State University. Initially, groups of three animals are used to assess the efficacy of the immunizations in terms of antibody titers. The number of animals used is based upon numbers required for statistical analysis. The experiments are evaluated by either fungal colony forming units (cfu) in animal organs retrieved well before ill-effects of the disease are apparent, or by animal survival.

Assessment of the adhesin-liposome preparations in mice. The vaccine preparations are assessed by determining their relative ability to induce antibody responses in mice. In studies it was found that 0.1–0.2 ml of the liposome-2ME extract complex is more immunogenic than other doses, and weekly boosters work best. Work was performed primarily on female BALB/c mice which have relatively high innate resistance to disseminated candidiasis (Hector, R. F., et al. 1982. Immune responses to *C. albicans* in genetically distinct mice. Infect. Immun. 38:1020) and females are somewhat more resistant (Ashman, R. B., et al. 1991. Murine candidiasis; Sex differences in the severity of tissue lesions are not associated with levels of serum C3 and C5, Immunol. Cell Biol. 69:7–10; Domer, J. E. 1988. Intragastric colonization of infant mice with *C. albicans* induces systemic immunity upon challenge as adults. J. Infect. Dis. 157:950–958.).

Control groups: It was found that liposome-buffer (PBS) preparations neither induce antibody responses nor cause increased resistance in mice to disseminated disease, thus in work with BALB/c mice, these controls are omitted. As a control in all studies, mice are immunized against the adhesin fractions prepared in buffer (0.01 M PBS) alone. Doses of adhesin for controls are determined by assessing the concentration of adhesins in the final liposome preparation. The results from these control animals, when compared with liposome-adhesin test mice, provide a better indication of the advantage offered by liposome encapsulation. A reliable determination of 2ME extract adhesin content can be made by the phenol-sulfuric acid method of Dubois for carbohydrate. For adhesins with a high protein content, such as the hydrophobins or adhesins responsible for adherence to endothelial cells, protein assays (such as the BCA, Pierce), are used.

EXAMPLE 18

Immunization of mice against liposome-encapsulated 2-ME extract protects the animals against disseminated candidiasis. BALB/c female mice were immunized against the 2ME extract containing the mannan adhesins by encasing the extract in liposomes as indicated above. Each mouse from groups of 4 mice each were immunized against the liposome-2ME extract conjugate by giving 0.2 ml i.v. once each week for five weeks. All mice produced an agglutinin antibody titer from 20–40 in 100% of the mice as measured by agglutination of 2ME extract-coated latex beads.

Mice immunized against the adhesin fraction showed increased survival times, as compared to PBS controls, when challenged with a lethal dose of $C. albicans$ yeast form cells. Although increased survival was more apparent when mice were challenged with $2.5 \times 10^5$ yeast cells (i.e., 0.2 ml i.v. of a concentration of yeast cells of $12.5 \times 10^5$/ml PBS), slight prolongation of survival was also noted in mice challenged with four times more yeast cells. In a repeat experiment, an additional group of mice was added that received 2ME extract in PBS (the same amount of 2ME extract as complexed within the 2ME extract-liposome vaccine). These animals, which did not produce antibodies, did not show increased survival.

EXAMPLE 19

The inventors use passive transfer experiments to determine if antibodies are responsible for immunity. Immune sera from vaccinated animals, mAbs specific for the 2-ME extract of $C. albicans$, and mAbs against hydrophobic proteins of $C. albicans$ are tested for their ability to protect naive animals against disseminated candidiasis. Immunologically competent mice, T-cell deficient (nu/nu), T- and B-cell deficient (SCID), and mice with induced neutropenia (by use of the anti-neutrophil antibody, mAb RB6-8C5) are tested. The ex vivo assay, the capillary tube shear-dependent adhesin assay, the endothelial adherence assay, and in vivo intravital microscopic methods are used to determine the effect of immune sera and protective mAbs on adherence characteristics of $C. albicans$ to various host cells, tissues and glycoproteins. The effect of immune sera and mAbs on adherence characteristics of complement opsonized cells and unopsonized cells is examined. These results lead to preventative and therapeutic strategies for disseminated candidiasis.

To determine effectiveness of the vaccine, mice were immunized for the five week period to induce antibody responses against the adhesin fraction. They were then rendered immunocompromised by treatment with either mAb RB6-8C5, at 100 μg antibody/mouse i.v., that severely depletes neutrophils in vivo (Czuprynski, C. J., et al. 1994. Administration of anti-granulocyte mAb RB6-8C5 impairs the resistance of mice to Listeria monocytogenes infection. J. Immunol. 152:1836–1846; and Jensen, J. T., et al. 1993. Resistance of SCID mice to $C. albicans$ administered intravenously or colonizing the gut rule of polymorphonuclear leukocytes and macrophages. J. Infect. Dis. 167:912–919), or cyclophosphamide given subcutaneously at 200 mg/kg mouse (Steinshamn, S. et al. 1992. Tumor necrosis factor and interleukin-6 in $C. albicans$ infection in normal and granulocytopenic mice. Infect. Immun. 60:4003–4008).

The neutrophil suppressive effects of both treatments were confirmed by monitoring peripheral blood neutrophil counts, thioglycollate elicited peritoneal exudates, and assessing by FACScan analysis integrins and L-selectins (these techniques are defined in Qian, Q. et al. 1994. Elimination of mouse splenic macrophages correlates with increased susceptibility to experimental disseminated candidiasis. J. Immunol. 152:5000–5008).

At a low dose yeast challenge mice that were first vaccinated, then treated with mAB RB6-8C5 to make them neutropenic, and then challenged with $C. albicans$ were still protected against disseminated candidiasis (as compared to the control mice that received treatment of mAB RB6-8C5 without prior vaccination.

EXAMPLE 20

Immune serum neutralizes adhesins.

Sera from immune animals neutralize adhesin activity and blocks yeast attachment. Sera from vaccinated mice react with the adhesin fraction as evidenced by specific agglutination of adhesin-latex bead conjugates. When splenic sections are pretreated with 0.1 μg or more of the 2ME extract, $C. albicans$ yeast cells will not bind to the tissues (Kanbe, T., et al. 1993. Evidence that mannans of $C. albicans$ are responsible for adherence of yeast forms to spleen and lymph node tissue. Infect. Immun. 61:2578–2584, and our unpublished data).

However, 2ME extract will not inhibit yeast adherence if the extract is treated with antiserum from vaccinated animals. In this experiment, antiserum from BALB/c mice vaccinated against the 2ME extract was heat inactivated (56° C., 30 min) and produced a specific agglutinin titer of 40 against the 2ME extract-coated latex beads. In the test condition, 1 μg, 2 μg and 4 μg of 2ME extract was each mixed for 1 h on ice with a 1:4 dilution of antiserum. 100 μl of each was overlaid onto splenic cryosections for 15 min at 4° C., the mixtures were decanted, 100 μl of a suspension of yeast cells ($1.5 \times 10^7$/0.1 ml DMEM) was added to each tissue section for 15 min at 4° C., and yeast cell binding was quantified as previously described (Riesselman, M. H. et al. 1991. Improvements and important considerations of an ex vivo assay to study interactions of $C. albicans$ with splenic tissue., J. Immunol. Methods 1450:153–160). Binding was compared with control sections pretreated with the 2ME extract concentrations but without antiserum, and with sections pretreated with normal mouse serum (NMS) (positive binding control). On control sections pretreated with 2ME extract at all three concentrations, binding of yeast cells to the marginal zone areas was less than 3% of positive binding control sections in which the pretreatment was NMS alone. An additional control, in which sections were pretreated with antiserum alone, showed that binding was not affected.

In the neutralization test, adherence of yeast cells to tissues pretreated with a combination of either 1 μg 2ME extract or 2 μg 2ME extract+anti-2ME extract antiserum was essentially the same as the positive binding control, and adherence was slightly reduced when tissues were pretreated with a combination of 4 µg 2ME extract+the antiserum.

When the mouse polyclonal anti-adhesin serum is mixed with yeast cells during their addition to the splenic tissues, yeast cell binding to the marginal zone macrophages is reduced. Addition of 25 or 50 µl of the anti-adhesin per 100 µl total of yeast cell suspension reduced by over 80% yeast cell binding in the ex vivo assay. Addition of 10 µl reduced binding by about 30%. NMS controls had no effect on binding.

The data from the above experiments indicate that the polyclonal antiserum produced in mice against the 2ME extract contains antibodies that neutralize candida adhesins responsible for yeast cell binding to the marginal zone, the antibodies also block yeast cell attachment and the blocking ability of the antiserum appears to be dose dependent.

EXAMPLE 21

Evidence that immune serum transfers protection. In an experiment, immune serum (i.e., anti-2ME extract) was obtained from 20 vaccinated (the five week protocol) BALB/c mice. NMS was collected from mice that received an equal number of injections of PBS. Three groups of normal naive BALB/c mice (three/group) were given the following: Group 1 received 0.5 ml of immune serum i.p. on Day 1; Group 2 mice received 0.5 ml NMS from PBS-treated animals; Group 3 mice did not receive serum. Four hours later, each mouse was challenged i.v. with $5 \times 10^5$ yeast cells. The following day, the appropriate mice received either 0.2 ml antiserum, NMS or PBS. At the yeast cell challenge dose, it was expected that normal mice would begin to die of disseminated candidiasis by day 9 or 10 and all mice should die by day 20. In this experiment, however, the animals were sacrificed 48 h after challenge and the spleen, kidneys, liver and lungs were removed, homogenized in sterile saline (hand-held glass tissue homogenizer) and plated onto Mycosel agar for cfu. The tissue homogenization does not cause measurable death of fungal elements (Poor, A. H. et al. 1981. Analysis of an in vivo model to study the interaction of host factors with *C. albicans*. Infect. Immun. 31:1104–1109).

As can be seen in Table 3, cfu from organs of mice that received immune serum were less in all organs with the most striking differences noted in the kidneys. These data suggest that immune serum contains factors that may protect mice against hematogenous disseminated candidiasis.

TABLE 3

Evidence that anti-adhesin serum transfers protection against disseminated candidiasis to naive mice.

| Organs | Colony forming units (cfu) (±SD of coefficient)/g tissue homogenate | | |
|---|---|---|---|
| | Immune Serum | Normal Serum | No Serum |
| Spleen | $0.6 \times 10^4 \pm 0.5$ | $1.5 \times 10^4 \pm 0.4$ | $1.3 \times 10^4 \pm 0.1$ |
| Kidneys | $2.1 \times 10^4 \pm 1.4$ | $5.2 \times 10^4 \pm 1.7$ | $4.2 \times 10^4 \pm 0.3$ |
| Liver | $1.5 \times 10^3 \pm 0.3$ | $3.1 \times 10^3 \pm 1.8$ | $2.5 \times 10^3 \pm 0.6$ |
| Lungs | $2.3 \times 10^2 \pm 0.4$ | $2.9 \times 10^2 \pm 0.6$ | $2.8 \times 10^2 \pm 0.4$ |

EXAMPLE 22

Measurement of antibody responses:

Mouse polyclonal anti-2ME extract caused agglutination of whole yeast cells. Latex beads coated with the 2ME extract as previously reported, (Li, R. K., et al. 1993. Chemical definition of an epitope/adhesin molecule on *C. albicans*. J. Biol. Chem. 268:18293–18299), agglutinate strongly in the presence of the polyclonal antisera, whereas no agglutination occurs in the presence of normal mouse serum (NMS), and agglutination of the 2ME extract-latex is blocked by addition of soluble 2ME extract. Latex agglutination titers of the various sera are determined by adding 25 µl of the 2ME latex conjugate, mixing by rotation for 2–5 min and determining the agglutination end-point.

An anti-adhesin ELISA assay was also developed. Because of its sensitivity and ability to simultaneously test many different samples, the ELISA will be especially useful in characterizing the predominant class of immunoglobulins produced in protective sera as indicated below. Coating microtiter plates with 2ME extract or Fr.II readily occurs in the presence of 0.06M carbonate buffer (pH 9.6); 3% BSA neutralizes non-specific binding. Confirmation of adhesin binding to the plates is accomplished by demonstrating specific reactivity with the adhesin-specific mAb 10G as detected by commercial secondary anti-mouse Ig-enzyme and substrate; showing that mAb 10G does not bind to the plates in the presence of soluble 10G antigen or 2ME extract; and, binding of an irrelevant mAb or NMS is low. It was found that 2ME extract-coated plates may be stored indefinitely at 20° C.

Tail vein blood from vaccinated mice was evaluated for antibody titers (anti-Ig) on a weekly basis during the five weeks of vaccinations-boosters. After that time titers will be determined every three weeks until antibody levels decline near background. Various classes/subclasses of antibodies in the antisera will also be titered by use of the ELISA assay. Commercially available enzyme-labeled antibodies specific for the various mouse Ig heavy chains will be used. This experiment will be of interest later if, for example, IgM anti-adhesins are found in high titer in mice that are protected, as opposed to $IgG_{2b}$ that might predominate in mice poorly protected.

EXAMPLE 23

Pools of mAbs specific for candida adhesins are also used for passive transfer. Ascites fluid of each mAb and their concentrated Ig fractions obtained by use of an ABx HPLC preparative column are available. This column works very well for isolation of IgM and IgG classes of mAbs. Dr. Hazen provided the mAbs specific for hydrophobic adhesins of *C. albicans*.

Mice (initially BALB/c females) are given various doses of pools of mAbs against the various adhesins. The protocols chosen are roughly deduced from results obtained with polyclonal antiserum experiments. After establishing antibody titers, the animals are challenged with appropriate doses of *C. albicans* and organ cfu determined at various times after challenge. Control animals receive mAbs known to react with the cell surface of *C. albicans*, but have been shown not to react with adhesin sites (e.g., mAb 2B3.1). Mab H9 (Brawner, D. L., et al. 1984. Variability in expression of a cell surface determinant on *C. albicans* as evidenced by an agglutinating monoclonal antibody. Infect. Immun. 43:966–972; and Brawner, D. L., et al. 1986. Variability in expression of cell surface antigens of *C. albicans* during morphogenesis. Infect. Immun. 51:337–343) reacts with a candida carbohydrate surface epitope not involved in adhesion events (our unpublished data).

Control mAbs (2B3.1 and H9) and our anti-adhesin mAb (mAb 10G) are of the IgM class. Isotype switching work can be performed as known in the art (Schlageter, A. M. et al.

1990. Opsonization of Cryptococcus neoformans by a family of isotype-switch variant antibodies specific for the capsular polysaccharide. Infect. Immun. 58:1914–1918) if required to provide specificity for monoclonal antibodies of the invention.

The number of different kinds of mAbs in the pooled mAb preparations are systematically dissected to determine the minimum number required for protection.

EXAMPLE 24

The effects of anti-adhesins on attachment phenomena was investigated. Sera from vaccinated mice inhibits the adhesins (2ME extract) from binding to splenic marginal zone tissue and the antiserum also prevents attachment of hydrophilic yeast cells to the spleen.

As Ig fractions of antisera and mAbs become available, approaches are used similar to those already applied in the ex vivo assay to test the effect of antisera (anti-sMB extract) on yeast cell adherence to the splenic marginal zone. The various polyclonal antisera and mabs are selected based upon preliminary results. Their effects, either singly or in combination, on tissue adherence of hydrophilic and hydrophobic yeast cells, complement-coated yeast cells and adhesin-producing recombinant C. albicans strains are determined. The systems used for study and comparison include the ex vivo assay, the endothelial assay and the capillary shear-dependent adhesion assay. Intravital microscopy is used to follow yeast cell endothelial interactions within mice that have been vaccinated and in non-sensitized mice given polyclonal and mabs. In all of these methods, careful consideration is given to appropriate controls. Depending on the experiment, non-binding yeasts such as C. neoformans or S. cerevisiae transformed with plasmid only are used as negative binding controls. NMS and isotype-matched irrelevant mAbs are used as negative controls for immune polyclonal antisera and mAbs, respectively. The detailed use of these various adherence techniques and data acquisition/evaluation methods are given in the respective proposal from each investigator and/or their publications.

The pathogenesis of hematogenous disseminated candidiasis appears to involve adhesion events between yeast cells of C. albicans and specific host tissues. Host antibodies specific for candida adhesins alter the pathogenesis and may aid host survival. Candida adhesins have been isolated that cause specific yeast cell adherence to mouse splenic marginal zone macrophages. These adhesins are part of the phosphomannoprotein (PMP) complex on the candida cell surface. Vaccines made of solubilized adhesins encapsulated in liposomes provoke antibody responses in mice against the adhesins. Vaccinated animals have increased resistance against disseminated candidiasis, their serum neutralizes adhesin activity, prevents yeast cell attachment to the spleen and appears to transfer protection. Monoclonal antibodies (mAbs) against the PMP-derived adhesins are available from Dr. Cutler. The effects of polyclonal and mAbs on adherence interactions with various tissues are extensively evaluated by adherence assays.

The vaccine may be formulated in liposome formulations as set forth above. Additional formulations may be prepared as with formulations and adjuvants as known in the art (see Remingtons Pharmaceutical Sciences, 18th ed., Mack Publishing Co., 1990). Vaccines may include from 0.01 to 99.00% by weight adhesin composition. The vaccine of the present invention may, in a preferred embodiment, be formulated in an effective amount of about 0.5 g per human of 150 lbs.

EXAMPLE 25

Organisms, culture conditions and isolation of the adhesin fraction.

C. albicans serotypes A (strain CA-1) and B (strain A9) were used and previously characterized (8,20,21,49). C. tropicalis strain CT-4 is from Montana State University stock collection and species identification was confirmed by API 20C Yeast Identification Strips (Analytab Products, Plainview, N.Y.). Stock cultures were stored and maintained as described (19,20) and grown to stationary phase in GYEP broth (19,20) at 37 C. The yeast cells were washed three times in sterile deionized water, suspended to the appropriate concentration in sterile Dulbecco's phosphate buffered saline (DPBS) (Sigma Chem. Co., St. Louis, Mo.), and used to challenge mice.

The PMC (referred to as the adhesin extract) was obtained in crude form, as before (19,20), by a β-mercaptoethanol extraction of the serotype A isolate of C. albicans. Less than 1 mg of this extract inhibited adherence of yeast cells to splenic and lymph node macrophages, hence, it contains the adhesins (17,20). Chemically, the extract is primarily mannan with about 3.5% protein. Following proteinase digestion, the protein content dropped to 0.47%, yet all adhesin activity was retained (20).

I.II.Liposome encapsulation of the adhesin extract.

The adhesin extract was encapsulated into multilamellar liposomes as described previously (11). Briefly, 200 µl of phosphatidylcholine (100 mg phosphatidylcholine/ml chloroform) and 30 µl of cholesterol (100 mg cholesterol/ml chloroform) (molar ratio of phosphatidylcholine/cholesterol at approximately 3.2:1) were combined into 10 ml of chloroform-methanol (1:1) in a 500 ml round bottom flask. The solution was dried as a thin film by rotary evaporation at 37 C under reduced pressure. The film was dissolved in 10 ml of chloroform, evaporated again, dispersed at room temperature for 10 min in 5 ml DPBS containing 10 mg of the adhesin extract, allowed to stand for 2 h, sonicated for 3 min and held at room temperature for an additional 2 h. To separate non-liposome associated antigen from liposome encapsulated antigen, the preparation was sedimented by centrifugation at 1,000×g for 30 min. The pelleted liposomes were suspended in 5 ml DPBS, pelleted again and this process was repeated two more times. The liposome-encapsulated adhesin extract, referred to as L-adhesin, was finally suspended in 4 ml DPBS and stored at 4 C under nitrogen for up to 2 weeks. The amount of adhesin extract within the L-adhesin was 178 mg/ml as determined by the phenol-sulfuric acid reaction (12). Control liposomes were prepared exactly as above, but buffer (DPBS) without adhesin extract was added during the preparation. These control liposomes are referred to as L-PBS.

Vaccination and challenge of mice.

In all experiments mice were used and housed in accordance with institutional regulations in an AAALAC certified animal facility. BALB/cByJ (Jackson Labs, Bar Harbor, Me.) female mice, 6–7 weeks old, received the initial vaccine and weekly booster immunizations. Each injection consisted of 0.2 ml of the liposome-adhesin complex (L-adhesin) administered intravenously (i.v.). Anti-adhesin titers in mouse sera were assessed by slide agglutination against latex beads coated with the adhesin extract. Adhesin coating was done as before (19,20,27). When the agglutinin titers reached 40 or more (usually by the 4 th booster), the animals were challenged. Control mice received an equal volume and number of injections consisting of diluent (DPBS) only prior to challenge. The mice were challenged i.v. with viable yeast cells prepared to the appropriate concentration in 0.2 ml DPBS.

Treatment of polyclonal antiserum.

To characterize the nature of the protective factor(s) in antiserum, polyclonal antiserum was obtained and pooled from vaccinated mice. The serum fraction was either immediately stored at −20 C, heated at 56 C for 30 min prior to use, or adsorbed five times with formalin killed washed C. albicans strain 1 yeast cells at a ratio of ten volumes antiserum to one volume DPBS-washed packed dead yeast cells.

The antiserum was also fractionated by passage through an ABx HPLC column (J. T. Baker, Phillipsburg, N.J.) as described (40) to obtain pools of various separated serum components, including a fraction which contained all of the agglutinin activity. Briefly, buffer A consisted of 25 mM MES (2-[N-Morpholino]ethanesulfonic acid) (Sigma), pH 5.2–5.8 and buffer B was 1M sodium acetate, pH7.0. One part of polyclonal antiserum was mixed with two parts buffer A and the mixture was loaded onto the ABx column with buffer A at a flow rate of 1.5 ml/min and each fraction was 40 drops. At ten minutes, the percent of buffer B was brought to 20, at 15 min buffer B was brought to 50%, at 20 min it was brought to 70%, at 25 min it was brought to 100% and was retained at 100% until 55 min at which time the run was terminated. Each of the peaks detected by absorption at 280 nm was collected, dialyzed against at least 100 volumes of DPBS at 4 C with a minimum of four changes of DPBS over a 36 h period, and each pooled fraction was concentrated by ultrafiltration (PM30 Diaflo Ultrafiltration membrane, Amicon Division, Beverly, Mass.). Each concentrated fraction was brought to approximately one-half of the original starting volume of antiserum applied to the column. Each was tested for the ability to agglutinate whole yeast cells and latex beads coated with the adhesin fraction.

Passive transfer experiments.

Normal mouse serum (control), polyclonal antisera, antisera heated at 56 C, C. albicans-adsorbed antisera and HPLC-fractionated polyclonal antisera were tested for their ability to transfer resistance against disseminated candidiasis to naive mice. For each condition, 7–8 week old female or male BALB/cByJ mice (Jackson Labs) were given 0.5 ml of the test serum intraperitoneally (i.p.), 4 h later they were given 0.2 ml i.v. of a suspension containing $2.5 \times 10^6$ yeasts/ml DPBS and 20 h later they were given i.p. another 0.2 ml of test serum. Forty-eight hours after challenge, candida cfu/g kidney were determined as described below. In some experiments, passive transfer of immune serum and challenge with live yeast cells were done in 18–20 weeks old male SCID mice (BALB/cByJSmn-scid/J, Jackson Labs).

Isolation and characterization of monoclonal antibodies (mAbs).

Mice were immunized with whole yeast cells (4) or the L-adhesin (11) and two mAbs specific for yeast surface epitopes were isolated as before (4,11). MAb B6 has the same specificity as mAb C6 (6) and mAb B6.1 is specific for an epitope in the PMC of C. albicans.

The epitope specificity of mAb B6 differs from mAb B6.1 as evidenced by Ouchterlony lines of non-identity against candida cell wall extracts. Both of the mabs agglutinate C. albicans yeast cells and both are IgM as indicated by reactions with commercial Ig-heavy chain specific antibodies (Sigma).

The mAbs were produced in serum free medium, concentrated by ammonium sulfate precipitation, and suspended and diluted in DPBS to give identical agglutinin titers. The same strategy as described above for polyclonal antiserum was used to determine the ability of mAbs B6 and B6.1 to transfer protection.

In these experiments, the agglutinin titers of each mAb was diluted to 20 (approximately 220 mg/ml for mAb B6.1 and 290 mg/ml for mAb B6) before administration to the BALB/cByJ mice. In one experiment, mAb B6 was obtained from ascites fluid, adjusted to an agglutinin titer of 320 and compared to the effect of mAb B6.1 at a titer of 20.

Assessment of resistance/susceptibility to disseminated candidiasis.

To determine relative susceptibility or resistance to disseminated candidiasis, we used survival curves and/or colony forming units (cfu) per g kidney tissue in mice challenged i.v. with yeast form cells of C. albicans. For survival curves, groups of test and control animals consisted of a minimum of five mice per group. Survival differences between the groups were calculated for statistical significance by the Kolmogorov-Smirnov two sample test (9). The kidney is a target organ in experimental disseminated candidiasis, therefore, C. albicans cfu in kidney tissue may be used as an indicator of disease severity (28,43,46). The cfu determinations were done by homogenizing the kidneys with glass tissue homogenizers as described (43) except that the kidneys were homogenized in 1 ml DPBS and plated onto Mycosel agar (BBL Microbiology Systems, Becton Dickinson and Co., Cockeysville, Md.). Statistical significance of difference between test and control groups was determined by the Student t-test.

Vaccinated mice have increased survival rates.

Vaccinated mice showed more resistance to disseminated candidiasis than did control mice as indicated by an increase in mean survival times following challenge (Table 3). To demonstrate a requirement for liposome delivery, some animals were given i.v. an equivalent amount of adhesin extract (178 mg) in 0.2 ml DPBS, but without liposomes. The mean survival times of these animals did not differ from animals that received only DPBS (data not shown). Serum from vaccinated mice transfers protection.

Pooled polyclonal antiserum from vaccinated mice protected both naive normal BALB/cByJ and SCID mice from disseminated disease. Whereas heat treatment (56 C, 30 min) had no effect on the protective ability of the antiserum, adsorption with C. albicans yeast cells removed the activity.

To determine if the vaccine induces protection against both serotypes of C. albicans and against other Candida species, mice were passively given, as above, the antiserotype A polyclonal antiserum and challenged i.v. with either a serotype B strain of C. albicans ($5 \times 10^5$ yeast cells) or a strain of C. tropicalis ($1 \times 10^6$ yeast cells). Kidneys were removed 48 h later for cfu determinations. Antiserum-treated mice challenged with the serotype B strain had 11.3 ($\pm 2.7$)$\times 10^3$ cfu/g kidney tissue, while normal mouse serum (NMS)-treated mice (controls) had 41.4 ($\pm 7.0$)$\times 10^3$ cfu/g (p<0.001) ($\pm$ are standard error values). Likewise, antiserum-treated mice challenged with C. tropicalis developed 145 ($\pm 16$)$\times 10^3$ cfu/g kidney as compared to 267 ($\pm 34$)$\times 10^3$ cfu/g for NMS-treated controls (p<0.001) ($\pm$ are standard error values).

Two fractions from antiserum transfer protection.

Antiserum separated by use of an ABx HPLC column yielded three major fractions, Fr.I, Fr.II, Fr.III. All of the detectable agglutinin activity was associated with Fr.III. Fr.III gave the strongest evidence for ability to transfer protection, but protective activity was also associated with Fr.II. That is, mice given either normal mouse serum (negative control), unfractionated polyclonal antiserum (positive control), Fr.I, Fr.II or Fr.III and challenged with *C. albicans* i.v. resulted in 109 (±33.3), 40.9 (±2.3), 93.2 (±9.5), 59.2 (±11.4) and 50.9 (±9.7)×$10^3$ cfu/g kidney, respectively (± are standard error values). The differences were significant to p<0.05 when polyclonal antiserum, Fr.II or Fr.III were each compared to cfu/g tissue for animals treated with normal mouse serum. In these experiments, the total amount of protein received by each mouse was 22.4 mg of Fr.I, 3.8 mg of Fr.II and 22.6 mg of Fr.III. The antibody activity (agglutination titer) of Fr.III (22.6 mg) was the same as the agglutinin activity of unfractionated polyclonal antiserum.

MAb B6.1 transfers protection, but mAb B6 does not.

Although both mAbs are strong agglutinins and are of the same class, only mAb B6.1 transferred protection against disseminated candidiasis to naive BALB/cByJ mice. This result was demonstrated by both cfu/g kidney counts and by survival curve analysis. In these experiments, both mAbs were standardized to have the same agglutinin titers as indicated in the Materials and Methods. In one experiment, the titer of mAb B6 was increased to approximately 16 times that of mAb B6.1 and administered to mice in the volumes and schedules as indicated. Even though the agglutinin titers at day 2 after administration were 10 for animals that received mAb B6 and 2 for mice that received mAb B6.1, no protection was observed due to mAb B6 as compared to mice given DPBS prior to yeast cell challenge (data not shown). In the survival experiments, of ten BALB/cByJ mice treated with mAb B6.1, six survived the entire 67 day observation period, whereas all mAb B6 treated mice died by day 25 and all control (DPBS treated) mice died by day 19. Likewise, SCID mice treated with mAb B6.1 survived significantly (p<0.01) longer than control mice. In experiments on BALB/cByJ mice, the 67 day survivors were sacrificed and their kidneys and spleens were plated for candida cfu. No cfu in splenic tissues were detected in any of the animals. However, the kidneys from two of the mice showed cfu development (97.7×$10^3$/g and 207.7×$10^3$/g), whereas no cfu were detected in undiluted homogenates of kidneys from four of the mice.

This work provides strong evidence that antibodies specific for certain cell surface determinants on *C. albicans* aid the host in resistance against disseminated candidiasis. First, mice with enhanced resistance were those that were L-adhesin vaccinated and had agglutinin titers of 40–80. Second, mice vaccinated with only the adhesin extract developed low anti-adhesin titers (less than 5) and showed no enhanced resistance. Third, polyclonal antiserum from vaccinated mice protected naive normal BALB/cByJ and SCID mice from disseminated disease. SCID mice, however, did not make antibodies or develop a protective response as a result of the vaccinations (data not shown). Fourth, heat treatment (56 C, 30 min) had no effect on the protective ability of the polyclonal antiserum, but adsorption with *C. albicans* removed the activity. Fifth, fractionation of the antiserum by an HPLC ABx column yielded a fraction that contained all of the agglutinin activity and this fraction transferred protection to naive animals. Sixth, mice that received mAb B6.1, which is specific for the adhesin extract and is a strong agglutinin of whole yeast cells, developed fewer cfu in their kidneys following challenge and both normal and SCID mice survived significantly longer than control animals. In this experiment, six out of ten of the treated BALB/cByJ animals survived the entire 67 day observation period and four out of six of the survivors appeared to be cured as evidenced by the lack of cfu recoverable from their spleen and kidneys.

The results also show that an antibody with specificity for a cell surface determinant of *C. albicans* may not necessarily protect animals against disseminated disease. These findings explain the variable results earlier workers have obtained regarding the role of antibodies in protection against disseminated candidiasis. Animals that received the agglutinating IgM mAb B6 were just as susceptible as controls to disseminated candidiasis, even when mAb B6 was given at about 16 times the titer of mAb B6.1 with resulting higher in vivo titers than in animals that received mAb B6.1. The inventors have also found two additional mAbs specific for surface determinants that also do not protect (unpublished data). These results support the hypothesis that antibodies of only certain specificities against *C. albicans* are protective.

Strains of *C. albicans* are either serotype A or B and both types can cause disseminated disease (41). In addition, there is an increasing number of candidiasis cases due to other candida species such as *C. tropicalis* (26,32). The vaccine of the present invention induces in mice a response that also protects against disseminated disease due to a serotype B strain of *C. albicans* and against *C. tropicalis*. These data suggest that antiserum from vaccinated mice contains antibodies that are broadly protective.

The inventors have determined that mAb B6.1 also protects mice against serotype B and *C. tropicalis* strains. The explanation for the broad protection of polyclonal antiserum appears to involve antibodies with varying specificities, antibodies with specificity for the B6.1 epitope. Since it has been found that mAb B6.1 also protects SCID mice, neither T nor B cells appear to be involved in the protection.

Not being bound by any one theory, one possible mechanism is that antibodies in the mouse cause simple agglutination of the yeast cells which effectively reduces the number of independent infection units. This explanation does not seem likely because mAb B6 does not protect, but it is a strong agglutinin. In fact, it causes larger agglutinates at a given titer than mAb B6.1 (unpublished observations). In animals that received the mAbs, the agglutinin titers in the serum of mice that received mAbs B6 or B6.1 were essentially the same. The lower cfu in mAb B6.1-treated animals, but not mAb B6-treated mice, also militates against the argument that cfu are artificially reduced because of the presence of serum agglutinins. In addition, animals that passively received mAb B6.1 had enhanced survival as compared to mice that received mAb B6.

Two other possibilities are that mAb B6.1 alters adherence of yeast cells in vivo, and/or enhances phagocytosis of yeast cells by neutrophils and macrophages. The first possibility is under investigation. The mechanism would not involve Fc receptors on phagocytic cells because mAb B6.1 is an IgM. However, mAb B6.1 may promote complement opsonization more efficiently than the non-protective IgM agglutinin, mAb B6.

EXAMPLE 26

BALB/cByJ female mice 6 to 7 weeks old received an initial injection of 0.2 ml of liposome encapsulated Candida adhesion complex (L-adhesion) containing III.178 ug/0.2 ml of adhesion complex and subsequent weekly injections administered i.v. When adhesion agglutination titers reached 40 (usually by the fourth booster injection) the animals were challenged i.v. with viable yeast cells. Control mice received the same volumes of buffer (DPBS) or liposome-PBS (L-PBS) in the same numbers of injections. The results in Table 3 show that mice immunized with L-adhesion were protected against the Candida challenge.

TABLE 4

Mice vaccinated against candida adhesin extract have greater resistance to disseminated candidiasis than control animals[a]

| Challenge dose (CFU) | Vaccine preparation | Mean (SE) survival time (days)[b] | |
|---|---|---|---|
| | | Expt 1 | Expt 2 |
| 1 × 10$^6$ | DPBS | 12.5(1.0) | Not done |
| | L-PBS | 12.0(0.0) | Not done |
| | L-adh | 20.0(2.2) | Not done |
| | | P <0.05 | |
| 5 × 10$^5$ | DPBS | 21.8(4.2) | 19.4(7.9) |
| | L-PBS | 17.3(4.1) | 20.6(9.8) |
| | L-adh | 31.8(4.3) | 46.0(12.8) |
| | | P < 0.05 | P < 0.05 |
| 2.5 × 10$^5$ | DPBS | 25.0(6.7) | 38.2(21.6) |
| | L-PBS | 23.8(8.3) | 46.2(25.5) |
| | L-adh | 32.5(3.8) | 65.8(13.9) |
| | | P < 0.1 | P < 0.05 |

[a]Normal mice were give buffer (DPBS) alone, liposome-buffer (L-PBS), or the liposome-adhesin complex (L-adh) and challenged with various doses of *C. albicans*. Mean survival times for two separate experiments (Expt 1 and Expt 2) were determined, and results from the DPBS and L-adh groups were compared for statistical significance by the Kolmogorov-Smironov one-sample test.
[b]SE, standard error; Expt 1, four mice per group; Expt 2, five mice per group.

Pooled polyclonal antiserum from vaccinated mice protected both BALB/cByJ and SCID mice. The protective ability was heat stable (56° C. for 30 min.). Similar experiments were performed to demonstrate that the protective ability of the antibodies was not strain- or species-specific. Antiserum from mice vaccinated with *C. albicans* serotype A protected normal mice challenged with serotype B of *C. albicans* (5×10$^5$ cells) or a strain of *C. tropicalis* (10$^6$ cells). Kidneys of mice challenged with serotype B contained the following colony forming units (CFU) per gram: antiserum-treated mice (11.3+/−2.7)×10$^3$ and normal serum-treated mice (41.4+/−7.0)×10$^3$. Kidneys of mice challenged with *C. tropicalis* contained the following CFU per gram: antiserum-treated mice (145+/−16)×10$^3$ and normal serum-treated mice (267+/−34)×10$^3$. Both of these differences were statistically significant (p<0.001).

EXAMPLE 27

Monoclonal antibodies prepared against the phosphomannan complex of *C. albicans* were passively protective prophylactically.

Monoclonal antibodies were prepared by standard procedures from mice immunized with whole yeast cells or with L-adhesion (Brawner and Cutler, Infect. Immun. 51: 337–343 (1986); Cutler, Han, and Li, In B. Maresca and G. S. Kobayashi (eds), Molecular Biology of Pathogenic Fungi: a laboratory manual, Telos Press, NY, 1994, pp. 197–206). Female or male BALB/cByJ mice, 7–8 weeks old, were given 0.5 ml of MAb B6.1 (220 ug/mouse) i.p. and 4 hours later were given 0.2 ml of a suspension containing 2.5×10$^6$ yeast cells i.v. MAb B6.1 protected the mice as demonstrated by CFU counts and survival times. A similar experiment showed that MAb B6.1 protected SCID mice.

Monoclonal antibodies also protected against *C. albicans* when used therapeutically.

EXAMPLE 28

BALB/cByJ female mice, 7 weeks old, were given 5×10$^5$ yeast cells i.v. One hour later they received MAb B6.1 or buffer (DPBS) i.p. MAb B6.1 showed therapeutic protection by reduced kidney CFU and by increased survival time of treated mice over controls.

BALB/cByJ female mice, 7–9 weeks old were given estradiol s.c.; 72 hours later they received control buffer (DPBS) or 0.5 ml MAb B6.1 i.p. Four hours later they received 5×10$^5$ *C. albicans* intravaginally and 20 hours later they were given a second injection of MAb or buffer. The vaginas were dissected 48 hours after infection, homogenized, and plated for *C. albicans* CFU. The result shows that MAb B6.1 protected mice against mucocutaneous candidiasis.

The experiment above was repeated with a second MAb. MAb B6 also protected against mucocutaneous candidiasis.

EXAMPLE 29

BALB/cByJ female mice received 5 weekly i.v. injections of L-adhesion vaccine preparation (0.2 ml containing 178 ug of L-adhesion). Estradiol was given s.c. and 72 hours later 5×10$^5$ *C. albicans* were given intravaginally. The vaginas were dissected 48 hours after infection and plated to determine *C. albicans* CFU. The results demonstrate that protection was achieved against mucocutaneous candidiasis by active immunization. These results have been confirmed in repeated experiments.

EXAMPLE 30

Therapeutic immunization with *C. albicans* adhesins protects against preestablished mucocutaneous *C. albicans* infections.

BALB/cByJ female mice were given estradiol s.c. and 72 hours later 5×10$^5$ *C. albicans* were given intravaginally. One hour later the mice were either vaccinated with the L-adhesion vaccine preparation or with liposome buffer (DPBS)(L-DPES) as a control. After 7 days the animals were sacrificed and the vaginal tissue processed to determine the *C. albicans* cfu. The results demonstrate that vaccination after mucocutaneous infection has occurred and has therapeutic value.

EXAMPLE 31

The *C. albicans* adhesion complex was treated with 10 mM HCl at 100 C for 60 minutes. Then it was chromatographed on P-2 size exclusion columns. The complex was separated into two major parts; one was acid stable and the other was the acid labile region. Samples from each peak in the acid labile region were tested for ability to block agglutination of MAb B6.1-coated latex beads by the *C. albicans* adhesion complex. As shown on Table 4, Fractions M3 and M4 were active. Fraction M3 has the highest concentration of the MAb B6.1 epitope (or materials with the strongest affinity for the MAb). M4 also reacted with MAb B6.1, but because fraction M4 also contains some fraction 3, it was concluded that fraction M3 in the acid labile portion of the adhesion complex contains the epitope for MAb B6.1.

The acid stable portion of the adhesion complex contains larger antigenic fragments and can be tested by direct capacity to agglutinate MAb-coated latex beads. Tables 5 and 6 show that MAb B6, but not MAb B6.1, is directed against the acid stable portion of the *C. albicans* adhesion complex.

EXAMPLE 32

Monoclonal antibodies (MAb B6.1) against *C. albicans* adhesion molecules can protect against mucocutaneous *C. albicans* infection when given therapeutically.

Figure 15:
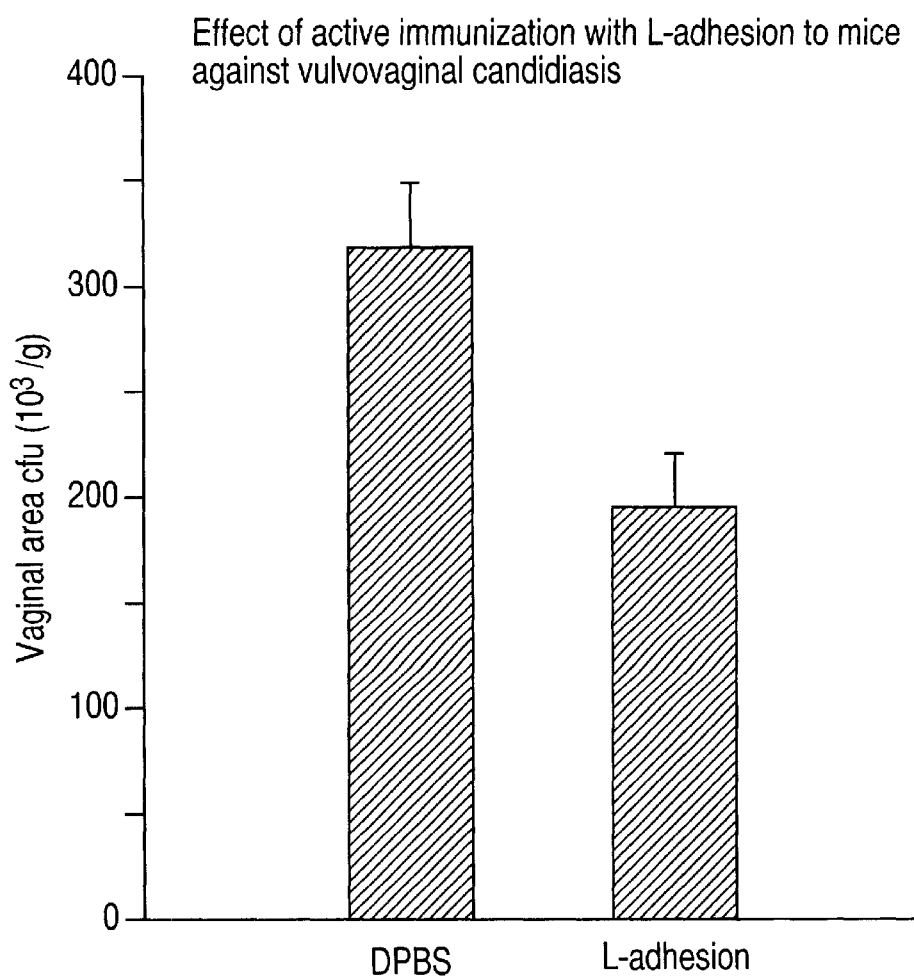
FIG. 15 shows the effect of active immunization with L-adhesion to mice against vulvovaginal candidiasis L=liposome; L02ME=liposome-2ME vaccine prep. Animals received 0.2 ml i.v. (178 μg 2ME in 0.2 ml) weekly for 5 weeks. Estiadiol was given subcu, 72 h later *C. albicia* ($5 \times 10^5$) gives intravaginally, 48 h after infection vaginal cfu determined.
Figure 16:
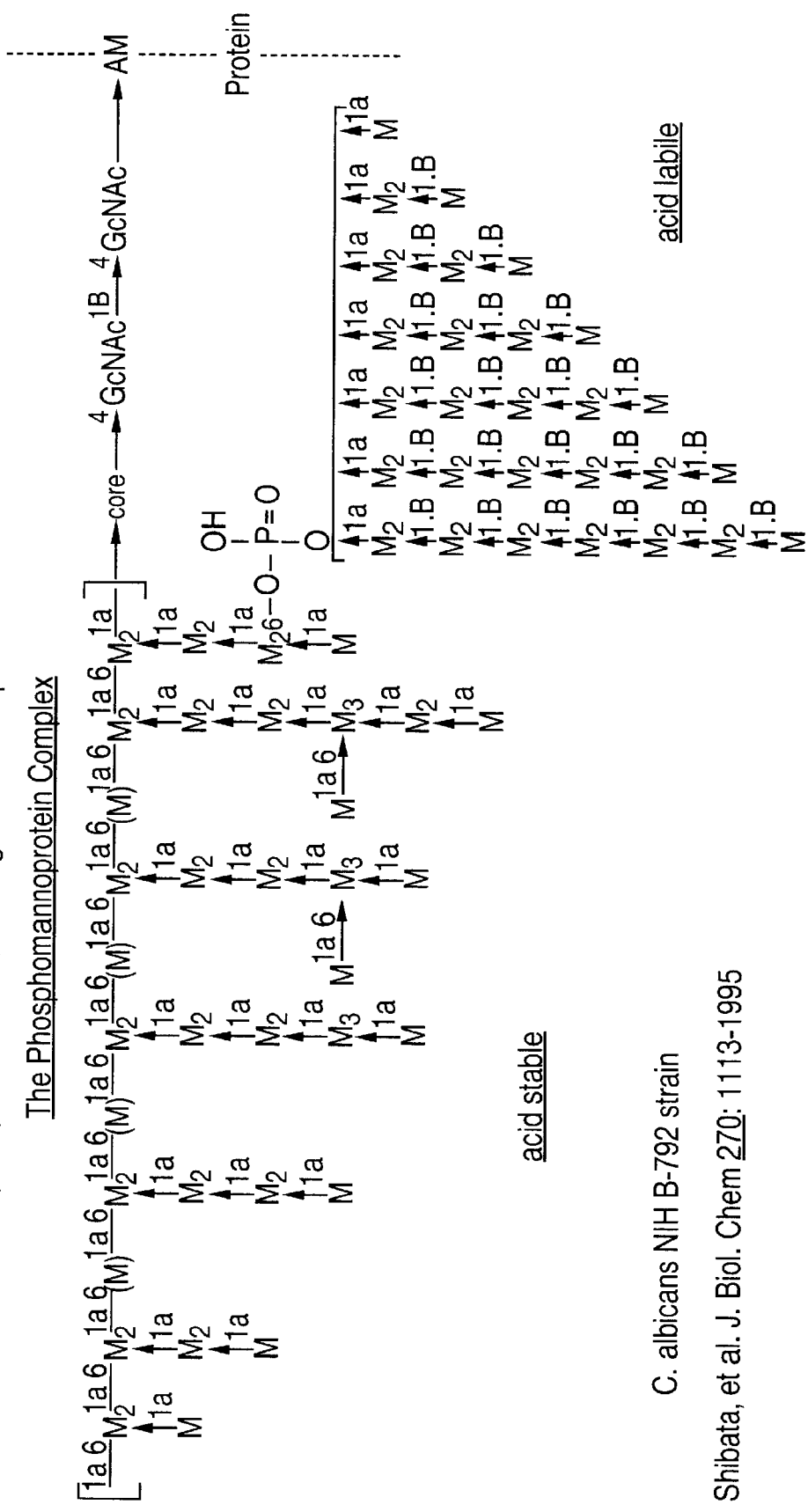
FIG. 16 shows the proposed structure of the phosphomannan complex (PMC)-in this case, n-linkage to cell wall protein is shown.
Figure 17:
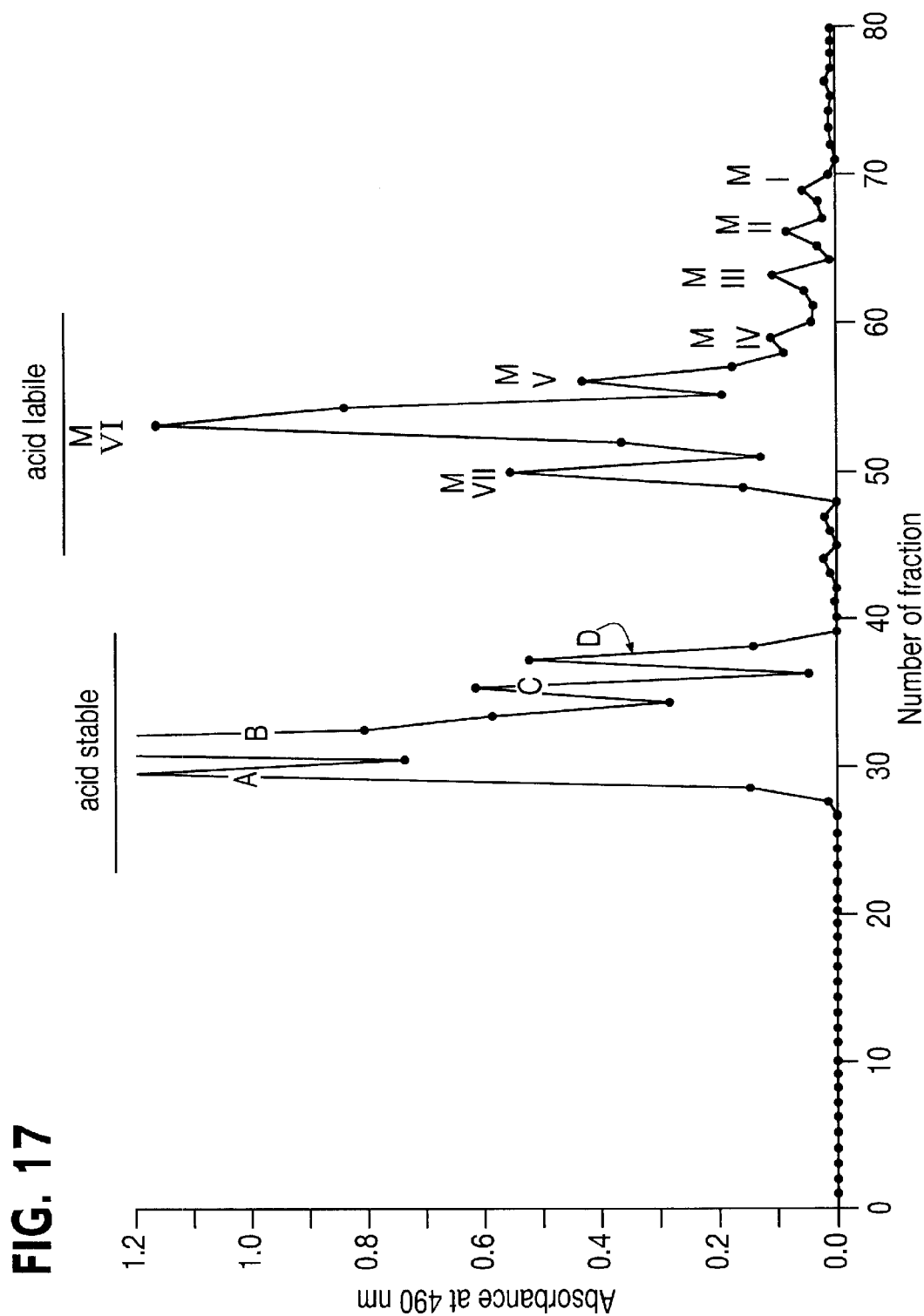
FIG. 17 shows a P-2 size exclusives column. Fractions A-D are the void volume and all react with MAb B.6, but not MAb B6.1.) The 2-M extract was treated with 10 mM HCl, $100°$ C., 60 min. before placing outo column.
Figure 18:
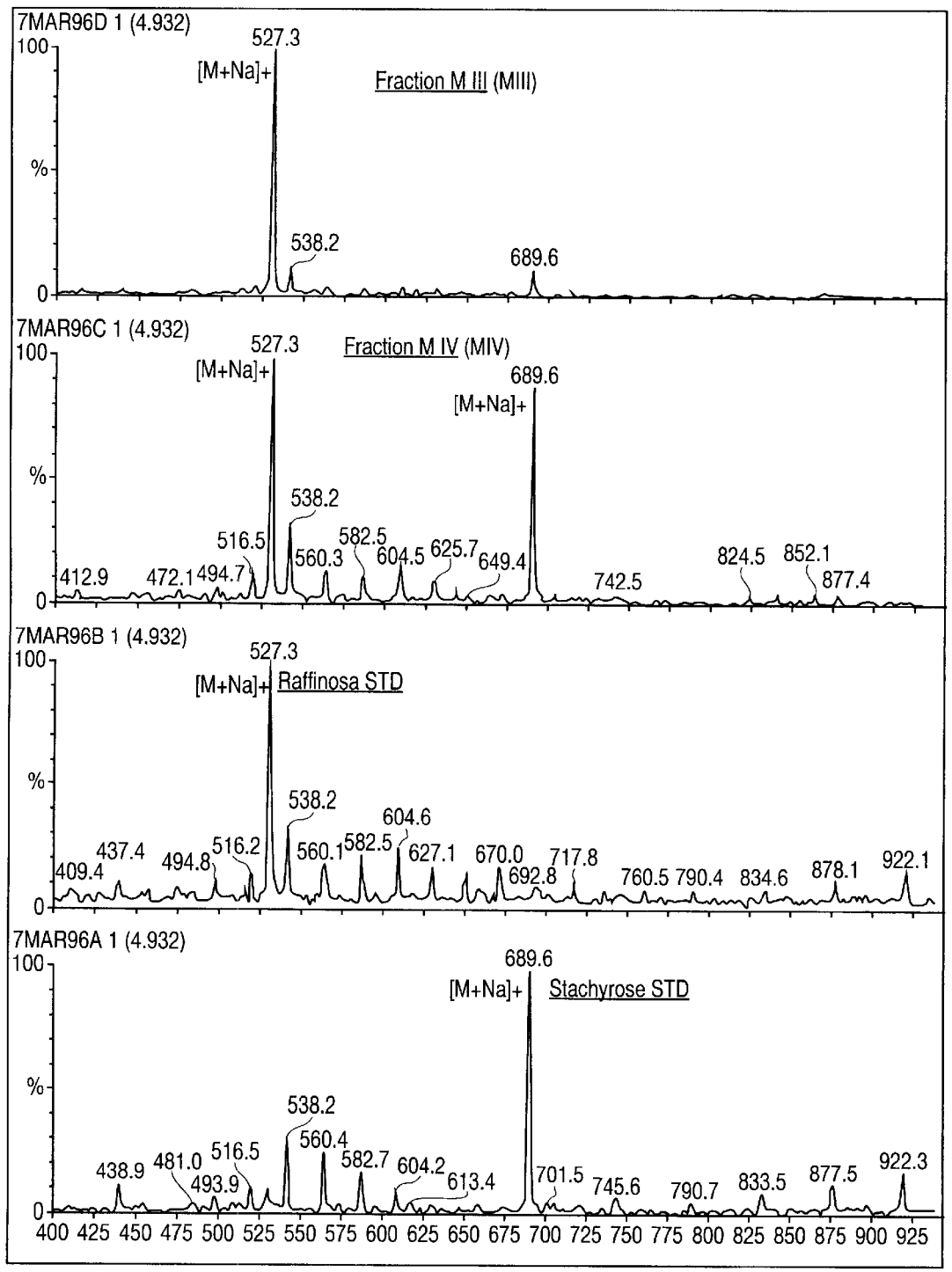
FIG. 18 shows a mass spectra for the mannan portion of the vaccine.
Figure 19:
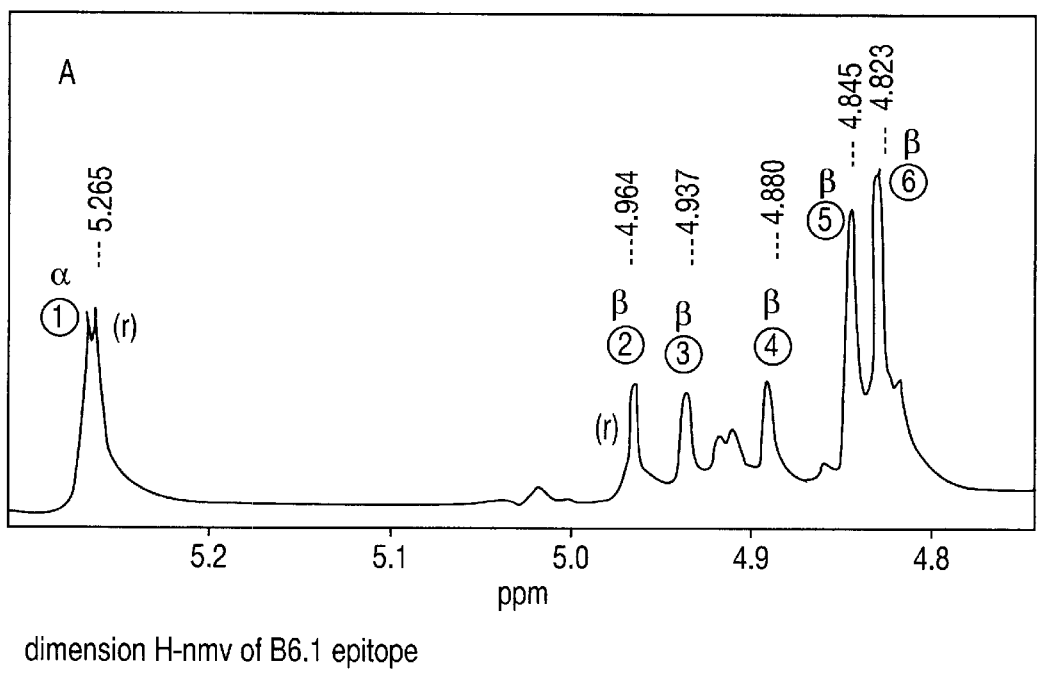
FIG. 19 shows one dimension H-nmv of B6.1 epitope
Figure 20:
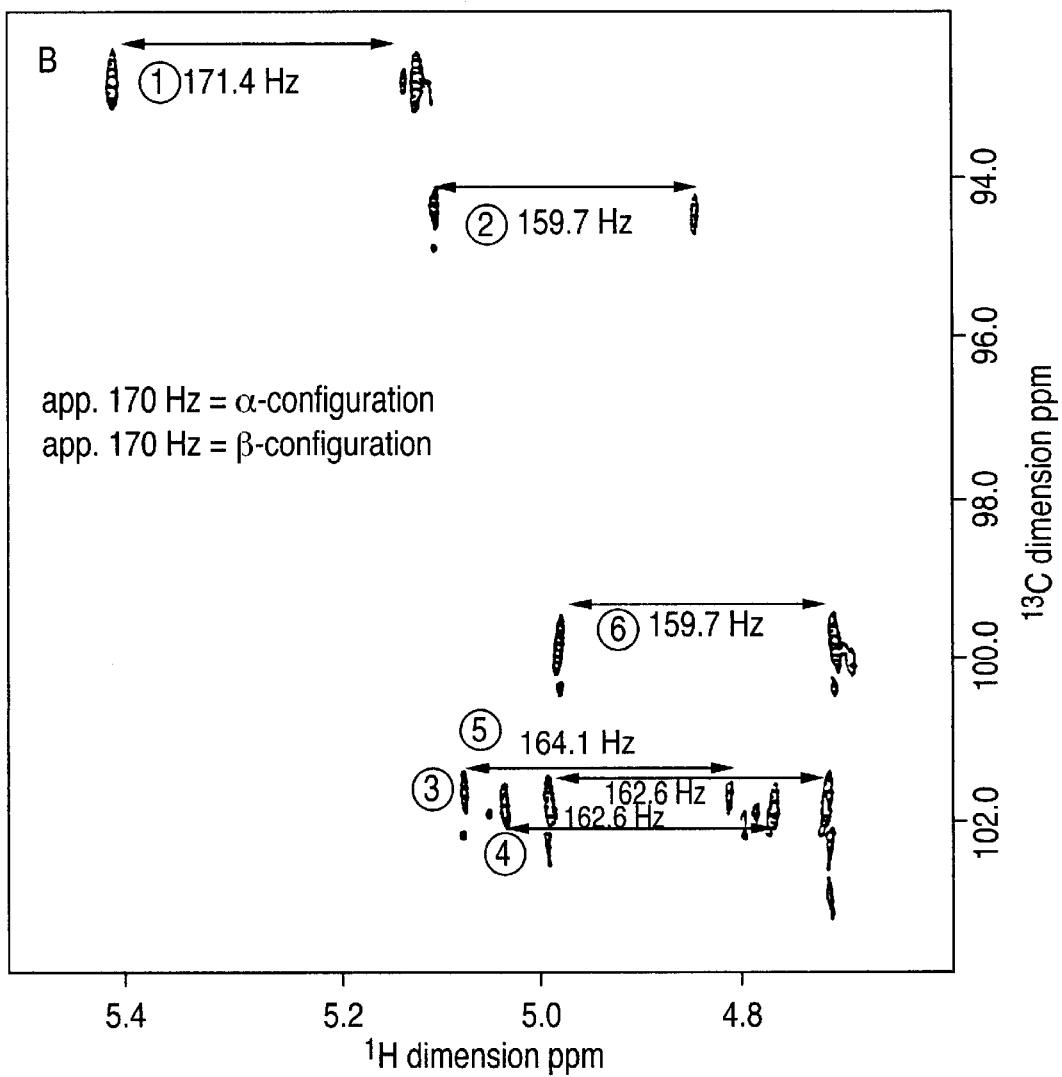
FIG. 20 shows 2-DNMR of B6.1 epitope
Figure 22:
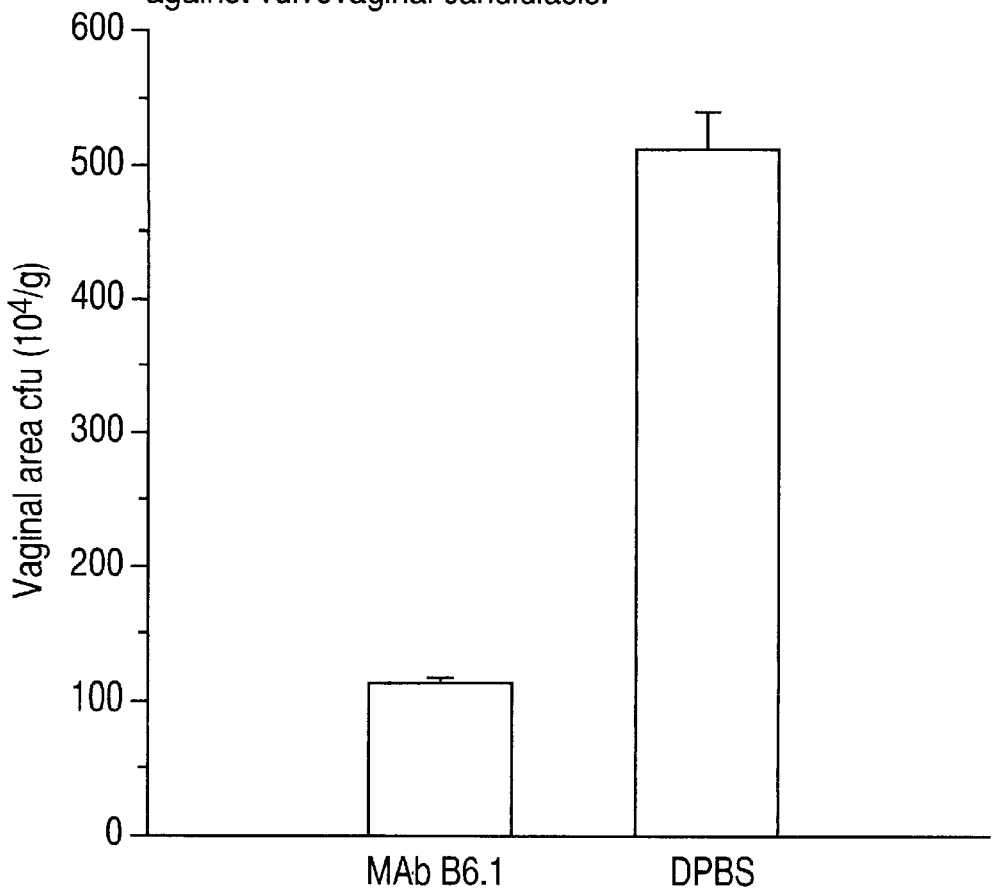
FIG. 22 shows the therapeutic effect of MAb B6.1 on mice against vulvovaginal candidiasis.
Figure 23:
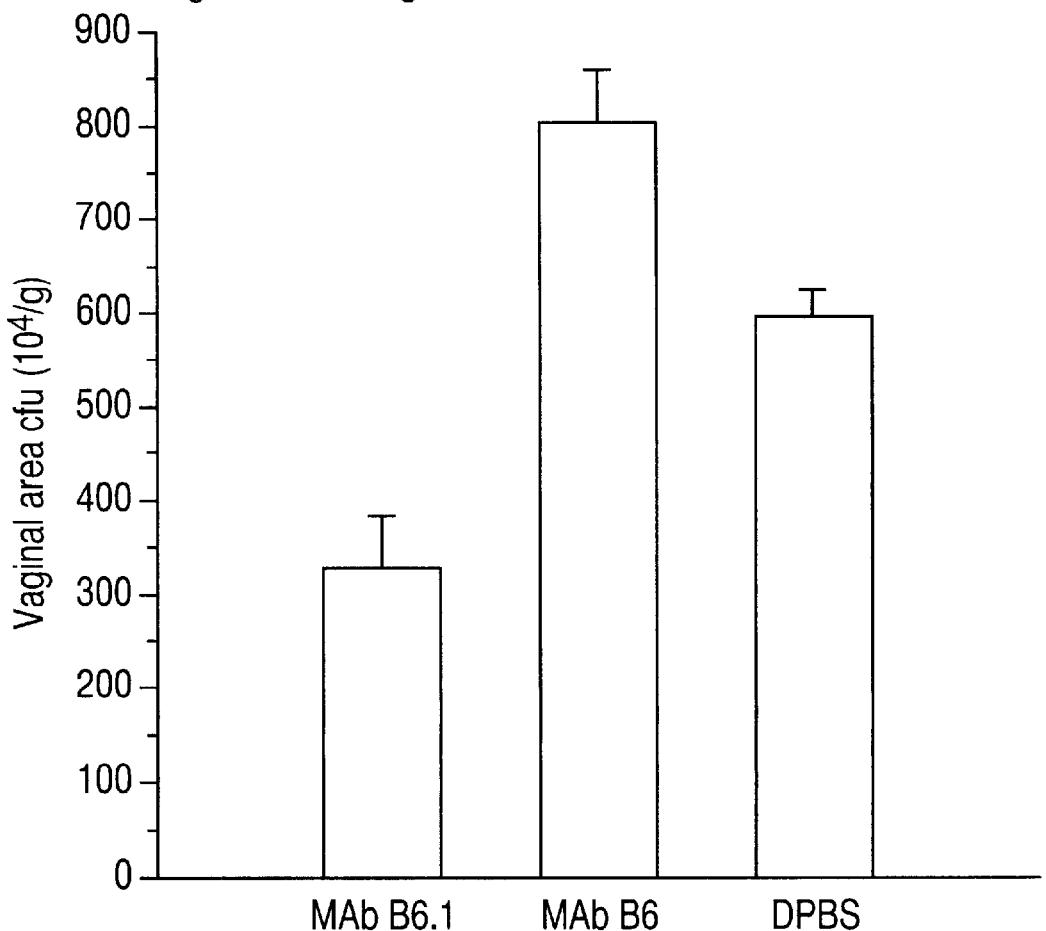
FIG. 23 shows the therapeutic effect of MAb B6.1, MAb 6 and DPBS on mice against vulvovaginal candidiasis.
Figure 24:
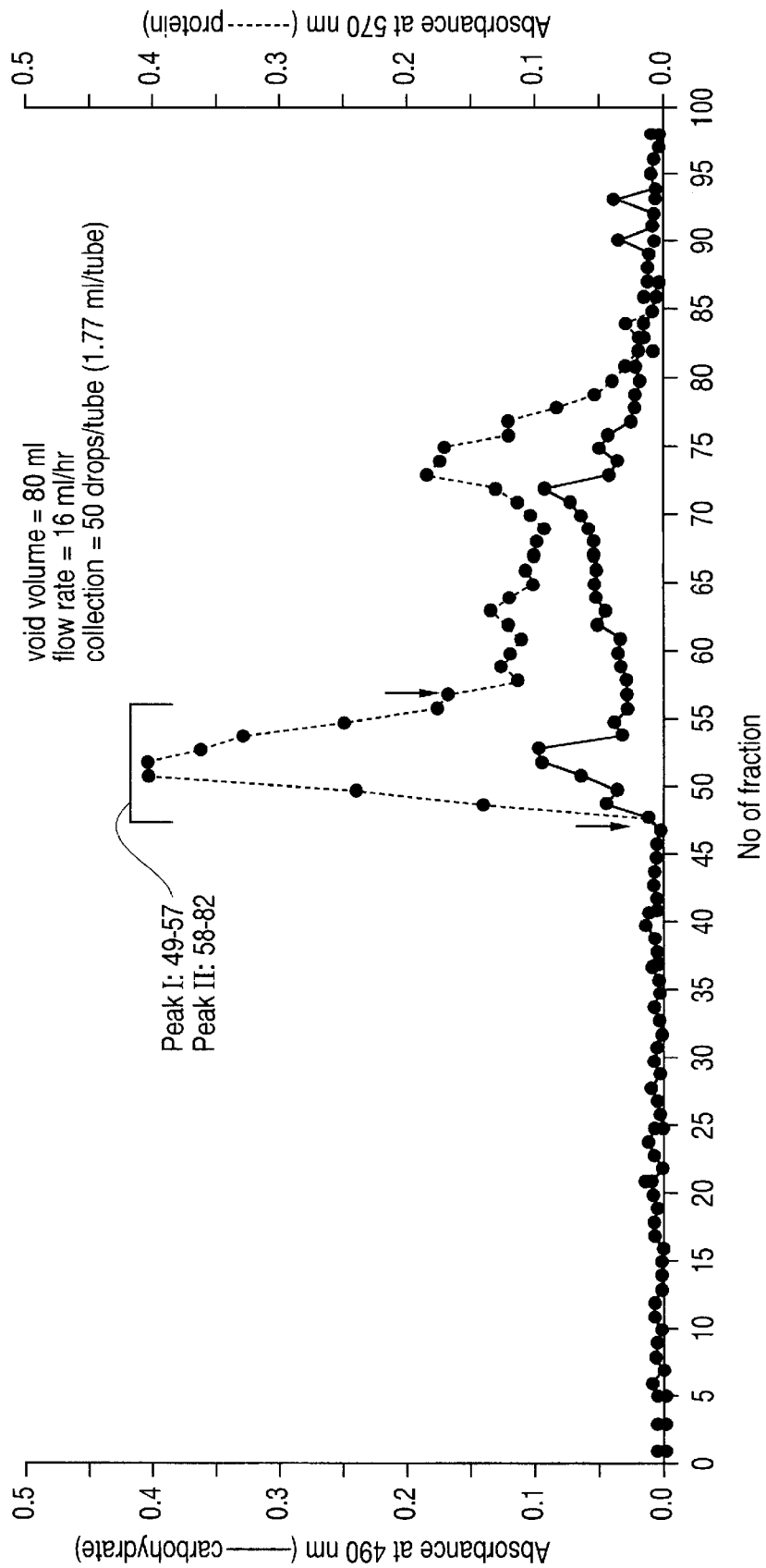
FIG. 24 shows the fractionation profile of the 2ME extract-BSA conjugate sample eluted from the Sephacryl-S-300 size-exclusion column, two peaks were formed.
Figure 25:
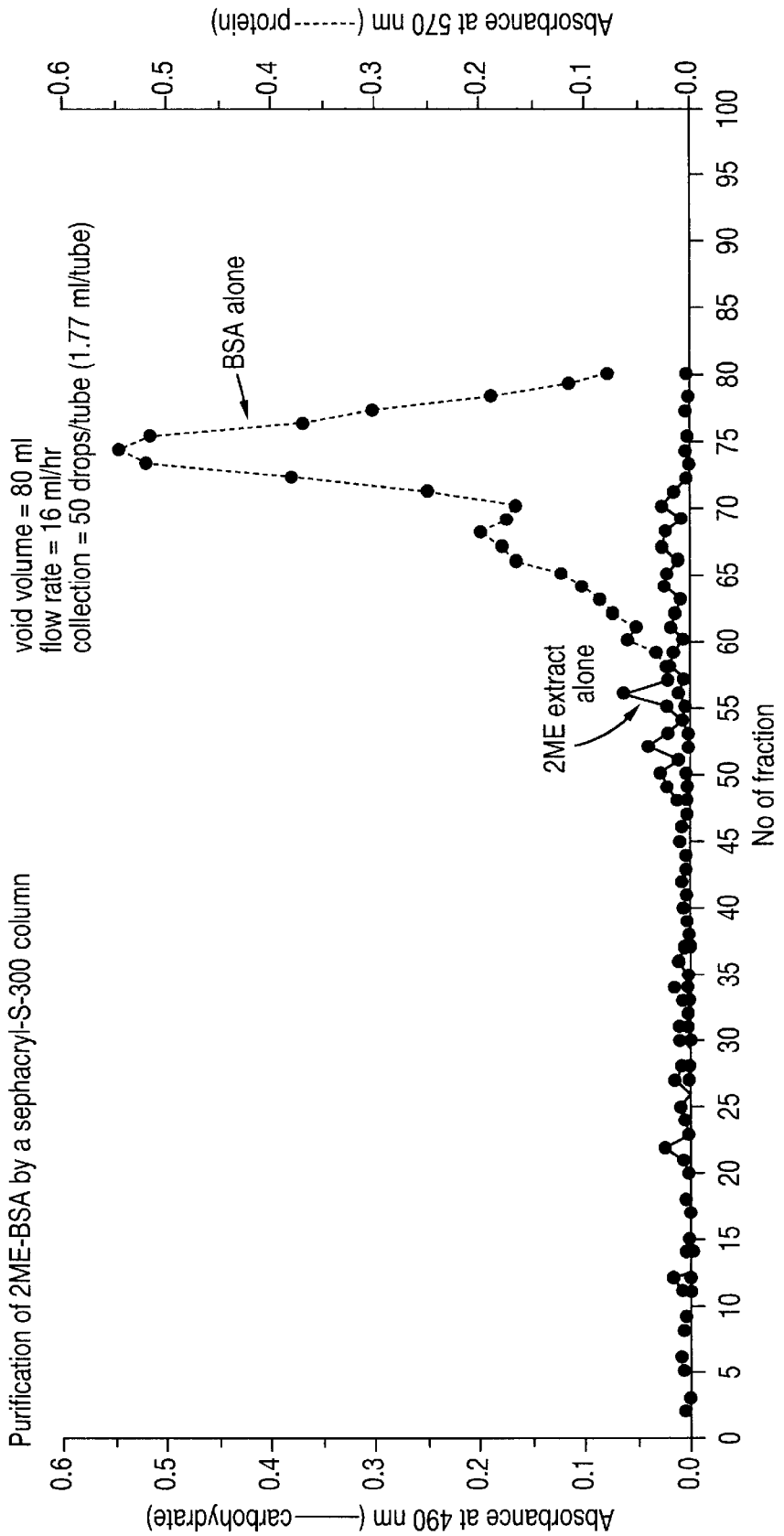
FIG. 25 show the eluting locations (fraction numbers) of unconjugated 2-ME extract and unconjugated BSA.

BALB/cBYJ female mice were given estradiol s.c. and 72 hours later 5×10⁵ *C. albicans* were given intravaginally. One hour later or 4 hours later the mice were given monoclonal antibody or (DPBS) intravaginally. At 24 hours the MAbs or DPBS were given again. At 48 hours the vaginal tissue was processed to determine the *C. albicans* cfu counts. The results are shown in FIGS. 15 and 16. MAb b6.1 protected in both cases. MAb 6 was without effect. These experiments show that certain monoclonal antibodies against *C. albicans* adhesions can provide therapeutic protection against preestablished mucocutaneous *C. albicans* infection.

Electrospray-mass spectrometry (MS) revealed that fractions M3 and M4 contained a trimannose and tetramannose plus trimannose. Reference sugars raffinose (trimer) and stachyose (tetramer) are exactly matched to the sizes of the test fractions. Fractions M3 and M4 reacted with MAb B6.1 as evidenced by their ability to block the interaction of MAb B6.1 with the adhesion complex. However, with equal amounts of each fraction, fraction M3 could block 10-times more adhesion complex interaction with MAb B6.1 than fraction M IV (Table 4). Since fraction M3 is essentially al trimannose, and fraction M4 contains mostly tetramannose and some trimannose, it was concluded that the MAb B6.1 epitope is a trimannose.

Regarding the sugar linkage of the MAb B6.1 epitope, signals at 4.937, 4.880, 4.845, and A.4.823 ppm indicate that $^1$H protons of the non-reducing terminal mannose are of the β-configuration. Signals at 5.265 and 4.964 ppm indicate the α- and β-configurations of the reducing terminal mannose (r), respectively. These $^1$H n.m.r. spectra of the MAb B6.1 epitope almost exactly match the intensity resonances of the phsophomannan complex reported by Kobayashi (Arch. Bio. Bio. 278: 195–204 (1990)). The spectral pattern shows that the epitope is β-linked. Two dimensional n.m.r. showed $^{13}$C chemical shifts of the MA B6.1 epitope that also matched the downfield shifts of fraction M3 from Kobayashi's data. These results indicate that the MAb B6.1 epitope is a β-1,2 linked trimannose. Data are presented showing that the MAb B6 epitope is located in the acid stable part of the adhesion complex (Tables 5 and 6). It is also shown by dot-blot analysis that the acid stable portion of the adhesion complex reacts with MAb B6 but not with MAb B6.1.

EXAMPLE 33

Table 5 shows MAb B6.1-beads by indirect measurement. Fraction M7, even at 2000 μg/ml, does not prevent agglutination of the Ab-coated beads. Fraction M3 inhibits agglutination of this fraction is present in the mixture at ≧20 μg/ml. Fraction M3 (or MIII) has the highest concentration of the MAb B6.1 specific epitope; or, M3 binds with strongest affinity. M4 also reacts with MAb B6.1. Because fraction M4 also contains fraction M3, the inventors conclude that M3 is the epitope for MAb B6.1.

Table 6 shows a determination of agglutinin activity of the acid-stable part with MAb B6.1-beads. This table shows a direct measurement i.e., each fraction was mixed with Ab-beads to determine agglutination of beads.

Table 7 shows a determination of agglutinin activity of the acid-stable part with MAb B.6-beads. This table shows a direct measurement i.e., each fraction was mixed (at indicated concs) with constant amount of Ab-beads to determine agglutination of beads. The acid-stable fractions react with MAb B.6.

Each fraction at indicated concentration was mixed with MAb-B6.1-latex beads to which was added an amount of PMC which is known to cause agglutination of the Ab-coated beads (2 μg).

Fraction M7, even at 2000 μg/ml, does not prevent agglutination of the Ab-coated beads. Fraction M3 inhibits agglutination of this fraction is present in the mixture at ≧20 μg/ml.

Fraction M3 (or MIII) has the highest concentration of the MAb B6.1 specific epitope. Or, M3 binds with strongest affinity. M4 also reacts with MAb B6.1. Because fraction M4 also contains fraction M3, it is concluded that M3 is the epitope for MAb B6.1.

Table 5 shows a determination of agglutinin activity with MAb B6.1-beads by indirect measurement.

TABLE 5

| Sample # | Concentration of each Fraction (microgram/ml) | | | |
|---|---|---|---|---|
| | 2000 | 200 | 20 | 2 |
| M7 (MVII) | + | + | + | + |
| M6 (MVI) | + | + | + | + |
| M5 (MV) | ± /− | + | + | + |
| M4 (MIV) | − | − | + | + |
| M3 (MIII) | − | − | − | + |
| M2 (MII) | + | + | + | + |
| M1 (MI) | + | + | + | + |
| M3 & 4 (MIII, IV) | − | − | − | + |
| all | − | − | + | + |

TABLE 6

| Sample | Concentration of each fraction (microgram/ml) | | | |
|---|---|---|---|---|
| | 2000 | 200 | 20 | 2 |
| A | − | − | − | − |
| B | − | − | − | − |
| C | − | − | − | − |
| D | − | − | − | − |

None of the acid-stable fractions react with MAb-B6.1.

TABLE 7

| Sample | Concentration of each fraction (microgram/ml) | | | |
|---|---|---|---|---|
| | 2000 | 200 | 20 | 2 |
| A | + | + | + | − |
| B | + | + | + | − |
| C | + | + | + | − |
| D | + | + | + | − |

The acid-stable fractions react with MAb B.6.

The mannan complex or its components may be conjugated to proteins (for example Bovine Serum Albumin), polysaccharides, a vector, including a phage vector or other know carrier molecule. The mannan complex does not require liposome delivery for an active vaccine.

The effective dosage for mammals may vary due to such factors as age, weight activity level or condition of the subject being treated. Typically, an effective dosage of a compound according to the present invention is about 0.1 μg to 500 mg when administered either orally, subcutaneously or intramuscularly, as required to confer immunity.

EXAMPLE 34

Applicants have been able to omit the use of liposomes in the vaccine formulation by conjugating the 2-ME extract to a carrier protein, thus, increasing the immunogenicity of the 2-ME extract. The protein, BSA, used in these preliminary experiments was chosen as a prototypic carrier molecule because BSA is readily available and inexpensive. The goal of this work is to purify the 2-ME extract protective epitope (i.e., the β1,2-trimannose), and couple this epitope to an appropriate protein carrier molecule, such as tetanus toxoid or other protein carrier that is acceptable for human use.

On the basis of the fractionation profile of the 2ME extract-BSA conjugate sample eluted from the Sephacryl-S-300 size-exclusion column, two pools of fractions were collected. When the fraction profile was compared to the eluting locations (fraction numbers) of unconjugated 2-ME extract and unconjugated BSA, the first pool, referred to as peak I, appeared to represent the conjugate because this peak eluted much earlier (i.e., it had a higher molecular weight) than either of the unconjugated materials.

I). Determination of concentrations of carbohydrate and protein in peak I of the conjugate sample.

1. The conjugate sample was analyzed by SDS-PAGE (7.5%). Peak I contained protein (as determined by silver staining) and carbohydrate (as determined by periodic acid staining). Peak II also contained both carbohydrate (due mostly to 2-ME extract) and protein (due mostly to BSA), but the electrophoretic position was similar to the position of unconjugated BSA (not shown).

2. The amount of protein in peak I, as determined by Pierce's BCA protein assay, was approximately 54%.

II). Test to determine if peak I conjugate material induces antibodies in test animals.

BALB/cBy female mice (7 week old) from NCI were vaccinated with the conjugate (peak I material) mixed in the Ribi Adjuvant System (R-700) by an i.p. injection. Three different doses of the conjugate were tested; 10, 50, and 250 μg per mouse. Control mice received the adjuvant only by the same route. Three weeks later, the animals were boosted with same formula of vaccine or control adjuvant by the same route. Five days after the booster, blood was drawn from a tail vein, and agglutinin activity in sera was determined against 2-ME coated latex beads.

Result: a positive agglutination reaction occurred.

Agglutinin titers will be determined.

Conjugation of 2-ME to bovine serum albumin (BSA) (The following method is based on Schneerson, et al., work (1986, Infect. Immun. 52:19–528), and some parts are *modified.)

Materials:
1. 2-ME extract isolated from *Candida albicans* CA1 strain
2. cyanogen bromide (CNBr) (Sigma, C-6388, FW=15.9)
3. adipic acid dihydrazide (Sigma, A-0638, FW=174.2)
4. Sephacryl-S-300 (Sigma, Lot#98F0424)
5. 1-ethyl-3 (3-dimethylaminoprophyl) carbodimide.HCl (EDC)(Sigma, E-6383)
6. bovine serum albumin (BSA), (Sigma, A-8022, Fraction V)
7. dialysis tubing (MWCO=6–8,000, Spectrum Medical Industries Co.)

Methods:
(I) Activation of 2-ME extract by cyanogen bromide
1. Activate 2-ME extract at pH 10.5 at 4C for 6 min with 1.0 mg of CNBr per mg of 2-ME extract. Monitor pH continuously; maintain at pH 10.5 by dropwise addition of 0.1 M NaOH. (2-ME extract is dissolved in (10) ml of pyrogen-free water.)
2. Add adipic acid to CNBr-activated 2-ME extract to a final concentration of 0.3M. Adjust pH to 8.5 with 0.2 N HCl. The adipic acid is dissolved in 0.5 M NaHCO$_3$.
3. Allow the reaction mixture to tumble overnight at 4C.
4. Centrifuge the resultant solution at 16,000×g at 4C for 1 hr.
5. Collect supernatant and dialyze it against *deionized-water for 72 hr at 4C. (*Chromatography is not used in our method, but is described in the I&I paper.)
6. Lyophilize (free-dry) dialyzed supernatant material. This material is denoted as the 2-ME hydrazide compound.

(II) Coupling of 2-ME hydrazide to BSA

The BSA is covalently bound to the 2-ME hydrazide derivative by carbodiimide-mediated condensation using 1-ethyl-3(3-dimethylaminopropyl carbodiimide (EDC).
1. Mix 80 mg 2-ME hydrazide and 80 mg BSA in 2.5 ml deion-water. (1:1 ratio of 2-ME hydrazide: BSA by weight).
2. Keep the mixture on ice during the entire procedures.
3. Stir the mixture continuously.
4. Add 4.9 mg of EDC to a final concentration of 0.1 M.
5. The reaction mixture is stirred for 3 hr at 4C, pH 5.0 and dialyzed against 0.2M NaCl (pH 7.0) at 4C overnight, (**When 0.1M EDC is added, it is pH 5.0.)
6. Centrifuge the resultant mixture of 2-ME extract conjugated with BSA at 10,000×g at 4C for 1 hr.
7. Pass the supernatant through a 1.6×100 cm size-exclusion column of Sephacryl-S-300 equilibrated in 0.2 M NaCl.
8. Test each of eluted fractions by the Dubois' carbohydrate assay and by protein assays and also measure absorbance at 220 nm.
9. Fraction(s) containing the 2ME extract-BSA conjugate is lyophilized.

REFERENCES

1. Anttila, V. J., P. Ruutu, S. Bondestam, S. E. Jansson, S. Nordling, M. Farkkilla, A. Sivonen, M. Castren, and T. Ruutu. 1994. Hepatosplenic yeast infection in patients with acute leukemia: a diagnostic problem. Clin. Infect. Dis. 18:979–981.
2. Banerjee, U., L. N. Mohapatra, and R. Kumar. 1984. Role of antibody in defence against murine candidosis. Indian J. Med. Res. 79:760–765.
3. Berenguer, J., M. Buck, F. Witebsky, F. Stock, P. A. Pizzo, and T. J. Walsh. 1993. Lysis-centrifugation blood cultures in the detection of tissue-proven invasive candidiasis. Diagn. Microbiol. Infect. Dis. 17:103–109.
4. Brawner, D. L. and J. E. Cutler. 1984. Variability in expression of a cell surface determinant on *C. albicans* as evidenced by an agglutinating monoclonal antibody. Infect. Immun. 43:966–972.
5. Brawner, D. L. and J. E. Cutler. 1986. Variability in expression of cell surface antigens of *C. albicans* during morphogenesis. Infect. Immun. 51:337–343.
6. Brawner, D. L. and J. E. Cutler. 1986. Ultrastructural and biochemical studies of two dynamically expressed cell surface determinants on *C. albicans*. Infect. Immun. 51:327–336.
7. Brawner, D. L. and J. E. Cutler. 1987. Cell surface and intracellular expression of two *C. albicans* antigens during in vitro and in vivo growth. Microbial Pathogen. 2:249–257.
8. Brawner, D. L. and J. E. Cutler. 1989. Oral *C. albicans* isolates from nonhospitalized normal carriers, immunocompetent hospitalized patients, and immunocompromised patients with or without acquired immunodeficiency syndrome. J. Clin. Microbiol. 27:1335–1341.
9. Campbell, R. C. 1967. The Kolmogorov-Smirnov one-sample test, p. 157–159. In R. C. Campbell (ed.), Statistics for biologists. University Press, Cambridge.

10. Critchley, I. A. and L. J. Douglas. 1987. Isolation and partial characterization of an adhesin from *C. albicans*. J. Gen. Microbiol. 133:629–636.
11. Cutler, J. E., Y. Han, and R. K. Li. 1994. Production of monoclonal antibodies against mannan determinants of *C. albicans*, B. Maresca and G. S. Kobayashi (eds.). p.197–206, In Molecular Biology of Pathogenic Fungi: A Laboratory Manual. Telos Press, New York. p.197–206.
12. Dubois, M., K. A. Gillis, J. K. Hamilton, P. A. Rebers, and F. Smith. 1956. Colorimetric method for determination of sugars and related substances. Analyt. Chem. 28:350–356.
13. Filler, S. G., B. 0. Ibe, A. S. Ibrahim, M. A. Ghannoum, J. U. Raj, and J. E. Edwards. 1994. Mechanisms by which *C. albicans* induces endothelial cell prostaglandin synthesis. Infect. Immun. 62:1064–1069.
14. Fruit, J., J. C. Cailliez, F. C. Odds, and D. Poulain. 1990. Expression of an epitope by surface glycoproteins of *C. albicans*. Variability among species, strains and yeast cells of the genus Candida. J. Med. Vet. Mycol. 28:241–252.
15. Garner, R. and J. E. Domer. 1994. Lack of effect of *C. albicans* mannan on development of protective immune responses in experimental murine candidiasis. Infect. Immun. 62:738–741.
16. Giger, D. K., J. E. Domer, S. A. Moser, and J. T. McQuitty. 1978. Experimental murine candidiasis: pathological and immune responses in T-lymphocyte-depleted mice. Infect. Immun. 21:729–737.
17. Han, Y., N. van Rooijen, and J. E. Cutler. 1993. Binding of *C. albicans* yeast cells to mouse popliteal lymph node tissue is mediated by macrophages. Infect. Immun. 61:3244–3249.
18. Hazen, K. C., D. L. Brawner, M. H. Riesselman, M. A. Jutila, and J. E. Cutler. 1991. Differential adherence of hydrophobic and hydrophilic *C. albicans* yeast cells to mouse tissues. Infect. Immun. 59:907–912.
19. Kanbe, T. and J. E. Cutler. 1994. Evidence for adhesin activity in the acid-stable moiety of the phosphomannoprotein complex of *C. albicans*. Infect. Immun. 62:1662–1668.
20. Kanbe, T., Y. Han, B. Redgrave, M. H. Riesselman, and J. E. Cutler. 1993. Evidence that mannans of *C. albicans* are responsible for adherence of yeast forms to spleen and lymph node tissue. Infect. Immun. 61:2578–2584.
21. Kanbe, T., M. A. Jutila, and J. E. Cutler. 1992. Evidence that *C. albicans* binds via a unique adhesion system on phagocytic cells in the marginal zone of the mouse spleen. Infect. Immun. 60:1972–1978.
22. Kanbe, T., R. K. Li, E. Wadsworth, R. A. Calderone, and J. E. Cutler. 1991. Evidence for expression of C3d receptor of *C. albicans* in vitro and in vivo by immunofluorescence and immunoelectron microscopy. Infect. Immun. 59:1832–1838.
23. Kobayashi, E., N. Shibata, M. Nakada, S. Chaki, K. Mizugami, Y. Ohkubo, and S. Suzuki. 1990. Structural study of cell wall phosphomannan of *C. albicans* NIH B-792 (serotype B) strain, with special reference to 1H and 13C NMO analyses of acid-labile oligomannosyl residues. Arch. Biochem. Biophys. 278:195–204.
24. Komshian, S. V., A. K. Uwaydah, J. D. Sobel, and L. R. Crane. 1989. Fungemia caused by Candida species and *Torulopsis glabrata* in the hospitalized patient: frequency, characteristics, and evaluation of factors influencing outcome. Rev. Infect. Dis. 11:379–390.
IV.25. LaForce, F. M., D. M. Mills, K. Iverson, R. Cousins, and E. D. Everett. 1975. Inhibition of leukocyte candidacidal activity by serum from patients with disseminated candidiasis. J. Lab. Clin. Med. 86:657–666.
26. Lehrer, N., E. Segal, H. Lis, and Y. Gov. 1988. Effect of *C. albicans* cell wall components on the adhesion of the fungus to human and murine vaginal mucosa. Mycopathologia 102:115–121.
27. Li, R. K. and J. E. Cutler. 1993. Chemical definition of an epitope/adhesin molecule on *C. albicans*. J. Biol. Chem. 268:18293–18299.
28. Louria, D. B., R. G. Brayton, and G. Finkel. 1963. Studies on the pathogenesis of experimental *C. albicans* infections in mice. Sabouraudia 2:271–283.
29. Martinez, J. P., M. L. Gil, M. Casanova, J. L. Lopez-Ribot, J. G. De Lomas, and R. Sentandreu. 1990. Wall mannoproteins in cells from colonial phenotypic variants of *C. albicans*. J. Gen. Microbiol. 136:2421–2432.
30. Matthews, R. and J. Burnie. 1992. Acquired immunity to systemic candidiasis in immunodeficient mice: role of antibody to heat-shock protein 90. J. Infect. Dis. 166:1193–1194.
31. Matthews, R. C., J. P. Burnie, D. Howat, T. Rowland and F. Walton. 1991. Autoantibody to heat-shock protein 90 can mediate protection against systemic candidosis. Immunol. 74:20–24.
32. Meunier, F., M. Aoun, and N. Bitar. 1992. Candidemia in immunocompromised patients. Clin. Infect. Dis. 14 (Suppl 1):S120–S125.
33. Miyakawa, Y., T. Kuribayashi, K. Kagaya, and M. Suzuki. 1992. Role of specific determinants in mannan of *C. albicans* serotype A in adherence to human buccal epithelial cells. Infect. Immun. 60:2493–2499.
34. Molinari, A., M. J. Gomez, P. Crateri, A. Torosantucci, A. Cassone, and G. Arancia. 1993. Differential cell surface expression of mannoprotein epitopes in yeast and mycelial forms of *C. albicans*. Eur. J. Cell Biol. 60:146–153.
35. Mourad, S. and L. Friedman. 1961. Active immunization of mice against *C. albicans*. Proc.Soc.Exp.Biol.Med. 106:570–572.
36. Mourad, S. and L. Friedman. 1968. Passive immunization of mice against *C. albicans*. Sabouraudia 6:103–105.
37. Mukherjee, J., M. D. Scharff, and A. Casadevall. 1994. *Cryptococcus neoformans* infection can elicit protective antibodies in mice. Can. J. Microbiol. 40:888–892.
38. Mukherjee, J., L. Zuckier, M. D. Scharff, and A. Casadevall. 1994. Therapeutic efficacy of monoclonal antibodies to *Cryptococcus neoformans* glucuronoxylomannan alone and in combination with amphotericin B. Antimicrob. Agents Chemother. 38:580–587.
39. Mukherjee, S., S. Lee, J. Mukherjee, M. D. Scharff, and A. Casadevall. 1994. Monoclonal antibodies to *Cryptococcus neoformans* capsular polysaccharide modify the course of intravenous infection in mice. Infect. Immun. 62:1079–1088.
40. Nau, D. R. 1986. A unique chromatographic matrix for rapid antibody purification. BioChromatography 1:82–94.
41. Odds, F. C. 1988. Candida and candidosis. Bailliere Tindall, London.
42. Pearsall, N. N., B. L. Adams, and R. Bunni. 1978. Immunologic responses to *C. albicans*. III. Effects of passive transfer of lymphoid cells or serum on murine candidiasis. J. Immunol. 120:1176–1180.
43. Pincus, S. H.; Smith, M. J.; Jennings, H. J.; Burritt, J. B.; Glee, P. M. 1998. Peptides that mimic the group B streptococcal type III capsular polysaccharide antigen. J. Immunol. 160;293–298.
44. Qian, Q., M. A. Jutila, N. van Rooijen, and J. E. Cutler. 1994. Elimination of mouse splenic macrophages correlates with increased susceptibility to experimental disseminated candidiasis. J. Immunol. 152:5000–5008.

45. Reboli, A. C. 1993. Diagnosis of invasive candidiasis by a dot immunobinding assay for Candida antigen detection. J. Clin. Microbiol. 31:518–523.
46. Schaberg, D. R., D. H. Culver, and R. P. Gayner. 1991. Major trends in the microbial etiology of nosocomial infection. Am. J. Med. 16:72S-75S.
47. Sieck, T. G., M. A. Moors, H. R. Buckley, and K. J. Blank. 1993. Protection against murine disseminated candidiasis mediated by a *C. albicans*-specific T-cell line. Infect. Immun. 61:3540–3543.
48. Tronchin, G., J. P. Bouchara, V. Annaix, R. Robert, and J. M. Senet. 1991. Fungal cell adhesion molecules in *C. albicans*. Eur. J. Epidemiol. 7:23–33.
49. Uthayakumar, S. and Granger, B. L. 1995. Cell surface accumulation of overexpressed hamster lysosomal membrane glycoproteins. Cell. and Mol. Biol. Res. 41:405–420.
50. Walker, S. M. and S. J. Urbaniak. 1980. A serum-dependent defect of neutrophil function in chronic mucocutaneous candidiasis. J. Clin. Pathol. 33:370–372.
51. Whelan, W. L., J. M. Delga, E. Wadsworth, T. J. Walsh, K. J. Kwon-Chung, R. Calderone, and P. N. Lipke. 1990. Isolation and characterization of cell surface mutants of *C. albicans*. Infect. Immun. 58:1552–1557.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All publications and patents cited herein are hereby incorporated by reference in their entireties.

What is claimed is:

1. An isolated passively immunizing antibody which binds specifically to the solubilized adhesin fraction of the β-mercaptoethanol extract of the cell surface of *Candida albicans*.

2. The antibody of claim 1, wherein the adhesin fraction is part of the phosphomannoprotein complex of *Candida albicans*.

3. The antibody of claim 1, wherein the adhesin fraction is solubilized by extraction with β-mercaptoethanol.

4. The antibody of claim 1, wherein the antibody is an antibody that binds to the same epitope as monoclonal antibody B6.1, American Type Culture Collection Accession Number HB11925.

5. The antibody of claim 4, wherein the antibody is the monoclonal antibody B6.1, American Type Culture Collection Accession Number HB11925.

6. An isolated passively immunizing antibody which binds specifically to an epitope of the solubilized adhesin fraction of *Candida albicans*, wherein the antibody binds to the same epitope as monoclonal antibody B6.1, American Type Culture Collection Accession Number HB11925.

7. The antibody of claim 6, wherein the adhesin fraction is part of the phosphomannoprotein complex of *Candida albicans*.

8. The antibody of claim 6, wherein the adhesin fraction is solubilized by extraction with β-mercaptoethanol.

9. A therapeutic composition comprising a therapeutically effective amount of the antibody of any of claims 1 to 8 and a carrier.

10. The therapeutic composition of claim 9, wherein the carrier is a pharmaceutically acceptable buffer.

11. A method for passive immunization against candidiasis comprising the step of administering to a patient in need thereof the composition of claim 9.

12. The method for passive immunization against candidiasis of claim 11, wherein the carrier is a pharmaceutically acceptable buffer.

13. A method for the treatment of disseminated candidiasis and mucocutaneous candidiasis comprising the step of administering to a patient in need thereof an effective amount of the composition of claim 9.

14. The method for the treatment of disseminated candidiasis and mucocutaneous candidiasis of claim 13, wherein the carrier is a pharmaceutically acceptable buffer.

15. The antibody of claim 2, wherein the antibody binds to a carbohydrate epitope.

* * * * *

UNITED STATES PATENT AND TRADEMARK OFFICE
CERTIFICATE OF CORRECTION

PATENT NO. : 6,403,090 B1
DATED : June 11, 2002
INVENTOR(S) : Jim E. Cutler et al.

It is certified that error appears in the above-identified patent and that said Letters Patent is hereby corrected as shown below:

Drawings,
Delete Figure 2 and insert the Figure 2 shown below.

Column 1,
Line 17, insert
-- STATEMENT OF GOVERNMENT SUPPORT
    This invention was partially made with government support under National Institute of Health Grant Nos. RO1 AI24912 and RO1 AI37194. --

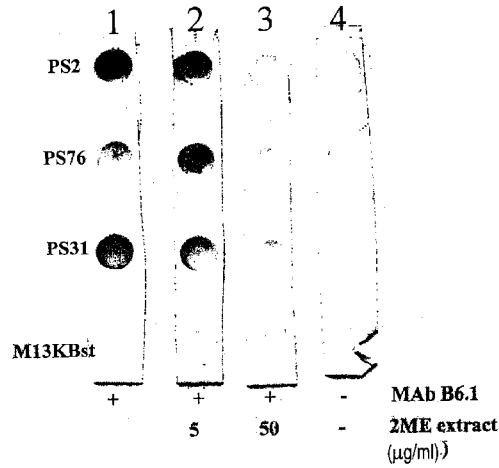

FIG. 2

Signed and Sealed this

First Day of October, 2002

Attest:

JAMES E. ROGAN
Attesting Officer    Director of the United States Patent and Trademark Office